US006338963B1

(12) United States Patent
Glasky et al.

(10) Patent No.: US 6,338,963 B1
(45) Date of Patent: *Jan. 15, 2002

(54) USE OF CARBON MONOXIDE DEPENDENT GUANYLYL CYCLASE MODIFIERS TO STIMULATE NEURITOGENESIS

(75) Inventors: Alvin J. Glasky, Tustin, CA (US); Michael P. Rathbone, Hamilton (CA)

(73) Assignee: NeoTherapeutics, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/420,543

(22) Filed: Oct. 19, 1999

Related U.S. Application Data

(63) Continuation-in-part of application No. 09/086,878, filed on May 29, 1998, now Pat. No. 6,027,936, which is a division of application No. 08/488,976, filed on Jun. 8, 1995, now Pat. No. 5,801,184, which is a continuation-in-part of application No. 08/280,719, filed on Jun. 25, 1994, now Pat. No. 5,447,936.

(51) Int. Cl.[7] .................. C12N 5/00; G01N 33/567; A61K 31/70; A01N 43/42; C07D 473/00

(52) U.S. Cl. .................. 435/325; 435/7.21; 514/45; 514/310; 514/262; 544/265; 544/276

(58) Field of Search .................. 435/7.21, 325; 514/45, 310, 262; 544/265, 276

(56) References Cited

U.S. PATENT DOCUMENTS

| | | | |
|---|---|---|---|
| 3,300,380 A | 1/1967 | Gray et al. | 544/326 |
| 3,321,369 A | 5/1967 | Glasky et al. | 167/65 |
| 3,438,968 A | 4/1969 | Glasky | 260/211.5 |
| 3,666,856 A | 5/1972 | Elion et al. | 544/326 |
| 4,035,486 A | 7/1977 | Laborit | 424/178 |

(List continued on next page.)

FOREIGN PATENT DOCUMENTS

WO 96/03125 A1 2/1996

OTHER PUBLICATIONS

S. Lehmann et al., "Neurite Outgrowth of Neurons of Rat Dorsal Root Ganglia Induced by New Neurotrophic Substances with Guanidine Group," *Neurosci. Lett.* 152: 57–60 (1993).

M. Barinaga, "Carbon Monoxide: Killer to Brain Messenger in One Step," *Science* 259: 309 (1993).

A. Verma et al., "Carbon Monoxide: A Putative Neural Messenger," *Science* 259: 381–384 (1993).

M. Zuo et al., "Nitric Oxide and Carbon Monoxide Produce Activity–Dependent Long–Term Synaptic Enhancement in Hippocampus," *Science* 260: 1946–1950 (1993).

A. Seiger et al., "Intracranial Infusion of Purified Nerve Growth Factor to an Alzheimer Patient: The First Attempt of a Possible Future Treatment Strategy," *Behavioural Brain Res.* 57: 255–261 (1993).

A. Nitta et al., "Effects of Oral Administration of a Stimulator for Nerve Growth Factor Synthesis in Basal Forebrain–Lesioned Rats," *Eur. J. Pharmacol.* 250: 23–30 (1993).

(List continued on next page.)

*Primary Examiner*—Hankyel T. Park
(74) *Attorney, Agent, or Firm*—Oppenheimer Wolff & Donnelly LLP; Michael B. Farber, Esq.

(57) ABSTRACT

Disclosed herein are methods directed generally to the control of neural activity and for selectively and controllably inducing the in vivo genetic expression of one or more naturally occurring genetically encoded molecules in mammals. More particularly, the present invention selectively activates or derepresses genes encoding for specific naturally occurring molecules such as neurotrophic factors through the administration of carbon monoxide dependent guanylyl cyclase modulating purine derivatives. The methods of the present invention may be used to affect a variety of cellular and neurological activities and to therapeutically or prophylactically treat a wide variety of neurodegenerative, neurological, and cellular disorders.

85 Claims, 53 Drawing Sheets

U.S. PATENT DOCUMENTS

| | | | | |
|---|---|---|---|---|
| 4,138,562 | A | 2/1979 | Vince | 544/326 |
| 4,221,794 | A | 9/1980 | Simon et al. | 424/253 |
| 4,221,909 | A | 9/1980 | Simon et al. | 544/265 |
| 4,315,920 | A | 2/1982 | Schaeffer et al. | 424/180 |
| 4,340,726 | A | 7/1982 | Simon et al. | 536/17.4 |
| 4,347,360 | A | 8/1982 | Ogilvie | 544/276 |
| 4,451,478 | A | 5/1984 | Simon et al. | 424/273 R |
| 4,643,992 | A | 2/1987 | Goodman et al. | 514/45 |
| 4,952,693 | A | 8/1990 | Sircar et al. | 544/255 |
| 5,023,294 | A | 6/1991 | Goto et al. | 514/46 |
| 5,091,432 | A | 2/1992 | Glasky | 514/262 |
| 5,093,318 | A | 3/1992 | Goodman et al. | 514/45 |
| 5,187,162 | A | 2/1993 | Marangos et al. | 514/46 |
| 5,237,051 | A | 8/1993 | Garbers et al. | 530/350 |
| 5,256,677 | A | 10/1993 | Sham et al. | 514/351 |
| 5,376,642 | A | 12/1994 | Yarchoan et al. | 514/45 |
| 5,447,939 | A | 9/1995 | Glasky et al. | 514/310 |
| 5,565,437 | A | 10/1996 | Marquez et al. | 514/45 |
| 5,595,901 | A | 1/1997 | Rocancourt et al. | 435/232 |
| 5,795,756 | A | 8/1998 | Johnson et al. | 435/183 |
| 5,801,159 | A | 9/1998 | Miller et al. | 514/45 |
| 5,801,184 | A | 9/1998 | Glasky et al. | 514/310 |
| 5,948,771 | A | 9/1999 | Danziger | 514/185 |
| 6,027,936 | A * | 2/2000 | Glasky | 435/325 |

OTHER PUBLICATIONS

M.H. Tuszynski & F.H. Gage, "Neurotrophic Factors and Neuronal Loss" in *Alzheimer Disease* (R.D. Terry et al., eds., Raven Press, New York, 1994), ch. 25, pp. 405–417.

R.D. Hawkins et al., "Nitric Oxide and Carbon Monoxide as Possible Retrograde Messengers in Hippocampal Long–Term Potentiation," *J. Neurobiol.* 25: 652–665 (1994).

S.H. Snyder, "NO and CO: The Body's Unprecendented Signaling Molecules," *1995 Yearbook of Science and The Future, Encyclopedia Britannica*, pp. 84–101.

R.E. Callard & A.J.H. Gearing, "The Cytokine Facts Book" (Academic Press, London, 1994), pp. 99–100, 104–105, 120–123, 191–200, 235–236.

J.Z. Fields et al., "Cardiac Muscarinic Cholinergic Receptors: Biochemical Identification and Characterization," *J. Biol. Chem.* 253: 3251–3258 (1978).

D.H. Maurice & R.J. Haslam, "Molecular Basis of the Synergistic Inhibition of Platelet Function by Nitrovasodilators and Activators of Adenylate Cyclase: Inhibition of Cyclic AMP Breakdown by Cyclic GMP," *Mol. Pharmacol.* 37: 671–681 (1990).

I.D. Laviada et al., "Phosphatidylcholine–Phospholipase C Mediates the Induction of Nerve Growth Factor in Cultured Glial Cells," *FEBS Lett.* 364: 301–304 (1995).

A. Aurell et al., "The S–100 Protein in Cerebrospinal Fluid: A Simple ELISA Method," *J.Neurol. Sci.* 89: 157–164 (1989).

J. Barnett et al., "Human β Nerve Growth Factor Obtained from a Baculovirus Expression System Has Potent in Vitro and in Vivo Neurotrophic Activity," *Exp. Neurol.* 110:11–24 (1990).

A.J. Glasky et al., "Effect of AIT–082, a Purine Analog, on Working Memory in Normal and Aged Mice," *Pharm. Biochem. Behav.* 47: 325–329 (1994).

P.J. Middlemiss et al., "AIT–082, a Unique Purine Derivative, Enhances Nerve Growth Factor Mediated Neurite Outgrowth from PC12 Cells," *Neurosci. Lett.* 199: 131–134 (1995).

M.M. Bradford, "A Rapid and Sensitive Method for the Quantitation of Microgram Quantities of Protein Using the Principle of Protein–Dye Binding," *Anal. Biochem.* 72: 248–254 (1976).

K.L. Audus et al., "Brain Uptake of Drugs: the Influence of Chemical and Biological Factors," *Adv. Drug Res.* 23: 1–64 (1992).

W.A. Banks & A.J. Kastin, "Measurement of Transport of Cytokines Across the Blood–Brain Barrier," *Meth. Neurosci.* 16: 67–77 (1993).

A.L. Betz, "Identification of Hypoxanthine Transport and Xanthine Oxidase Activity in Brain Capillaries," *J. Neurochem.* 44: 574–579 (1985).

F.G. Blasberg et al., "Transport of α–Aminoisobutyric Acid Across Brain Capillary and Cellular Membranes," *J. Cereb. Blood Flow Metab.* 3: 8–32 (1983).

E.M. Cornford & W.H. Olendorf, "Independent Blood–Brain Barrier Transport Systems for Nucleic Acid Precursors," *Biochim. Biophys. Acta* 394: 211–219 (1975).

A.J. Glasky et al., "Neurotrophins, Growth Factors and Mimetic Agents as Neuroprotectors in the Treatment of Alzheimer's Disease" in *Alzheimer Disease: From Molecular Biology to Therapy* (R. Becker & E. Giacobini, eds., Birkhäuser, Boston, 1996), pp. 119–124.

E.G. Gutierrez et al., "Murine Tumor Necrosis Factor Alpha Is Transported from Blood to Brain in the Mouse," *J. Neuroimmunol.* 47: 169–176 (1993).

M. Hosokawa & M. Ueno, "Aging of Blood–Brain Barrier and Neuronal Cells of Eye and Ear in SAM Mice," *Neurobiol. Aging* 20: 117–123 (1999).

M.D. Johnson & B.D. Anderson, "Localization of Purine Metabolizing Enzymes in Bovine Brain Microvessel Endothelial Cells: An Enzymatic Blood–Brain Barrier for Dideoxynucleosides?," *Pharm. Res.* 13: 1881–1886 (1996).

A.D. Mooradian, "Effect of Aging on the Blood–Brain Barrier," *Neurobiol. Aging* 9: 31–39 (1988).

W. Pan et al., "Permeability of the Blood–Brain Barrier to Neurotrophins," *Brain Res.* 788: 87–94 (1998).

W.M. Pardridge, "CNS Drug Design Based on Principles of Blood–Brain Transport," *J. Neurochem.* 70: 1781–1792 (1998).

J.F. Poduslo et al., "Macromolecular Permeability Across the Blood–Nerve and Blood–Brain Barriers," *Proc. Natl. Acad. Sci. USA* 91: 5705–5709 (1994).

J.F. Poduslo & G.L. Curran, "Permeability at the Blood–Brain Barrier and Blood–Nerve Barriers of the Neurotrophic Factors: NGF, CNTF, NT–3, BDNF," *Mol. Brain Res.* 36: 280–286 (1996).

J.J. Ramirez et al., "AIT–082 Accelerates Septodentate Sprouting After Unilateral Entorhinal Cortex Lesion in Rats," *Soc. Neurosci. Abstr.* 24: 1942 (1998).

G.N. Shah & A.D. Mooradian, "Age–Related Changes in the Blood–Brain Barrier," *Exp. Gerontol.* 32: 501–519 (1997).

I. Skoog et al., "A Population Study on Blood–Brain Barrier Function in 85–Year–Olds: Relation to Alzheimer's Disease and Vascular Dementia," *Neurology* 50: 966–971 (1998).

R. Spector, "Hypoxanthine Transport Through the Blood–Brain Barrier," *Neurochem. Res.* 12: 791–796 (1987).

R. Spector, "Hypoxanthine Transport and Metabolism in the Central Nervous System," *J. Neurochem.* 50: 969–978 (1988).

D. Triguero et al., "Capillary Depletion Method for Quantitation of Blood–Brain Barrier Transport of Circulating Peptides and Plasma Proteins," *J. Neurochem.* 54: 1882–1888 (1990).

W.A. Banks et al., "Measurement of Efflux Rates from Brain to Blood" in *Methods in Molecular Biology, Neuropeptide Protocols* (G.B. Irvine & C.H. Williams, eds., Humana Press, Totowa, NJ, 1997), pp. 353–360.

W.A. Banks et al., "Effects of Wheatgerm Agglutinin and Aging on the Regional Brain Uptake of HIV–1 gp120," *Life Sci.* 65: 81–89 (1999).

M.P. Rathbone et al., "Physiology and Pharmacology of Natural and Synthetic Nonadenine–Based Purines in the Nervous System," *Drug Dev. Res.* 45: 356–372 (1998).

M.P. Rathbone et al., "AIT–082 as a Potential Neuroprotective and Regenerative Agent in Stroke and Central Nervous System Injury," *Exp. Opin. Invest. Drugs* 8: 1255–1262 (1999).

J.S. Bintner et al., "AIT–082, a Hypoxanthine Derivative, Prevents Much of the Decrease in Cerebellar Neuron ATP Following Glutamate Exposure," *Soc. Neurosci.* 25: 2131 (1999) (abstract).

R. Huang et al., "Enhancement of Neuronal Cell Excitability by AIT–082 in Rat Hippocampal Neurons and Its Effects on Second Messenger Systems," *Soc. Neurosci.* 24: 1941 (1998) (abstract).

O.Chu–LaGraff et al., "Effect of AIT–082 on Brain NGF and mRNA Levels and Transport of AIT–082 Across the Blood–Brain Barrier," *Soc. Neurosci.* 24: 1941 (1998) (abstract).

F. Caciagli et al., "The Hypoxanthine Derivative AIT–082 Protects Against Neurotoxicity in Vitro and in Vivo," *Soc. Neurosci.* 24: 1941 (1998) (abstract).

B.H.J. Juurlink et al., "The Hypoxanthine Analogue AIT–082 Promotes Neurite Formation and Regeneration in Cultured Hippocampal Neurons," *Soc. Neurosci.* 24: 1941 (1988) (abstract).

E.M. Taylor et al., "$^{14}$C–AIT082 Crosses the Blood–Brain Barrier and Is Pumped Out of Brain by a Probenecid– and Verapamil–Sensitive Mechanism," *Soc. Neurosci.* 25: 1758 (1999) (abstract).

F. Caciagli et al., "The Hypoxanthine Analogue AIT–082 Mimics the Activity of Guanosine in Affecting Extracellular Adenosine Breakdown and Glutamate Reuptake in Rat Cultured Astrocytes," *Soc. Neurosci.* 25: 1195 (1999) (abstract).

R. Ciccarelli et al., "Guanosine and Related Drugs Stimulate the Production of Neurotrophic Factors from Rat Cultured Astrocytes by Involving Mitogen–Activated Protein Kinase Pathway," *Soc. Neurosci.* 25: 1013 (1999) (abstract).

P.J. Middlemiss et al., "The Synthetic Purine AIT–082 Enhances Recovery After Actue Spinal Cord Crush Injury in Rats," *Soc. Neurosci.* 25: 1002 (1999) (abstract).

P. Di Iorio et al., "The Hypoxanthine Derivative AIT–082 Is Protective Against NMDA– or Kainic Acid–Induced Rat Hippocampal Neurotoxicity in Vivo," *Soc. Neurosci.* 25: 756 (1999) (abstract).

A.G. Gittis & J.R. Puzuasky, "AIT–082 Improves Memory Performance in a Non–Match–to–Sample Task in Rats," *Soc. Neurosci.* 25: 62 (1999) (abstract).

GYSBERS et al., "Neurite Outgrowth in PC12 Cells is Enhanced by Guanosine Through Both Camp–Dependent and Independent Mechanisms" *Neuroscience Letters*, vol. 220, No. 3., 1996, pp. 175–178, abstract.

GYSBERS et al. "GTP and Guanosine Synergistically Enhance NGF–Induced Neurite Outgrowth from PC12 Cells" *International Journal of Developmental Neuroscience*, vol. 14, No. 1, 1996, pp. 19–24, abstract.

DYKEN, P. R., "Subacute Sclerosing Panencephalitis-"*Neurologic Clinics*, vol. 3, No. 1, Feb. 1985 (1985–02), pp. 179–196.

JUURLING et al., "AIT–082 (A Hypoxanthine Derivative), Guanosine and Metabolites Stimulate Neurite Formation in Hippocambial Neurons," *Drug Development Research*, vol. 43, No. 1, Jan. 1998 (1998–01), p. 55, abstract.

AISEN , P. et al., "The Search for Disease–Modifying Treatment for Alzheimer's Disease" *Neurology*, vol. 48, No. 5 suppl. 6, 1997, pp. 35–41.

GLASKY et al., "AIT–082, A Novel Purine Derivative with Neuroregenerative Properties" *Expert Opinion On Investigation Drugs*, vol. 6, No. 10, Oct. 1997 (1997–10), pp. 1413–1417.

RATHBONE, et al., "An Overview of the Neurotrophic Effects of Non–Adenine Based Purines" *Drug Development Research*, vol. 43, No. 1, Jan. 1998 (1998–01), p. 58, abstract.

GLASKY et al., "Effect of AIT–082 Om Neuritogensis in Vitro and Working Memory in Vivo" *Society for Neuroscience Abstracts*, vol. 19, No. 1–3, 1993, p. 38, abstract.

SCRIABINE et al., "The Third International Conference on Neurodegeneration in AD, Parkinson's Disease and Acute Stroke, Princeton, NJ, Jul. 26–27, 1999" *CNS Drug Reviews*, vol. 5, No. 4, Jul. 26–27, 1999, pp. 395–399.

* cited by examiner

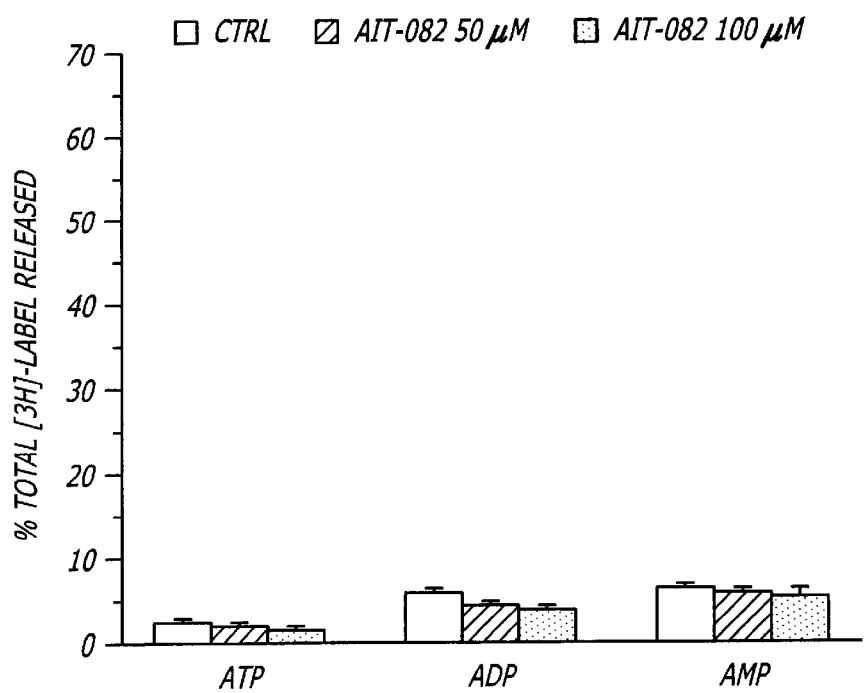
FIG. 29A  RELEASE OF [3H]-NUCLEOTIDES
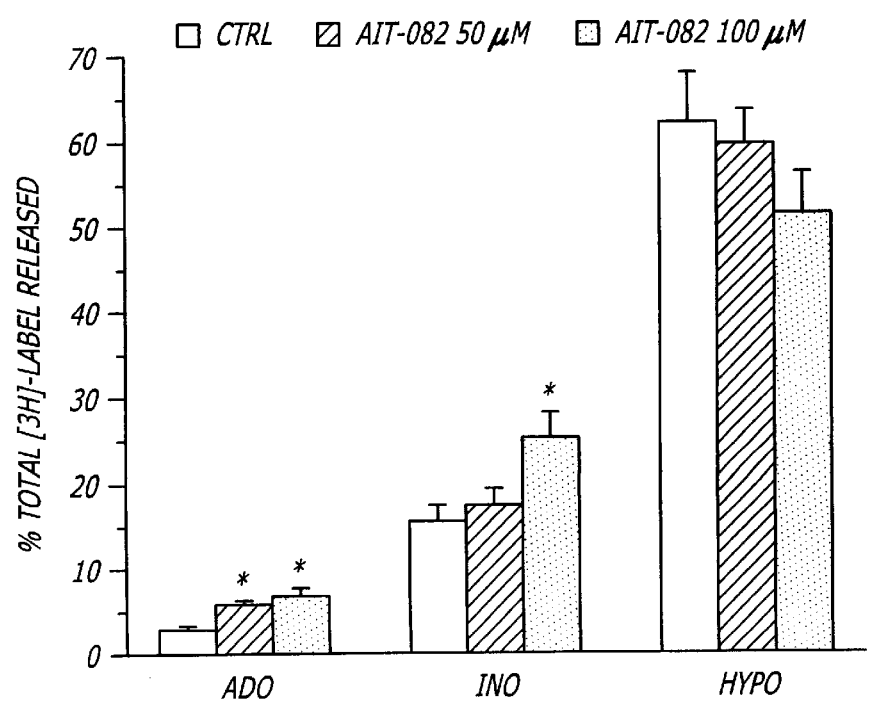
FIG. 29B  RELEASE OF [3H]-NUCLEOTIDES

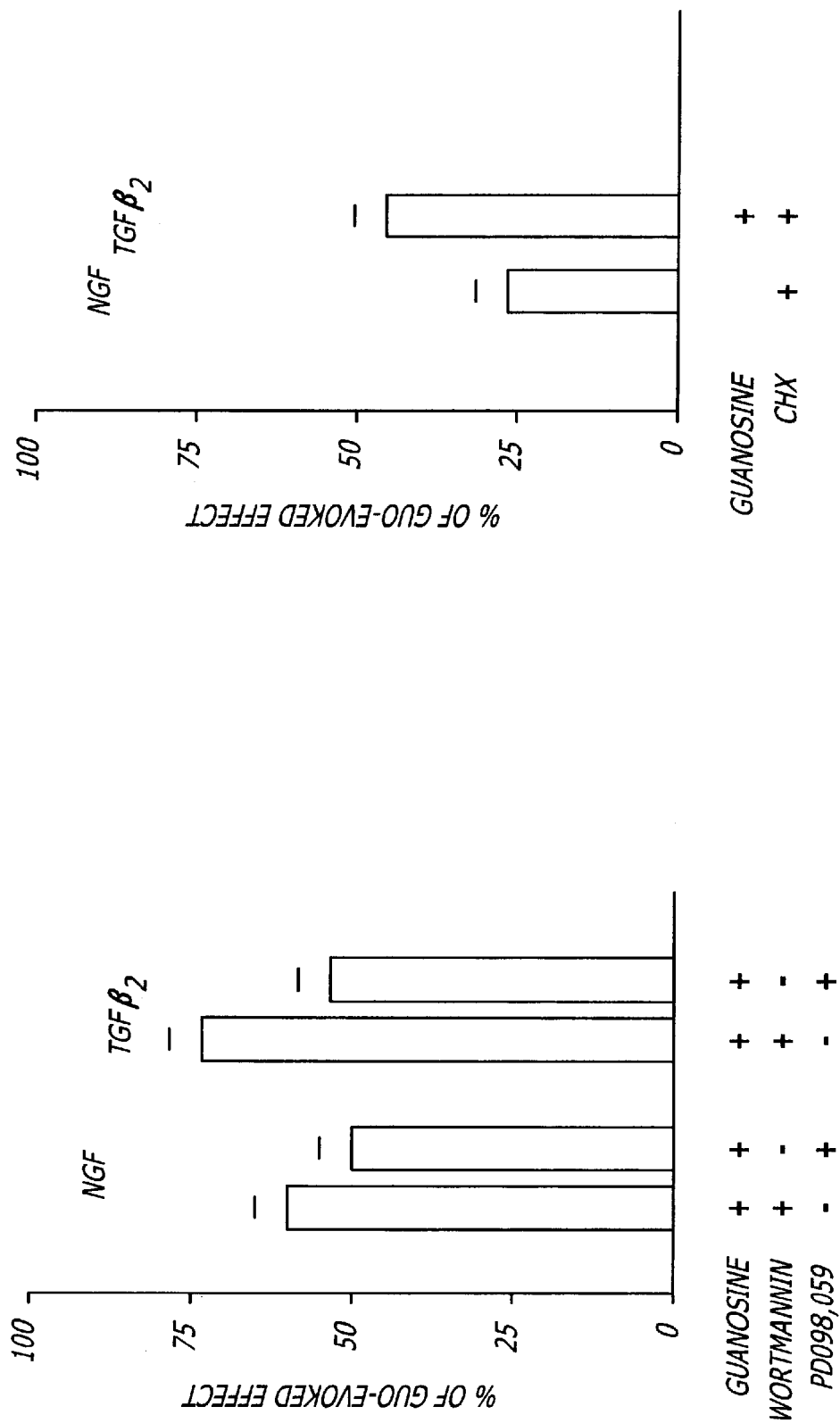

USE OF CARBON MONOXIDE DEPENDENT GUANYLYL CYCLASE MODIFIERS TO STIMULATE NEURITOGENESIS

CROSS-REFERENCES

This application is a continuation-in-part of copending application Ser. No. 09/086,878 filed May 29, 1998, now U.S. Pat. No. 6,027,936 entitled "Car Monoxide Dependent Guanylyl Cyclase Modifiers and Methods of Use," which was a division of copending application Ser. No. 08/488,976, filed Jun. 8, 1995, now U.S. Pat. No. 5,801,184, also entitled "Carbon Monoxide Dependent Guanylyl Cyclase Modifiers and Methods of Use," which was a continuation-in-part of copending application Ser. No. 08/280,719 filed Jul. 25, 1994, now U.S. Pat. No. 5,447,936, also entitled "Carbon Monoxide Dependent Guanylyl Cyclase Modifiers and Methods of Use." The disclosures of these applications are hereby incorporated herein in their entirety by this reference.

FIELD OF THE INVENTION

The present invention relates in general to the control of neural activity and to the treatment of neural disorders. More particularly, the present invention is directed to methods for the modification of mammalian neural activity through the administration of carbon monoxide dependent guanylyl cyclase modulating purine derivatives which selectively and controllably induce the in vivo genetic expression of naturally occurring genetically encoded molecules including neurotrophic factors. The methods of the present invention may be used to affect a variety of neurological activities and to therapeutically or prophylactically treat a wide variety of neurodegenerative and neurological disorders.

BACKGROUND OF THE INVENTION

The evolution of the central nervous system in mammals was a natural response to an increasingly complex environment requiring solutions to difficult problems. The resulting structure is an intricate biochemical matrix that is precisely controlled and attenuated to an elaborate system of chemically modulated regulatory pathways. Through an elaborate series of highly specific chemical reactions, these pathways oversee and direct every structural and operational aspect of the central nervous system and, through it, the organism itself. Normally, the complex interplay of the various control systems cooperates to produce a highly efficient, versatile central nervous system managed by the brain. Unfortunately, when the biochemical matrix of the central nervous system is damaged, either through age, disease, or other reasons, the normal regulatory pathways may be incapable of effectively compensating for the loss. In such cases, it would be highly desirable to modify or supplement the neural mechanisms to prevent such disorders or compensate for them. That is the focus of the present invention.

More specifically, the mammalian brain is composed of approximately 10 billion nerve cells or neurons surrounded by an even greater number of support cells known as neuroglia or astrocyte cells. Neurons, like other cells of the body, are composed of a nucleus, a cytoplasm, and a surrounding cell membrane. However, unlike other cells, neurons also possess unique, fiber-like extensions allowing each individual nerve cell to be networked with literally thousands of other nerve cells to establish a neural infrastructure or network. Communication within this intricate network provides the basis for all mental processes undertaken by an organism.

In each nerve cell, incoming signals are received by neural extensions known as dendrites which may number several thousand per nerve cell. Similarly, neural information is projected along nerve cell axons which may branch into as many as 10,000 different nerve endings. Together, these nerve cell axons and dendrites are generally termed neurites through which each individual neuron can form a multitude of connections with other neurons. As a result, the number of possible neural connections in a healthy brain is in the trillions, giving rise to tremendous mental capacity. Conversely, when the connections within the neural network break down as nerve cells die or degenerate due to age, disease, or direct physical insult, the mental capacity of the organism can be severely compromised.

The connection of the individual axons with the dendrites or cell bodies of other neurons takes place at junctions or sites known as synapses. It is at the synapse that the individual neurons communicate with each other through the flow of chemical messengers across the synaptic junction. The majority of these chemical messengers, or neurotransmitters, are small peptides, catecholamines, or amino acids. When the appropriate stimulus is received by a neural axon connection, the neurotransmitters diffuse across the synapse to the adjacent neuron, thereby conveying the stimulus to the next neuron across the neural network. Based on the complexity of the information transferred between the nerve cells, it is currently believed that between 50 and 100 distinct neurotransmitters are used to transmit signals in the mammalian brain.

Quite recently, it was discovered that nitric oxide (NO) and carbon monoxide (CO) may function as neurotransmitters. These gaseous molecules appear to participate in a number of neuronal regulatory pathways affecting cell growth and interactions. In the brain, as well as in other parts of the body, CO is produced by the enzyme heme oxygenase II (HO). Whether produced from the HO enzyme or from other sources, it is believed that when CO diffuses into a neuron it induces a rise in a secondary transmitter molecule known as cyclic guanosine monophosphate (cGMP) by modulating an enzyme known as guanylate cyclase or guanylyl cyclase. Thus, CO acts as a signaling molecule in the guanylyl cyclase regulatory pathway. The resultant increase in cGMP levels appears to modify several neurotrophic factors as well as other neuronal factors which may induce, promote, or modify a variety of cellular functions including cell growth and intercellular communication.

Neurotrophic factors are molecules that exert a variety of action stimulating both the development and differentiation of neurons and the maintenance of cellular integrity and are required for the survival and development of neurons throughout the organism's life cycle. Generally, neurotrophic factors may be divided into two broad classes: neurotrophins and pleiotrophins. Pleiotrophins differ from the neurotrophins in that they lack a molecular signal sequence characteristic of molecules that are secreted from cells and in that they also affect many types of cells including neurons. Two effects of neurotrophic factors are particularly important: (i) the prevention of neuronal death and (ii) the stimulation of the outgrowth of neurites (either nascent axons or dendrites). In addition, it appears that CO-induced neurotrophic factors may reduce the membrane potential of nerve cells making it easier for the neurons to receive and transmit signals.

Many of today's researchers believe that memory is associated with the modification of synaptic activity, wherein the synaptic connections between particular groups of brain neurons become strengthened or facilitated after repeated activation. As a result, these modified connections activate much more easily. This type of facilitation is believed to occur throughout the brain but may be particularly prominent in the hippocampus, a brain region which is critical for memory. The stimulation of neuronal pathways within the hippocampus can produce enhanced synaptic transmission through these pathways for many days following the original stimulation. This process is known as long term potentiation.

More particularly, long term potentiation is a form of activity-dependent synaptic electrical activity that is exhibited by many neuronal pathways. In this state, generally accepted as a type of cellular memory, nerve cells are more responsive to stimulation. Accordingly, it is widely believed that LTP provides an excellent model for understanding the cellular and molecular basis of synaptic plasticity of the type that underlies learning and memory in vertebrates, including man.

NO and CO are currently the leading candidates for messenger substances that facilitate LTP because inhibitors of these compounds retard the induction of potentiation. The ability to modify neural activity and to increase the ease of LTP using these or other signal transducers could potentially increase learning rates and cognitive powers, possibly, compensating for decreased mental acuity. Prior to the present invention, there were no known agents which could operate on the cellular level in vivo to reliably modify neural regulatory pathways so as to facilitate the LTP of neurons.

In contrast to the enhanced mental capacity provided by long-term potentiation, mental functions may be impeded to varying degrees when the neuronal network is disrupted through the death or dysfunction of constituent nerve cells. While the decline in mental abilities is directly related to the disruption of the neural network, it is important to remember that the disruption is occurring on an individual cellular level. At this level the deleterious effects associated with neuronal disruption may be brought about by any one of a number of factors including neurodegenerative diseases and disorders, aging, trauma, and exposure to harmful chemical or environmental agents. Among the known neurological diseases which adversely impact neuronal function are Alzheimer's disease and related disorders, Parkinson's disease, motor neuropathic diseases such as amyotrophic lateral sclerosis (Lou Gehrig's disease), cerebral palsy, multiple sclerosis, and Huntington's disease. Similar problems may be brought about by loss of neuronal connectivity due to normal aging and to damage to neurons from stroke or other circulatory complications. Direct physical trauma or environmental factors including chemical agents, heavy metals, and the like may also provoke neuronal dysfunction.

Whatever the cause of the neural disorder or dysfunction, the general inability of damaged nerve cells to undergo substantial regrowth or regeneration under natural conditions has led to the proposal that neurotrophic factors be administered to nerve cells in order to help restore neuronal function by stimulating nerve growth and functions. Similarly, stimulating neuritogenesis, or the growth of neurites, by administering neurotrophic factors may contribute to the ability of surviving neurons to form collateral connections and thereby restore neural function.

At present, prior art techniques and compounds have not been effective or practical to directly administer neurotrophic factors to a patient suffering from a neural disorder. In part, this is due to the complex molecular interaction of the neurotrophic factors themselves and to the synergistic regulation of neural cell growth and neuritogenesis. Neurotrophic factors are the result of a long chemical cascade which is exquisitely regulated on the molecular level by an intricate series of transmitters and receptors. Accordingly, neuronal cells are influenced by a concert of different neurotrophic factors, each contributing to different aspects of neuronal development at different times. Neurotrophic factors are, effectively, the tail end of this cascade and thus are one of the most complex components of the regulatory pathway. As such, it was naive for prior art practitioners to assume that the unattenuated administration of single neurotrophic factors at random times (from the cells' viewpoint) could substantially improve cell activity or regeneration. In contrast, modification of the regulatory pathway earlier in the cascade could allow the proper growth factors to be produced in the correct relative amounts and introduced into the complex cellular environment at the appropriate time.

Other practical considerations also preclude the prior art use of neurotrophic factors to stimulate the regeneration of the neuronal network. Neurotrophic factors (including neurotrophins and pleiotrophins) are large proteins and, as such, are not amenable to normal routes of medical administration. For example, these proteins cannot be delivered to a patient or subject orally as the patient's digestive system would digest them before they reached their target neural site. Moreover, due to their relatively large size, the proteins cannot cross the blood-brain barrier and access the most important neurological site in the body. Alternatively, the direct injection of neurotrophic factors into the brain or cerebrospinal fluid crudely overcomes this difficulty but is fraught with technical problems of its own which have thus far proven intractable. For example, direct infusion of known neurotrophins into the brain has proven impractical as it requires administration over a period of years to provide therapeutic concentrations. Further, direct injection into the brain has been associated with dangerous swelling and inflammation of the nerve tissue after a very short period of time. Moreover, such direct injection of substances such as neurotrophic factors into the brain or other nervous tissue is often repugnant to the patient and is thus not acceptable, particularly when it is required repeatedly over a long period of time.

Therefore, there is a need for improved methods of administering neurotrophic factors or stimulating their production so as to enable nerve growth or regeneration.

Accordingly, it is a general object of the present invention to provide methods and associated compositions for effectively modifying mammalian neurons or neural activity to achieve a variety of beneficial results.

Thus, it is another object of the present invention to provide methods and associated compositions for treating mammalian neurological diseases and disorders.

It is yet another object of the present invention to provide methods and associated compositions for inducing long-term changes in the membrane potential of a mammalian neuron.

It is still yet another object of the present invention to provide methods and associated compositions for inducing the in vivo physiological production of genetically encoded molecules and neurotrophic factors within cells.

It is a further object of the present invention to provide methods and associated compositions for enhancing the neuritogenic effects of neurotrophic factors in a physiological environment.

SUMMARY OF THE INVENTION

These and other objects are accomplished by the methods and associated compositions of the present invention which, in a broad aspect, provide for the selective inducement of the in vivo genetic expression and resultant production of naturally occurring genetically encoded molecules including neurotrophic factors, and for the modification of cellular and neural activity through the treatment of mammalian cells with at least one carbon monoxide dependent guanylyl cyclase modulating purine derivative. As will be appreciated by those skilled in the art, the in vivo activation or derepression of genetic expression and the exemplary modification of neural activity brought about by the methods of the present invention may be expressed in a variety of forms or combinations thereof. For example, the treatment of a mammalian cell or neuron through the teachings of the present invention may result in direct administration to the cell of the in vivo expressed molecule through the enhanced cellular production of various naturally occurring genetically encoded neurotrophic factors or in the stimulation of the activity of those factors and their subsequent effect of naturally occurring neuronal development and survival. The methods of the present invention may also stimulate the growth, development, and survival of the cell or neuron directly without the deleterious effect of prior art neurotrophic factor methodology. Further, the present invention may be used to lower or change the membrane potential of the cell, increasing its plasticity and inducing long term potentiation.

Exemplary carbon monoxide dependent guanylyl cyclase modulating purine derivatives useful for practicing the present invention include guanosine, inosine pranobex, and N-4-carboxyphenyl-3-(6-oxohydropurin-9-yl)propanamide (also known as 4-(3-(1,6-dihydro-6-oxo-9-purin-9-yl)-1-oxopropyl)amino) benzoic acid and designated AIT-082) and, unlike prior art compounds, these compounds may be administered directly to a patient either orally or through injection or other conventional routes.

These exemplary compounds are non-toxic and will cross the blood-brain barrier as well.

In a further, more specific aspect, the methods and compositions of the present invention may be used for the treatment or prophylactic prevention of neurological diseases and disorders, including those brought about by disease, age, trauma, or exposure to harmful chemical agents. By promoting the survival, growth, and development of individual neurons and associated cells, the methods of the present invention thereby facilitate the regeneration and development of the neural network and alleviate the manifestations of neural dysfunction. Of course, those skilled in the art will appreciate that pharmaceutical compositions may be formulated incorporating effective concentrations of the carbon monoxide dependent guanylyl cyclase modulating purine derivatives along with pharmaceutically acceptable excipients and carriers. These pharmaceutical compositions may be administered orally, topically, or by injection. Moreover, as the active agents used in the methods of the present invention can cross the blood-brain barrier, they do not have to be injected or infused directly into the brain or central nervous system.

In yet another aspect, the methods and compositions of the present invention may be used to induce long term changes in the membrane potential of the mammalian neuron. These long term potentiation changes may lead to increased membrane plasticity with a corresponding enhancement of cellular memory. In turn, this enhanced cellular memory may elevate the mental capacity of the subject leading to faster learning and increased retention of material.

Specifically, one aspect of the present invention is a method for selectively and controllably inducing the in vivo genetic expression of at least one naturally occurring genetically encoded molecule in a mammal comprising the step of administering an effective amount of at least one carbon monoxide dependent guanylyl cyclase modulating purine derivative to the mammal.

In this method, the at least one naturally occurring genetically encoded molecule can be a molecule that stimulates neuritogenesis. The at least one naturally occurring genetically encoded molecule that stimulates neuritogenesis can be selected from the group consisting of neurotrophins, pleiotrophins, members of the S100 family of EF hand calcium binding proteins, and members of the TGFβ superfamily. Neurotrophins can include nerve growth factor (NGF), NT-3, and brain-derived neurotrophic factor (BDNF). Pleiotrophins can include basic fibroblast growth factor (bFGF) and ciliary neurotrophic factor (CNTF). Members of the S100 family of EF hand calcium binding proteins can include S100β, p11, p9Ka, and calcyclin. Members of the TGFβ superfamily can include $TGF\beta_1$ and glial line-derived neurotrophic factor (GDNF).

The carbon monoxide dependent guanylyl cyclase modulating purine derivative can be selected from the group consisting of guanosine, inosine pranobex, and a compound of formula (I)

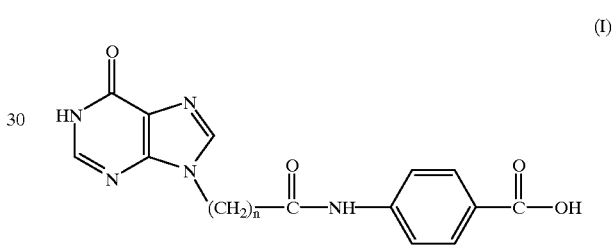

(I)

where n is an integer from 1 to 6 or of a salt or prodrug ester of a compound of formula (I) where n is an integer from 1 to 6. Typically, the compound is a compound of formula (I) where n is an integer from 1 to 6. Preferably, n is 2 and the compound is N-4-carboxyphenyl-3-(6-oxohydropurin-9-yl) propanamide.

Typically, the effective amount of the at least one carbon monoxide dependent guanylyl cyclase modulating purine derivative produces a treating concentration of at least 1 μM.

The at least one carbon monoxide dependent guanylyl cyclase modulating purine derivative can be orally administered to the mammal. Alternatively, the at least one carbon monoxide dependent guanylyl cyclase modulating purine derivative can be administered to the mammal by injection.

The mammal can be a human.

The induction of the in vivo genetic expression of at least one naturally occurring genetically encoded molecule can occur in astrocytes of the mammal. The induction of the in vivo genetic expression of at least one naturally occurring genetically encoded molecule can activate the mitogen-activated protein kinase cascade.

Another aspect of the present invention is a method for the administration of at least one naturally occurring genetically encoded molecule to a mammal comprising the step of selectively inducing the in vivo genetic expression of the molecule in the mammal through the administration of an effective amount of at least one carbon monoxide dependent guanylyl cyclase modulating purine derivative to the mammal to raise the concentration of the at least one naturally occurring genetically encoded molecule in at least one tissue of the mammal and thus cause the administration of the at least one naturally occurring genetically encoded molecule to the mammal.

Yet another aspect of the present invention is a method for modifying the membrane potential of a mammalian neuron comprising the step of administering an effective amount of at least one carbon monoxide dependent guanylyl cyclase modulating purine derivative to the mammalian neuron.

The effective amount of the at least one carbon monoxide dependent guanylyl cyclase can be administered to a mammal so that the method produces an increased learning capability in the mammal.

Still another aspect of the present invention is a method for selectively and controllably inducing the in vivo genetic expression of at least one naturally occurring genetically encoded molecule in a mammal comprising the step of administering an effective amount of at least one carbon monoxide dependent guanylyl cyclase modulating guanine derivative to the mammal, the guanine derivative comprising a guanine moiety linked through its nitrogen-9 atom through a linker to a physiologically active group. Typically, the linker of the guanine derivative incorporates a hydrocarbyl moiety that includes a carbonyl group at one end. Preferably, the end of the hydrocarbyl moiety that is terminated with the carbonyl group is linked to the physiologically active group through an amide linkage.

Preferably, the guanine derivative comprises a compound of formula (II)

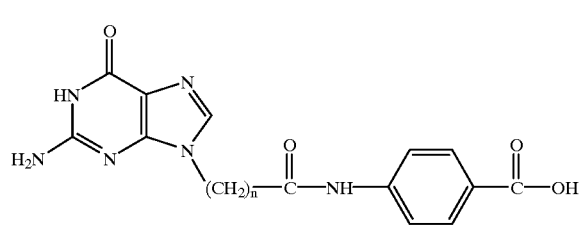

(II)

wherein n is an integer from 1 to 6.

More preferably, in a compound of formula (II), n is 2 and the compound is N-4-carboxyphenyl-3-(2-amino-6-oxohydropurin-9-yl) propanamide.

Other objects, features and advantages of the present invention will be apparent to those skilled in the art from a consideration of the following detailed description of preferred exemplary embodiments thereof taken in conjunction with the data expressed in the associated figures which will first be described briefly.

BRIEF DESCRIPTION OF THE DRAWINGS

FIG. 4A shows the neuritogenic response of cells grown in the presence of methemoglobin, a carbon monoxide scavenger; FIG. 4B shows the same response of cells grown in the presence of methylene blue, a guanylyl cyclase inhibitor FIG. 4C shows the response of cells grown in the presence of zinc protoporphyrin IX, a carbon monoxide scavenger;

FIG. 12A illustrates measured nerve growth factor concentrations for neurons grown in the presence of different concentrations of guanosine triphosphate and FIG. 12B illustrates nerve growth factor concentrations for cells grown in the presence of various concentrations of guanosine;

FIG. 13A illustrates mRNA levels of nerve growth factor (NGF) and FIG. 13B illustrates mRNA levels of fibroblast growth factor (FGF);

FIG. 14A illustrates neuritogenic response to various purine derivatives at different concentrations in the presence of nerve growth factor, FIG. 14B illustrates neuritogenic response in the absence of nerve growth factor and FIG. 14C illustrates neuritogenic response to individual purine derivatives and combinations of purine derivatives in the presence and absence of nerve growth factor;

FIG. 15A illustrates neuritogenic response to various concentrations of inosine; FIG. 15B illustrates the same neuritogenic response to various concentrations of hypoxanthine and FIG. 15C illustrates the neuritogenic response of neuronal cells exposed to different concentrations of xanthine;

FIG. 20A illustrates the neuritogenic response of cells grown in the presence of methylene blue, a guanylyl cyclase inhibitor, FIG. 20B illustrates the neuritogenic response of cells grown in the presence of various concentrations of LY83583, also an inhibitor of guanylyl cyclase, FIG. 20C illustrates the neuritogenic response of cells grown in the presence of various concentrations of atrial natriuretic factor, a hormone which interacts with guanylyl cyclase;

FIG. 22A shows the neuritogenic response of cells grown in the presence of various combinations of nitric oxide donors and hemoglobin and FIG. 22B shows the neuritogenic response of cells grown in the presence of various combinations of nitric oxide donors and methemoglobin;

FIG. 29 is a graph of the effect of AIT-082 on the proportional release of radioactively labeled adenine nucleosides and nucleotides from rat cultured astrocytes: (A) ATP, ADP, and AMP; (B) adenosine, inosine, and hypoxanthine;

FIG. 59 is a graph showing the effect of the mitogen-activated protein kinase cascade and ex novo protein synthesis in the guanosine-induced effect: (A) effects of inhibitors of the protein kinase cascade wortmannin and PD098, 059; (B) effect of the protein synthesis inhibitor cycloheximide;

DETAILED DESCRIPTION

Figure 1:
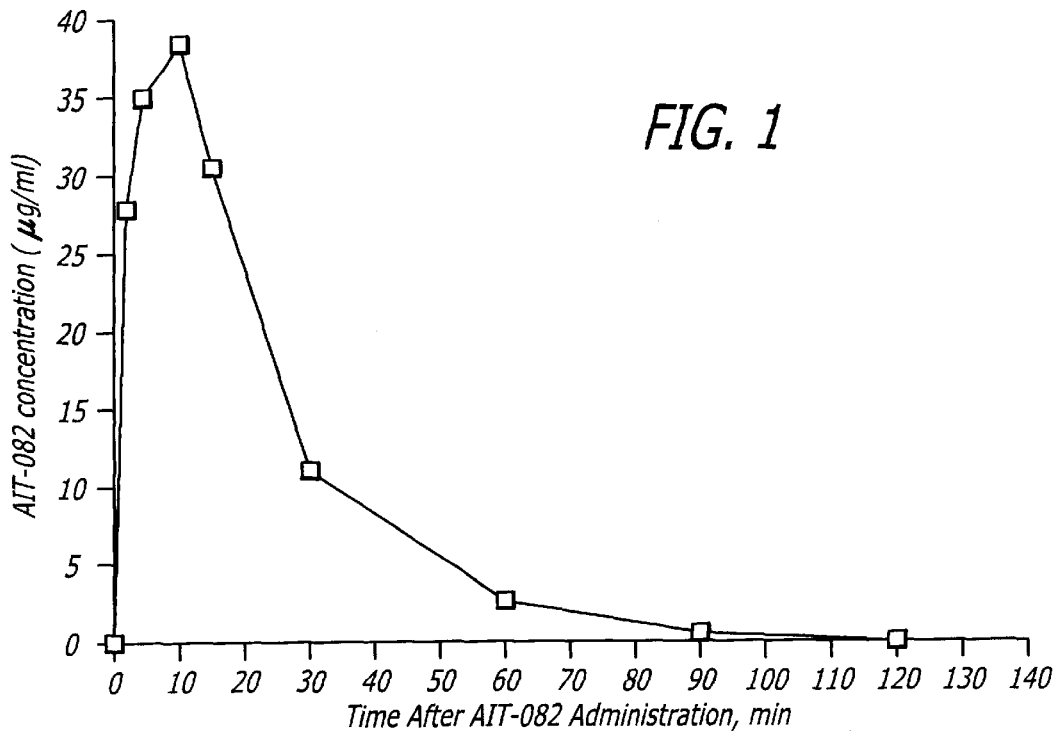
FIG. 1 is a graphical representation of murine plasma concentration following administration of the purine derivative AIT-082 in accordance with the methods of the present invention.

In a broad aspect, the present invention is directed to methods and associated compositions for use in uniquely treating mammalian cells and neurons to modify cellular or neural activity. More specifically, the present invention is directed to the use of effective purine derivatives to modulate the carbon dioxide dependent guanylyl cyclase regulatory system within cells or neurons to produce a variety of beneficial results, including the inducement of in vivo genetic expression of naturally occurring neurotrophic factors and the resultant direct administration of such naturally occurring genetically encoded molecules to a mammal. In exemplary embodiments illustrative of the teachings of the present invention, particular purine derivatives were used to induce genetic expression of encoded molecules, to stimulate neuritogenesis, to enhance neuronal growth and to modify the membrane potential of neurons to produce increased learning capabilities in mammals. Exemplary studies and treatments were performed as discussed below using various dosages and routes of administration of selected exemplary purine derivatives representative of compositions that are effective with the methods of the present invention. Of course, those skilled in the art will recognize that the present invention is not specifically limited to the particular compositions, dosages or routes of administration detailed below.

Depending upon the particular needs of the individual subject involved, the compositions used in the present invention may be administered in various doses to provide effective treatment concentrations based upon the teachings of the present invention. What constitutes an effective amount of the selected composition will vary based upon such factors including the activity of the selected purine derivative, the physiological characteristics of the subject, the extent and nature of the subject's neurodegradation or disorder and the method of administration. Exemplary treatment concentrations which have proven effective in modifying neural activity range from less than 1 $\mu$M to concentrations of 500 mM or more. Generally, initial doses will be modified to determine the optimum dosage for treatment of the particular mammalian subject. The compositions may be administered using a number of different routes including orally, topically, transdermally, intraperitoneal injection or intravenous injection directly into the bloodstream. Of course, effective amounts of the purine derivatives may also be administered through injection into the cerebrospinal fluid or infusion directly into the brain, if desired.

The methods of the present invention may be effected using purine derivatives administered to a mammalian subject either alone or in combination as a pharmaceutical formulation. Further, the purine derivatives may be combined with pharmaceutically acceptable excipients and carrier materials such as inert solid diluents, aqueous solutions or non-toxic organic solvents. If desired, these pharmaceutical formulations may also contain preservatives and stabilizing agents and the like, as well as minor amounts of auxiliary substances such as wetting or emulsifying agents, as well as pH buffering agents and the like which enhance the effectiveness of the active ingredient. The pharmaceutically acceptable carrier can be chosen from those generally known in the art, including, but not limited to, human serum albumin, ion exchangers, dextrose, alumina, lecithin, buffer substances such as phosphate, glycine, sorbic acid, potassium sorbate, propylene glycol, polyethylene glycol, and salts or electrolytes such as protamine sulfate, sodium chloride, or potassium chloride. Other carriers can be used.

Liquid compositions can also contain liquid phases either in addition to or to the exclusion of water. Examples of such additional liquid phases are glycerin, vegetable oils such as cottonseed oil, organic esters such as ethyl oleate, and water-oil emulsions.

The compositions can be made into aerosol formations (i.e., they can be "nebulized") to be administered via inhalation. Aerosol formulations can be placed into pressurized acceptable propellants, such as dichloromethane, propane, or nitrogen. Other suitable propellants are known in the art.

Formulations suitable for parenteral administration, such as, for example, by intravenous, intramuscular, intradermal, and subcutaneous routes, include aqueous and non-aqueous, isotonic sterile injection solutions. These can contain antioxidants, buffers, preservatives, bacteriostatic agents, and solutes that render the formulation isotonic with the blood of the particular recipient. Alternatively, these formulations can be aqueous or non-aqueous sterile suspensions that can include suspending agents, thickening agents, solubilizers, stabilizers, and preservatives. Compositions suitable for use in methods according to the present invention can be administered, for example, by intravenous infusion, orally, topically, intraperitoneally, intravesically, or intrathecally. Formulations of compounds suitable for use in methods according to the present invention can be presented in unit-dose or multi-dose sealed containers, in physical forms such as ampules or vials.

The methods of the present invention provide for the long term modification of various types of cellular or neural activity including the in vivo production of naturally occurring genetically encoded molecules such as neurotrophic growth factors (including neurotrophins, pleiotrophins and cytokines), directly administering such in vivo produced molecules, enhancing the effects of these neurotrophic factors, and the stimulation of cell growth and development. Further, the methods of the present invention may be used to promote neuritogenesis, to form collateral nerve circuits, to enhance the production of cyclic purine nucleotides, to enhance synapse formation and to alter the membrane potential of the neuron. These effects may be extremely beneficial in treating neurodegeneration and increasing learning capacity.

For obvious practical and moral reasons, initial work in humans to determine the efficacy of experimental compositions and methods with regard to such afflictions is unfeasible. Accordingly, in the early development of any drug or therapy it is standard procedure to employ appropriate animal models for reasons of safety and expense. The success of implementing laboratory animal models is predicated on the understanding that the cellular or neurophysiology of mammals is similar. Thus, a cellular or neurotropic response in a member of one species, for example, a rodent, frequently corresponds to the same reaction in a member of a different species, such as a human. Only after the appropriate animal models are sufficiently developed will clinical trials in humans be carried out to further demonstrate the safety and efficacy of a therapeutic agent in man.

With regard to neurodegenerative diseases and disorders and to their clinical effects, the mouse model closely resembles the human pathology of these conditions in many respects. Accordingly, it is well understood by those skilled in the art that it is appropriate to extrapolate the mouse or "murine" model to humans and to other mammals. As with humans, mice are susceptible to learning disorders resulting from neuronal degradation, whether due to traumatic injury, age, disease or harmful chemical agents. Just as significantly, neurotropic factors appear to act in substantially the same manner in a murine model as they do in humans with remarkably similar neuronal reactions. Accordingly, for purposes of explanation only and not for purposes of limitation, the present invention will be primarily demonstrated in the exemplary context of mice as the mammalian subject. Those skilled in the art will appreciate that the present invention may be practiced with other mammalian subjects, including humans, as well.

As will be shown by the data herein, several purine derivatives have been found to work effectively in accordance with the teachings of the present invention. In particular, the data shows that guanosine appears to work well in stimulating the production of neurotrophic factors and enhancing neuritogenesis. Similarly another exemplary purine derivative, N-4-carboxyphenyl-3-(6-oxohydropurin-9-yl) propanamide, also known as 4-(3-(1,6-dihydro-6-oxo- 9-purin-9-yl)-1-oxopropyl)amino) benzoic acid (AIT-082) has been shown to stimulate the in vivo activation or derepression of naturally occurring genes and the resultant production of naturally occurring genetically encoded molecules such as neurotrophic factors; and to increase neuritogenesis, enhance the effects of neurotrophic factors and alter the membrane potential of neurons thereby facilitating long term potentiation of the cells. AIT-082 is disclosed in U.S. Pat. No. 5,091,432 issued Feb. 25, 1992 to a co-inventor of the present application and incorporated herein by reference. Yet another exemplary composition which has been shown to be suitable for use in the present invention is inosine pranobex or isoprinosine. Inosine pranobex, a mixture of inosine and dimethylaminoisopropanol acetamidobenzoate (DIP-PacBa) at a 1:3 molar ratio was found to enhance neuritogenesis and the effects of neurotrophic factors in vitro. The different embodiments of the present invention presented above demonstrate the applicability of using various purine derivatives to modify neural activity through modulating the carbon monoxide dependent guanylyl cyclase system.

Exemplary preferred embodiments of the methods of the present invention involve the treatment of cells or neurons with AIT-082 or 4-(3-(1,6-dihydro-6-oxo-9-purin-9-yl)-1-oxopropyl)amino) benzoic acid. AIT-082 is a unique derivative of the purine hypoxanthine containing a para-aminobenzoic acid moiety. It is rapidly absorbed after oral administration and, after crossing the blood brain barrier, enters the brain unchanged. It may be detected at levels as high as 3.3 ng/mg brain tissue 30 minutes after oral administration. AIT-082 induces the in vivo genetic expression of naturally occurring genetically encoded molecules including neurotrophic factors. As a result, it directly administers these compounds to the treated cells and stimulates neurite outgrowth from neuronal cells when added alone to the cultures as well as enhancing the neuritogenic effects of neurotrophic factors such as nerve growth factor (NGF). More importantly, AIT-082 enhances working memory in old, memory deficient mice after intraperitoneal and oral administration. The neuritogenic activity of AIT-082 is inhibited by hemoglobin, by Methylene Blue, and by ZnPP, all scavengers of CO, but not by CuPP or by other inhibitors of nitric oxide synthase. Screening tests for in vitro activity at known neurotransmitter and neuromodulator receptors were negative.

A further understanding of the present invention will be provided to those skilled in the art from the following non-limiting examples which illustrate exemplary protocols for the identification, characterization and use of purine derivatives in accordance with the teachings of the present invention.

In particular, one aspect of the present invention is a method for selectively and controllably inducing the in vivo genetic expression of at least one naturally occurring genetically encoded molecule in a mammal comprising the step of administering an effective amount of at least one carbon monoxide dependent guanylyl cyclase modulating purine derivative to the mammal.

In this method, the at least one naturally occurring genetically encoded molecule can be a molecule that stimulates neuritogenesis. The at least one naturally occurring genetically encoded molecule that stimulates neuritogenesis can be selected from the group consisting of neurotrophins, pleiotrophins, members of the S100 family of EF hand calcium binding proteins, and members of the TGFβ superfamily.

The induction of the in vivo genetic expression of at least one naturally occurring genetically encoded molecule can occur in astrocytes of the mammal, as demonstrated below in the Examples. This induction causes astrocytes to produce factors that exert a neuroprotective effect against agents such as excitotoxins.

The induction of the in vivo genetic expression of at least one naturally occurring genetically encoded molecule can activate the mitogen-activated protein kinase cascade, as shown below in the Examples. The protein kinases activated in this cascade include ERK1 (44 kilodaltons) and ERK2 (42 kilodaltons).

Neurotrophins can include nerve growth factor (NGF), NT-3, and brain-derived neurotrophic factor (BDNF).

Functional nerve growth factor is a non-covalently linked parallel homodimer. The structure of nerve growth factor consists of three anti-parallel pairs of β-strands together forming a flat surface through which the two subunits associate.

The amino acid sequence for human nerve growth factor and mouse nerve growth factor is known. This molecule is described in R. E. Callard & A. J. H. Gearing, "The Cytokine Facts Book" (Academic Press, London, 1994), pp. 191–198, incorporated herein by this reference.

The growth factor NT-3 also promotes the survival and outgrowth of neural crest-derived sensory and sympathetic neurons. The structure of this molecule is known; its amino acid sequence is identical in the human and mouse. The structure has 60% β-sheet secondary structure and exists as a tightly linked homodimer. NT-3 is described in R. E. Callard & A. J. H. Gearing, "The Cytokine Facts Book" (Academic Press, London, 1994), pp. 199–200, incorporated herein by this reference.

Brain-derived neurotrophic factor also promotes the survival of neuronal populations located either in the central nervous system or directly connected to it. It helps to maintain neurons and their differentiated phenotype in the adult. The amino acid sequence is known for human and mouse BDNF. The molecule has 70% β-sheet secondary structure and is expressed as a tightly associated homodimer. Properties of this molecule are described in R. E. Callard & A. J. H. Gearing, "The Cytokine Facts Book" (Academic Press, London, 1994), pp. 99–100, incorporated herein by this reference.

Pleiotrophins can include basic fibroblast growth factor (bFGF) and ciliary neurotrophic factor (CNTF).

Basic fibroblast growth factor (bFGF), also known as FGF-2, is a protein of 155 amino acids for the human factor. The molecule has an isoelectric point of about 9.6. The molecule is composed entirely of a β-sheet structure with a threefold repeat of a four-stranded antiparallel β-meander which forms a barrel-like structure with three loops. The amino acid sequences for human and mouse bFGF are known. There is no signal sequence, but a truncated form can arise by cleavage between residues 9–10. Further information about bFGF is given at R. E. Callard & A. J. H. Gearing, "The Cytokine Facts Book" (Academic Press, London, 1994), pp. 120–123, incorporated herein by this reference.

Ciliary neurotrophic factor also promotes the survival and differentiation of neuronal cells. CNTF has no homology with NGF, DDNF, and NT-3. The absence of a signal peptide and N-linked glycosylation sites in CNTF is consistent with it being a cytosolic protein. The three-dimensional structure of CNTF is not known, but it has significant homologies with other cytokines, such as IL-6, LIF, oncostatin M, and G-CF. It is thought that these molecules share a four-helix bundle structure. The amino acid sequences of human CNTF and rat CNTF are known. Although these sequences are similar, they are not identical. Further information about CNTF is given at R. E. Callard & A. J. H. Gearing, "The Cytokine Facts Book" (Academic Press, London, 1994), pp. 104–105, incorporated herein by this reference.

Members of the S100 family of EF hand calcium binding proteins can include S100β, p11, p9Ka, and calcyclin. All of these proteins include two EF-hand domains and bind calcium ions.

Members of the TGFβ superfamily can include TGFβ$_1$ and glial line-derived neurotrophic factor (GDNF).

TGFβ$_1$ is a dimeric protein of two identical subunits, each with 112 amino acids, linked by disulfide bonds. The amino acid sequence of human TGFβ$_1$ is known. There is greater than 98% homology between the functional regions of the human and mouse proteins. Further information about TGFβ$_1$ is given in R. E. Callard & A. J. H. Gearing, "The Cytokine Facts Book" (Academic Press, London, 1994), pp. 235–236, incorporated herein by this reference.

GDNF is a glycosylated disulfide-bonded homodimer that promotes survival and morphological differentiation of dopaminergic neurons. Human and rat GDNF have 93% homology. The mature molecule has 134 amino acids and is cleaved from a precursor of 211 amino acids.

The carbon monoxide dependent guanylyl cyclase modulating purine derivative can be selected from the group consisting of guanosine, inosine pranobex, and a compound of formula (I)

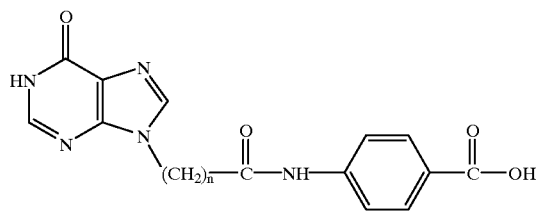

(I)

where n is an integer from 1 to 6 or of a salt or prodrug ester of formula (I) where n is an integer from 1 to 6. Typically, the compound is a compound of formula (I) where n is an integer from 1 to 6. Preferably, n is 2 and the compound is N-4-carboxyphenyl-3-(6-oxohydropurin-9-yl) propanamide, as described above.

Salts and prodrug esters are well known in the art. Prodrug esters release an active compound by hydrolysis of the ester linkage of the prodrug ester.

In addition to the compounds recited above, a number of other guanine derivatives are useful in the methods of the present invention. These are bifunctional compounds that comprise a guanine moiety linked through its nitrogen-9 atom through a linker to a physiologically active group. The length of the linker is chosen so that both the guanine moiety and the physiologically active group can bind to two different receptors. Although a large number of linkers can be used to covalently link the guanine moiety and the physiologically active group, a particularly preferred linker incorporates a hydrocarbyl moiety that includes a carbonyl group at one end. The carbonyl group can be present as part of a substituted aldehyde residue, as part of an ester moiety, or part of an amide moiety. Preferably, the hydrocarbyl moiety is saturated and unbranched. The end of the hydrocarbyl moiety that is terminated with the carbonyl group is linked to the physiologically active group, such as through an amide linkage. A preferred length of the hydrocarbyl moiety is two carbon atoms; this length does not include the functionalized carbon atom that contains the carbonyl group. The length of the linker can be varied according to the physiologically active group covalently linked to the guanine moiety.

The guanine derivatives that are useful in methods according to the present invention include compounds of formula (II), as well as other guanine derivatives.

A 9-substituted guanine derivative particularly useful in methods according to the present invention is a compound in which the physiologically active group is a p-aminobenzoic acid analogue. A 9-substituted guanine derivative according to the present invention incorporating a p-aminobenzoic acid analogue has formula (II) wherein n is an integer from 1 to 6.

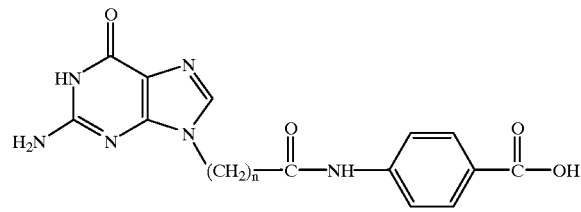

(II)

Preferably, n is 2 and the compound is N-4-carboxyphenyl-3-(2-amino-6-oxohydropurin-9-yl) propanamide.

Analogues of compounds of formula (II) in which the phenyl group of the p-aminobenzoic acid analogue is substituted are also useful in methods according to the present invention.

Typically, the effective amount of the at least one carbon monoxide dependent guanylyl cyclase modulating purine derivative produces a treating concentration of at least 1 μM.

The at least one carbon monoxide dependent guanylyl cyclase modulating purine derivative can be orally administered to the mammal. Alternatively, the at least one carbon monoxide dependent guanylyl cyclase modulating purine derivative can be administered to the mammal by injection.

The mammal can be a human.

Another aspect of the present invention is a method for the administration of at least one naturally occurring genetically encoded molecule to a mammal comprising the step of selectively inducing the in vivo genetic expression of the molecule in the mammal through the administration of an effective amount of at least one carbon monoxide dependent guanylyl cyclase modulating purine derivative to the mammal to raise the concentration of the at least one naturally occurring genetically encoded molecule in at least one tissue of the mammal and thus cause the administration of the at least one naturally occurring genetically encoded molecule to the mammal.

Methods for synthesis of suitable compounds for use in methods according to the present invention are described, for example, in U.S. Pat. No. 5,091,432 to Glasky, incorporated herein by this reference. In general, such methods comprise the steps of: (1) synthesis of an appropriately substituted purine moiety with a 6-amino group linked to an aliphatic linker in which the linker is terminated with a carboxyl group protected as with an alkyl ester; (2) converting the 6-amino group to a 6-oxo group by oxidation, such as with sodium nitrite; (3) hydrolyzing the alkyl ester (or other analogous protecting group) to yield a carboxylic acid; (4) activating the free carboxylic acid by converting it to a nitrophenyl ester; (5) reacting the nitrophenyl ester with a p-aminobenzoate moiety protected with an ethyl ester; and (6) hydrolyzing the ethyl ester protecting the p-aminobenzoate moiety to product the final product. Other reaction sequences are also known in the art.

EXAMPLE 1

Plasma Levels of AIT-082 in Mice

Adult C57BL/6 mice were administered 30 mg/kg of AIT-082 in saline i.p. The animals were sacrificed by decapitation at 30, 45, 60 and 90 minutes after administration of AIT-082. Blood was collected in heparinized tubes, mixed and centrifuged at 2000 rpm for 15 minutes. The plasma supernatant was removed and stored at −70° C. until analysis. A high pressure liquid chromatography system was developed for the analytical measurement of AIT-082 in plasma and brain tissue. The assay developed was selective for AIT-082 in the presence of a number of closely related purine molecules. The sensitivity of the method was 0.1 microgram of AIT-082 per ml of plasma and 0.1 microgram of AIT-082 per milligram of brain tissue (wet weight).

The results of these determinations graphically represented in FIG. 1 where plasma levels of AIT-082 are provided at 5, 10, 15, 20, 30, 60, 90, and 120 minutes after administration of 30 mg/kg i.p. to C57BL/6 mice. From the data, it was estimated that the blood level of AIT-082 reached its peak at approximately 15 minutes.

EXAMPLE 2

AIT-082 Crosses the Blood Brain Barrier

Brain tissue was analyzed from two animals receiving 30 mg/kg i.p. of AIT-082 and sacrificed 30 minutes after drug administration. The brains were rapidly removed and chilled on ice. Brain tissue was dissected into cortex and remainder of the brain. Brain tissue (approx. 250–300 mg wet weight) was homogenized with 5.0 ml of saline using a Brinkman Polytron tissue grinder and stored at −70° C. until analysis. Brain homogenates were deproteinized by ultrafiltration through Gelman Acrodisc filters; first through a 1.2 micron filter and then through a 0.2 micron filter. A 30 ml sample was injected into the HPLC for analysis as above. A standard curve was prepared by the addition of known quantities of AIT-082 to brain homogenates from untreated animals. Analysis of the brain tissue indicated that AIT-082 was detected in both the cortex sample and the remaining brain samples from both animals. The results are shown directly below in Table A.

TABLE A

Brain Tissue Levels of AIT-082

| Sample # | Brain Region | Brain weight (mg) | Level of AIT-082 (ng/mg brain tissue) |
| --- | --- | --- | --- |
| S3 | Cortex | 181 | 2.8 |
| S3 | Remainder | 153 | 3.3 |
| S4 | Cortex | 146 | 3.4 |
| S4 | Remainder | 217 | 2.3 |

This demonstration of the presence of AIT-082 in the brain tissue after 30 minutes is critical in that it indicates that AIT-082 crosses the blood-brain barrier without degradation.

EXAMPLE 3

AIT-082 Interacts with the Cholinergic System

Because of the finding that there is a severe loss of cholinergic neurons in the hippocampus in Alzheimer's disease patients, there has been considerable interest in the effect on memory of compounds which alter the activity of this system. Support for the cholinergic hypothesis of memory comes from studies using lesions or a stroke model. Lesions of the CA1 region of the hippocampus appear to specifically disrupt working memory. In the stroke model, occlusion of the vertebral and carotid arteries (30 minutes) produces specific cell loss in the CA1 region of the hippocampus and a loss of working memory. In these models in aged rats, physostigrnine, a cholinesterase inhibitor, has been shown to improve memory. THA, another drug which increases cholinergic function, was shown to improve memory in aged monkeys. The observation that AIT-082 improves memory in the same general manner as physostigmine and THA raises the question of whether AIT-082 might have some effect on the cholinergic system.

To elucidate the mechanisms by which AIT-082 improves memory, attempts were made to block its actions by co-administration of the short-acting cholinergic antagonist atropine to mice and subjecting them to simple learning tests. Atropine reportedly has the ability to block the effects of physostigmine and THA. Mice were injected with AIT-082 (30 mg/kg) 2 hr prior to testing on days 1 through 4. Atropine (0.5 mg/kg) was injected ½ hour prior to testing or 1.5 hours after AIT-082 on day 3 only. All injections were i.p. After a reference run to determine where the reward was placed in a T-maze, the mice were retested to determine if they could remember the location of the reward. The percentage of correct responses is graphically represented in FIG. 2.

Figure 2:
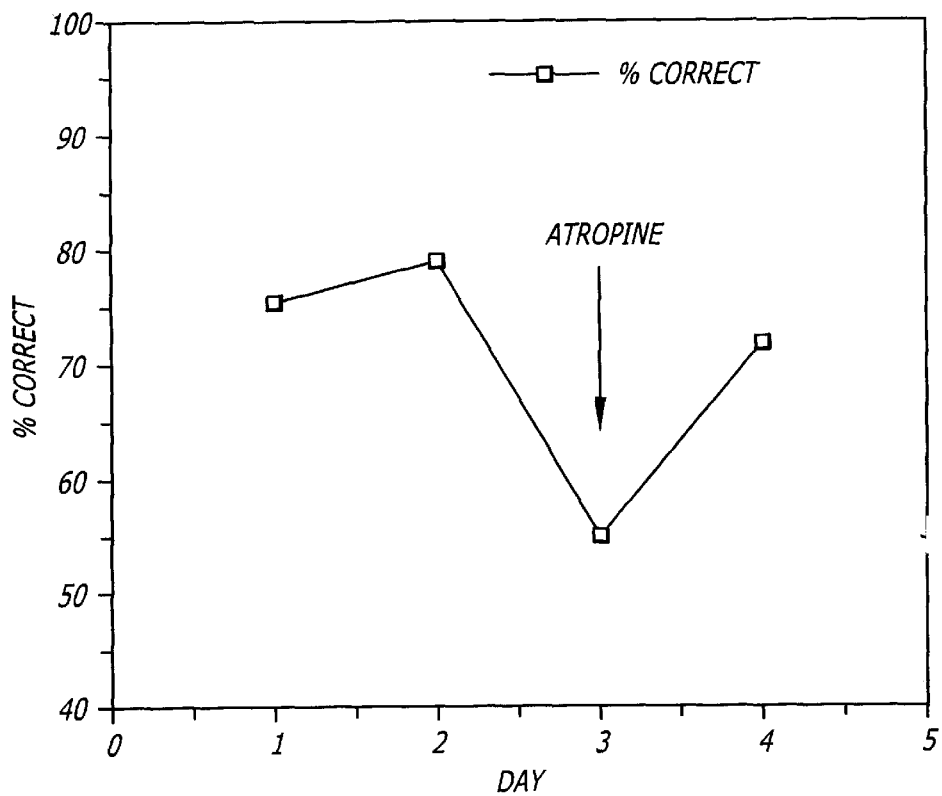
FIG. 2 is a graphical representation of the effect of atropine, a cholinergic antagonist, on memory enhancement in mice by the purine derivative AIT-082.

FIG. 2 demonstrates that atropine blocked the memory enhancing activity of AIT-082 on day 3 and that the effect was transient since the memory enhancing effects of AIT-082 reappeared on day 4 when no atropine was administered. This observation suggests that a cholinergic mechanism may be involved in the action of AIT-082.

EXAMPLE 4

Effect of AIT-082 on Acetylcholine Receptors

The interaction of AIT-082 with acetylcholine receptors was determined by interference with the binding of QNB (3-quinuclidinyl benzilate) in mouse tissue using the method of Fields (*J. Biol. Chem.* 253(9): 3251–3258, 1978). There was no effect of AIT-082 in this assay.

In the study, mice were treated with AIT-082 at 30 mg/kg 2 hours prior to sacrifice, decapitated and the tissue processed to obtain membranes containing the acetylcholine receptors. When these tissues were assayed in vitro, there was no effect of AIT-082 on affinity (Kd) for QNB when AIT-082 was administered under the same conditions as utilized in testing for effects on memory. There was a change in the number of receptors (B max) in cortex and striatum, with the cortex showing a decrease and the striatum an increase in acetylcholine binding sites. These data are consistent with the hypothesis that there is an increased input to the cortex as a result of AIT-082 being administered to the animals. Typically, an increased input will result in down regulation of the receptors.

EXAMPLE 5

Effect of AIT-082 on Receptor Ligand Binding in vitro

AIT-082 was evaluated for its ability to inhibit ligand binding to 38 isolated receptors. The receptors screened and their ligands were:

Adenosine

Amino Acids:
- Excitatory Amino Acids (glycine, kainate, MK-801, NMDA, PCP, quisqualate and sigma);
- Inhibitory Amino Acids (benzodiazepine, GABA-A, GABA-B, and glycine)

Biogenic Amines (doparnine-1, dopamine-2, serotonin-1, serotonin-2)

Calcium Channel Proteins (nifedipine, omegaconotoxin, chloride, potassium)

Peptide Factors (ANF, EGF, NGF)

Peptides: (angiotensin, arg-vasopressin-V1 and V2, bombesin, CCK central and peripheral, neurotensin, NPY, somatostatin, substance k, substance P, VIP)

Second Messenger Systems:
- Adenyl Cyclase
- Protein Kinase (phorbol ester and inositol triphosphate)

The testing was conducted under contract at Nova Labs (Baltimore, Md.). AIT-082 had no activity in any of the in vitro assays conducted.

Accordingly, while AIT-082 acts through the cholinergic nervous system (atropine blocks its activity), AIT-082 appears to act through a mechanism that does not involve direct interaction with acetylcholine receptors. It is of importance to note that in vitro, AIT-082 does not bind to the adenosine receptor.

AIT-082 was evaluated in a series of psychopharmacological tests that were established in order to more fully evaluate the scope of its central nervous system activity. Among the tests utilized were:

(a) motor coordination, by the accelerating Roto-Rod treadmill, (b) exploratory and home cage locomotor activity, by the Stoelting activity monitor, (c) anxiolytic activity, by the elevated Plus maze, and (d) nocioception.

AIT-082 was compared with standard reference drugs.

EXAMPLE 6

AIT-082 Increases Motor Coordination in Mice

Motor coordination was measured using an accelerating Roto-Rod treadmill for mice (Ugo Basile Co.). At various times after treatment with saline or drug, mice were placed on the Roto-Rod, which accelerates to maximum speed over a 5 minute period. The time in seconds at which the subject falls off was recorded in Table B directly below. Each animal was tested 3 times and the mean time was recorded.

TABLE B

Effect of AIT-082 on Roto-Rod Performance

| AIT dose (mg/kg) | Time (sec) |
|---|---|
| Control | 123 ± 64 |
| 0.005 | 162 ± 93 |
| 0.05 | 207* ± 73 |
| 0.5 | 184* ± 76 |
| 30.0 | 187* ± 68 |
| 60.0 | 229* ± 80 |

*p < 0.05, t-test vs controls

Subjects receiving AIT-082 showed improved motor coordination by remaining on the roto-rod for longer periods of time when compared to control (saline) or low doses (0.005 mg/kg).

EXAMPLE 7

AIT-082 Does not Inhibit Exploratory Activity

To measure exploratory behavior, subjects received saline or AIT-082 administration, were placed in a novel large cage (25×48×16 cm, W×L×H), and movement was measured at one-minute intervals for 30 minutes. The large cage (San Diego Instruments, San Diego, Calif.) was equipped with vertical detectors and rearing movements were also recorded. No effects were noted with respect to exploratory activity indicating that the subjects were not incapacitated.

EXAMPLE 8

AIT-082 Does not Inhibit Locomotor Activity

To measure home cage locomotor activity, the home cage was placed on a platform of an activity monitor (Stoelting Instruments). Home cage locomotor activity movements were recorded at one minute intervals for 15 minutes. Subjects received saline or AIT-082 and were returned to their home cages. Ten minutes after injection, the home cage was replaced on the platform of the activity monitor. Home cage locomotor activity movements were recorded at one minute intervals for 30 minutes. During the first five minutes, grooming activity was also monitored and recorded. The results are shown in Table C directly below.

TABLE C

Effect of AIT-082 on Locomotor Activity

| AIT dose (mg/kg) | Movements (mean ± S.D.) | | |
|---|---|---|---|
| | Pre-drug | Post-drug | Difference |
| Control | 1633 ± 434 | 1385 ± 492 | 248 ± 492 |
| 0.005 | 1884 ± 230 | 1375 ± 563 | 509 ± 429 |
| 0.05 | 1718 ± 606 | 1508 ± 456 | 209 ± 340 |
| 0.5 | 1610 ± 349 | 1320 ± 689 | 290 ± 435 |
| 30.0 | 1440 ± 264 | 1098 ± 189 | 342 ± 267 |
| 60.0 | 1690 ± 223 | 634* ± 223 | 1056* ± 154 |

*p < 0.05, t = test vs controls

As shown by the data in Table C, at the high dose (60 mg/kg), subjects may have become more habituated to their environment and exhibited less movement after treatment with AIT-082. Otherwise, no effects were noted.

EXAMPLE 9

AIT-082 Does not Substantially Increase Anxiety

A Plus maze was constructed of black plexiglass consisting of two opposite-facing open arms (30×5 cm, L×W) and two opposite facing closed arms (30×5×15 cm, L×W×H). The walls of the closed arms were clear plexiglass and the four arms were connected by a central area 5×5 cm. The entire Plus maze was mounted on a base 38 cm above the floor. Testing consisted of placing the subject at one end of one of the open arms. The time the subject took to leave the start position (the first 10 cm of the open arm) was recorded. The time it took for the subject to enter halfway into one of the closed arms was also recorded. When the subject arrived at the half-way point in the closed arm, the three-minute test session began. During the three-minute test session, the number of times the subject entered the open arms was recorded. An entry was defined as placing at least two paws onto the platform of the open arm. There was a slight anxiogenic effect of AIT-082 at 30 mg/kg, but this was not observed at a higher dose (60 mg/kg) or at the lower doses (0.005 to 0.5 mg/kg).

EXAMPLE 10

AIT-082 Does not Effect Nocioception

Mice were placed on an electric hot plate (Ominitech) at 55° C. and the latency time until the subject licked his hind paw was measured. If there was no response by 45 seconds, the trial was terminated. By this test there was no effect of AIT-082 on nocioception.

EXAMPLE 11

AIT-082 is not Toxic

Preliminary acute toxicity tests in rats and mice of AIT-082 have demonstrated that the LD50 is in excess of 3000 mg/kg when administered by the oral or intraperitoneal route. AIT-082 has been evaluated under Panlabs's General Pharmacology Screening Program (Panlabs, 11804 North Creek Parkway South, Bothell, Wash. 98011) and the results indicated an absence of any toxicity when measured in their standard profile of 79 different test systems.

By the nature of the chemical structure of AIT-082, it is not anticipated that the compound will be metabolized into any toxic metabolites.

In conclusion, there were few deleterious effects of AIT-082 on a variety of psychopharmacological tests except for a slight anxiogenic effect at one dose. There was an increase in motor coordination (roto-rod test) over a range of doses (0.05 to 60 mg/kg) and possibly a learning or habituation effect at one dosage (60 mg/kg) in the locomotor test.

Following psychopharmacological characterization of this exemplary compound, further studies were conducted to demonstrate the neurogenic effects of the present invention.

EXAMPLE 12

AIT-082 Promotes Neuritogenesis in PC12 Cells

Much of the work performed in the characterization of the compounds of the present invention involved the use of PC12 cells. These cells are derived from a rat pheochromocytoma and when grown in the presence of NGF, extend neurites, cease cell division and assume many characteristics of sympathetic neurons. When cultured in the absence of nerve growth factor (NGF), few PC12 cells have neurites greater than one cell diameter. Addition of saturating concentrations of NGF for 48 hours stimulates neurite outgrowth in about 20–35% of the cells. Because they constitute a homogeneous population of neuronal-like cells, without contaminating astroglia type cells, it is possible to study the direct effects of the purine based compounds on neurite outgrowth in these cells.

To demonstrate neuronal modification by the exemplary compounds of the present invention, a dose response curve of AIT-082 was generated measuring the stimulation of neuritogenesis in PC12 cells. Cells cultured in RPMI 1640 with 1.5% horse serum and 1.5% fetal bovine serum were re-plated onto poly-ornithine coated 24-well culture plates ($2.5 \times 10^4$ cells per well). AIT-082 and NGF were added to the various cultures immediately upon plating. After 48 hours, medium was removed and the cells irnmediately fixed in 10% formalin and PBS for 10 minutes. Cells and neurites were counted within 2 days of fixation.

A neurite was defined as a process extending from the cell at least 1 cell body diameter in length and displaying a growth cone at its tip. For each treatment, 2 representative microscope fields were counted from each of 6 sister cultures receiving identical treatments. The total number of cells counted per well (approximately 100 cells) and the total number of cells containing neurites in each well were used to determine fraction of neurite-bearing cells. The mean values (±SEM) were then determined for each of the treatments. To facilitate comparison neurite outgrowth was expressed relative to the proportion of cells bearing neurites in the presence of NGF alone (NGF=100%). The effects of compounds with and without NGF were compared by analysis of variance (ANOVA) followed by Tukey's test for significance.

Figure 3:
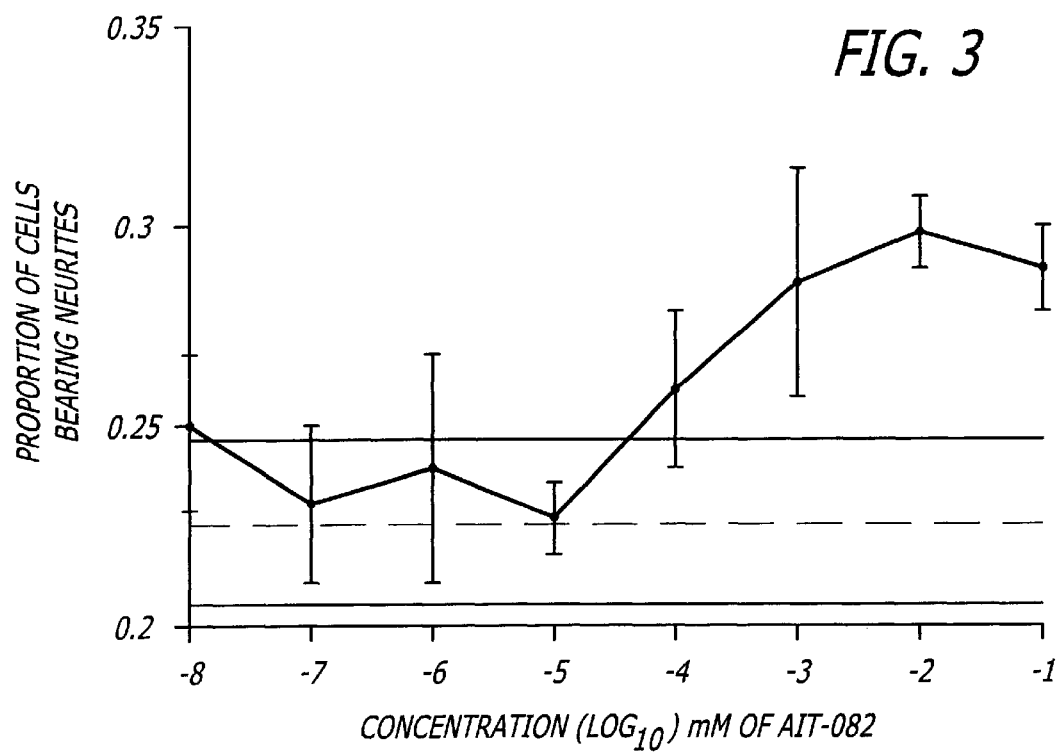
FIG. 3 is a graphical representation of nerve growth factor mediated neuritogenic response in neuronal cells grown in vitro with various concentrations of the purine derivative AIT-082.

The results are shown in FIG. 3 where the curve represents different levels of AIT-082 plus saturating concentrations (40 ng/ml) NGF. The center horizontal line represents control values for cells cultured in the presence of 40 ng/ml NGF alone. Upper and lower horizontal lines are indicative of confidence limits of NGF alone as determined using standard statistical methods.

As shown in FIG. 3, AIT-082 stimulates neuritogenesis and enhances NGF-stimulated neuritogenesis in PC12 cells at low concentrations (1 mM). Analysis of the data shows that AIT-082 was as effective as NGF in promoting neuritogenesis in PC12 cells and enhanced the optimal effects of NGF by 30%. For the purposes of comparison, and as will be discussed in more detail below, inosine and hypoxanthine are weakly effective in stimulating neuritogenesis and in enhancing NGF-stimulated neuritogenesis in PC12 cells but are effective at lower concentrations of 30–300 nM. Guanosine produces a significant effect similar to AIT-082 but at a higher concentration of 30–300 mM.

EXAMPLE 13

Effect of Inhibitors of AIT-082 Neuritogenesis

Age-related memory loss has been associated with loss of NGF-dependent basal forebrain neurons. It can be ameliorated by i.c.v. infusion of NGF. The effect of AIT-082 on neuritogenesis alone and with NGF were studied using the protocol of Example 12. In order to study the mechanism by which AIT-082 exerts its effects, a series of experiments was conducted in which inhibitors were utilized to block or modify specific biochemical processes. All of the cultures contained NGF at optimal dose (40 ng/ml) so the series without AIT-082 added represented the effect of the inhibitors on NGF activity. Where indicated, AIT-082 was added at 10 mM, its apparent, presently understood, optimal dose. Three selective inhibitors were used.

Figure 4A:
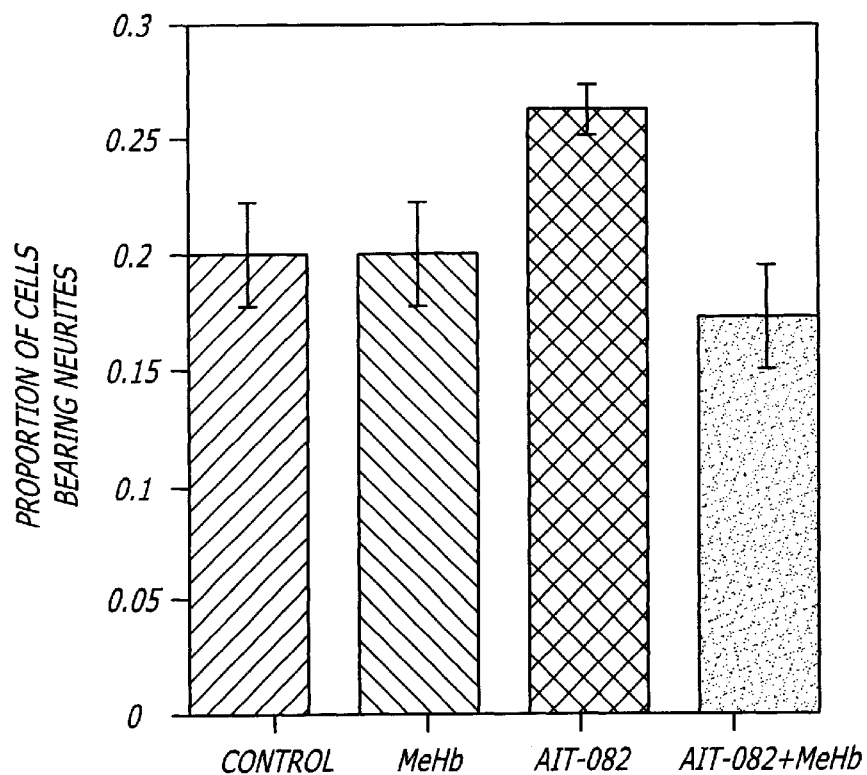
FIGS. 4A, 4B and 4C are graphical comparisons of the effects of selective inhibitors and the purine derivative AIT-082 on nerve growth factor mediated neuritogenic response.
Figure 4B:
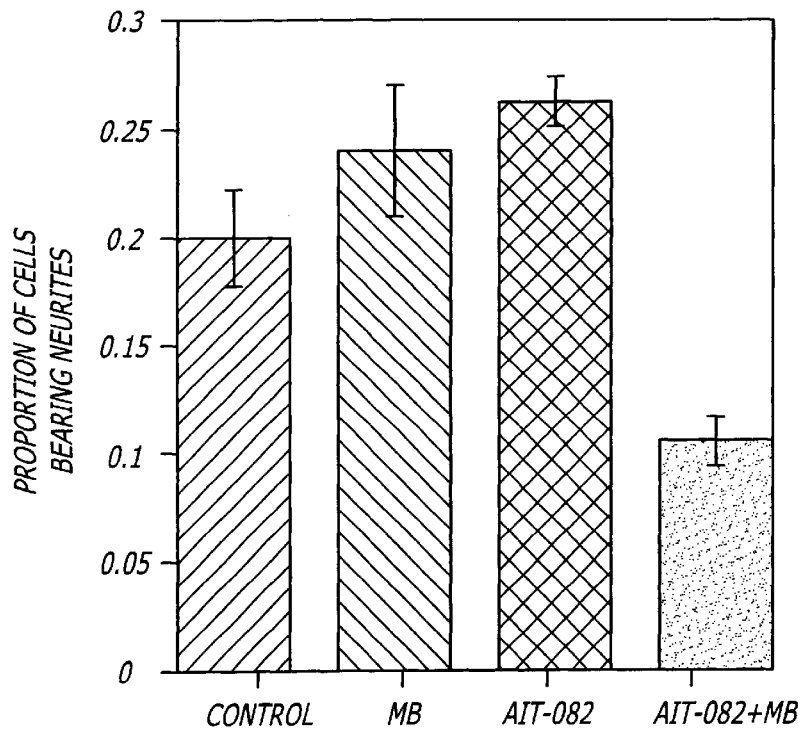
Figure 4C:
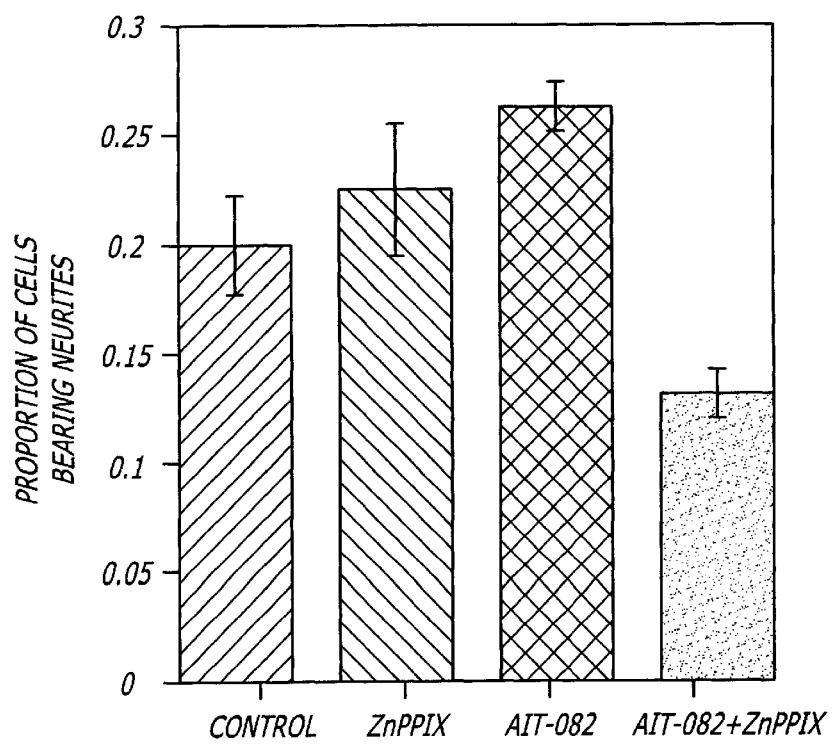

The results of these studies are shown below in Table D below, and FIGS. 4A, 4B, and 4C graphically present the proportion of cells bearing neurites after 48 hours of culture under the conditions indicated. The baseline value was cells grown without NGF or AIT-082.

TABLE D

Effect of AIT-082 and Selective Inhibitors on Neuritogenesis Alone and with NGF

| Inhibitor | Concentration | AIT-082 alone[1] | NGF alone | AIT-082 + NGF |
|---|---|---|---|---|
| None |  | 0.2 ± 0.02 | 0.2 ± 0.02 | 0.26 ± 0.01 |
| Methemoglobin | 0 |  | 0.2 ± 0.02 | 0.26 ± 0.01 |
|  | 1 µM |  | 0.2 ± 0.02 | 0.17 ± 0.02 |
| Methylene Blue | 0 |  | 0.2 ± 0.02 | 0.26 ± 0.01 |
|  | 5 µM |  | 0.24 ± 0.03 | 0.10 ± 0.01 |
| Zn Protoporphyrin IX | 0 |  | 0.20 ± 0.02 | 0.26 ± 0.01 |
|  | 1 µM |  | 0.22 ± 0.03 | 0.13 ± 0.01 |

[1]Proportion of cells bearing neurites

Methemoglobin (MHb) captures and removes nitric oxide (NO) and carbon monoxide (CO) from the culture media. Mh had no effect on NGF activity but inhibited the action of AIT-082, implying that either NO or CO is involved in the action of AIT-82.

Methylene blue (MB) inhibits soluble guanylyl cyclase, the enzyme which produces cyclic GMP (cGMP), an intracellular substance which, as previously discussed, is involved in the second messenger system of nerve impulse transmission. MB had no effect on NGF activity but inhibited the action of AIT-082, implying that guanylyl cyclase is involved in the mechanism of action of AIT-082.

Zinc protoporphyrin IX (ZPP) is an inhibitor of heme oxygenase 2, which produces carbon monoxide. ZPP had no effect on NGF activity but inhibited the action of AIT-082, implying that the production of carbon monoxide is involved in the mechanism of action of AIT-082.

EXAMPLE 14

Effect of Nitric Oxide Inhibitors on AIT-082

Figure 5A:
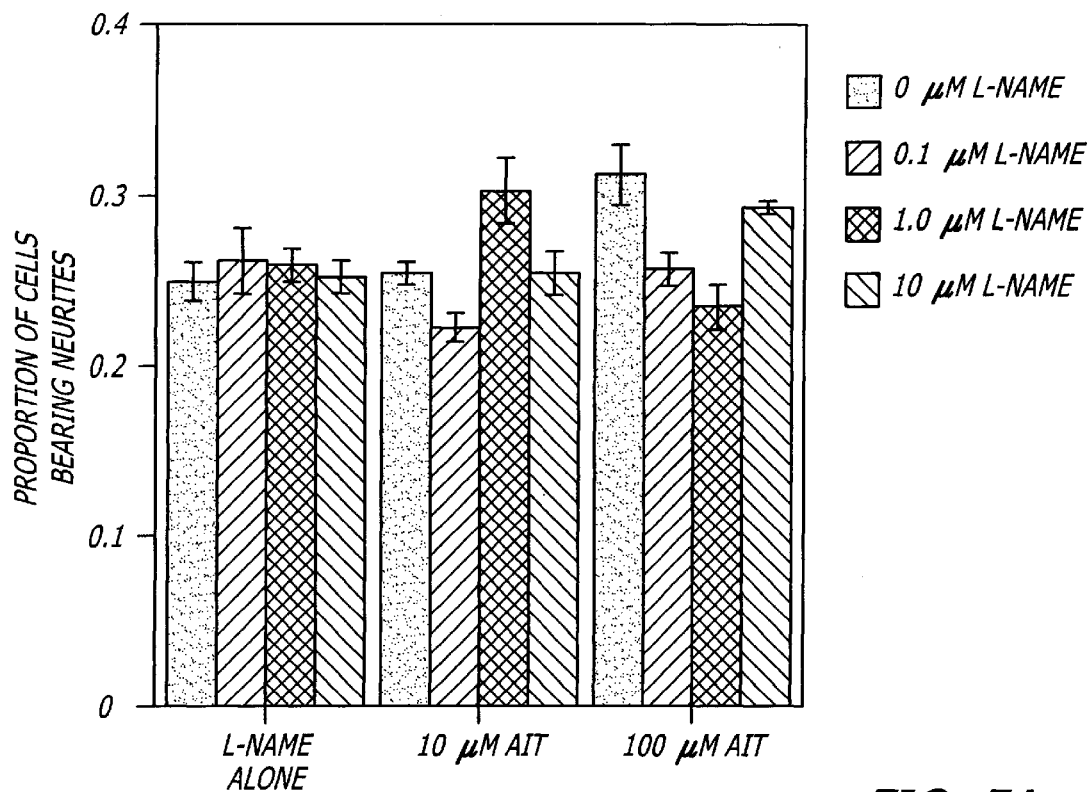
FIGS. 5A and 5B are graphical comparisons of nerve growth factor mediated neuritogenic response for cells grown in the presence of the purine derivative AIT-082 and various concentrations of nitric oxide inhibitors.
Figure 5B:
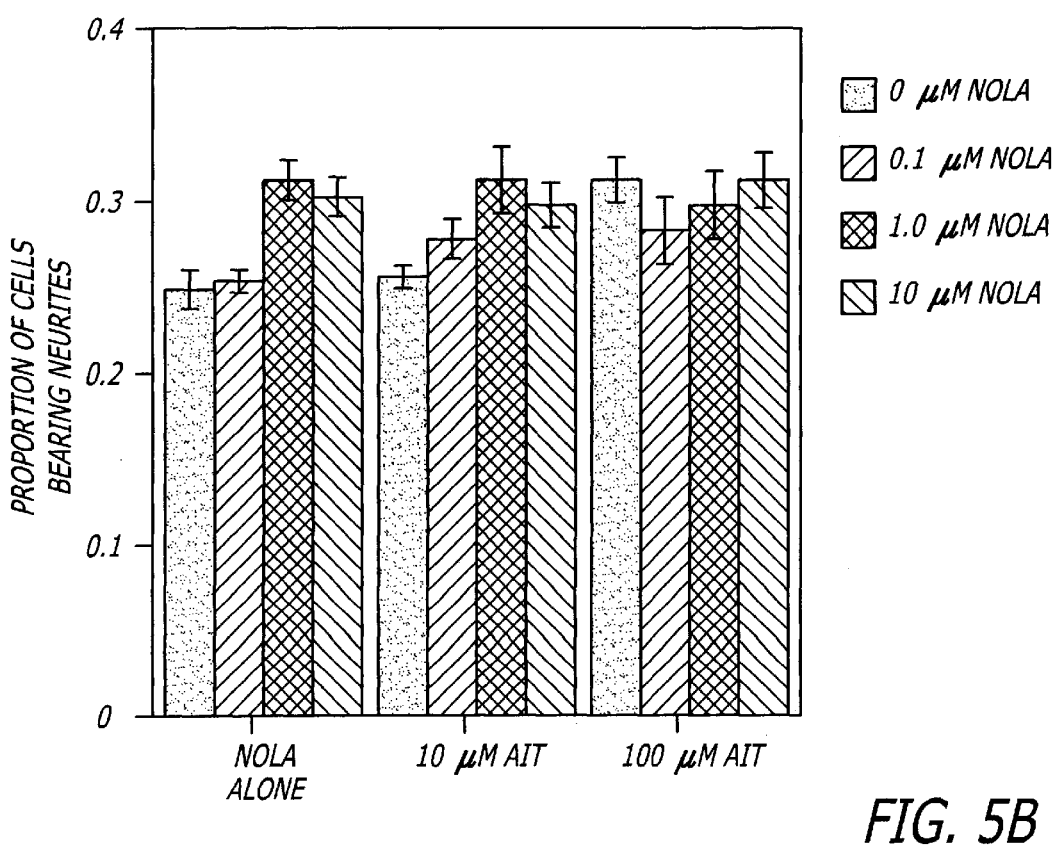

Nitric oxide is produced by the action of the enzyme nitric oxide synthetase (NOS). Two chemicals that have been shown to selectively inhibit NOS are N-nitro-L-arginine methyl ester (L-NAME) and N-nitro-L-arginine (NOLA). Different levels of these chemicals were administered simultaneously with AIT-082 and neuritogenesis in PC12 was measured using the protocol of Example 12. The results for L-NAME are presented in Table E while the results for NOLA are presented in Table F. Both tables are shown directly below with graphical representations of the data presented in FIGS. 5A and 5B.

TABLE E

The Effect of L-NAME on Neuritogenesis

| AIT-082 | Concentration of L-NAME ($\mu$M) | | | |
|---|---|---|---|---|
| | None | 0.1 | 1.0 | 10.0 |
| 0 | 0.246 ± 0.017 | 0.259 ± 0.027 | 0.257 ± 0.013 | 0.251 ± 0.013 |
| 10 $\mu$M | 0.254 ± 0.008 | 0.220 ± 0.010 | 0.302 ± 0.027 | 0.254 ± 0.018 |
| 100 $\mu$M | 0.309 ± 0.027 | 0.257 ± 0.016 | 0.232 ± 0.019 | 0.289 ± 0.006 |

TABLE F

The Effect of NOLA on Neuritogenesis

| AIT-082 | Concentration of NOLA ($\mu$M) | | | |
|---|---|---|---|---|
| | None | 0.1 | 1.0 | 10.0 |
| 0 | 0.246 ± 0.017 | 0.259 ± 0.009 | 0.311 ± 0.016 | 0.305 ± 0.017 |
| 10 $\mu$M | 0.254 ± 0.008 | 0.277 ± 0.016 | 0.312 ± 0.029 | 0.298 ± 0.019 |
| 100 $\mu$M | 0.309 ± 0.027 | 0.279 ± 0.027 | 0.295 ± 0.028 | 0.310 ± 0.023 |

As shown by the data in Tables E and F, neither of these inhibitors of NOS was effective in blocking the effect of AIT-082 on neuritogenesis. These results indicate that NO was not involved in the mechanism of action of AIT-082.

EXAMPLE 15

Effect of AIT-082 on cGMP Levels in PC-12 Cells

To demonstrate CO-dependent guanylyl cyclase modification, cyclic guanosine monophosphate (cGMP) levels in PC12 cells were measured following addition of AIT-82. Initially, PC-12 cells were primed with 40 ng/ml NGF for 3 days in low serum medium (1.5% horse serum+ 5% fetal calf serum). Cells were seeded onto assay plates in low serum medium containing 40 ng/ml NGF and incubated for 1 hour. The medium was changed to low arginine medium (80 $\mu$M) with no serum and NGF and papaverine (100 mM) where indicated. Test compounds were added for the indicated time and the reaction was stopped by adding 5% TCA containing 10,000 dpm of $^3$H-cGMP. cGMP was assayed by the radioimmunoassay method of Maurice (*Mol. Pharmacol.* 37: 671–681, 1990). TCA was purified by adding powdered charcoal (5 g) and filtering the mixture through Whatman #1 paper. This removed contaminants in the TCA that otherwise interfere with the radioimmunoassay (RIA) of cGMP.

It was necessary to purify the cGMP from cAMP and other contaminants before radioimmunoassay since these other materials can interfere with the assay. Briefly, the TCA solution was applied to Dowex columns (50W-8X, 200–400 mesh) and eluted. A neutral alumina column was then placed under each Dowex column. The cGMP was eluted from the Dowex columns into neutral alumina columns by adding 4 mL of 0.05 M HCl to each Dowex column. The neutral alumina columns were then sequentially rinsed with 2 ml of HCl, 4 mL water and finally with 0.2 M sodium acetate (pH 6.2). The cGMP collected for the RIA eluted in 1 ML of sodium acetate with a recovery between 50–65%. The cGMP was assayed using a Dupont RIA kit. The results are graphically presented in FIG. 6.

Figure 6:
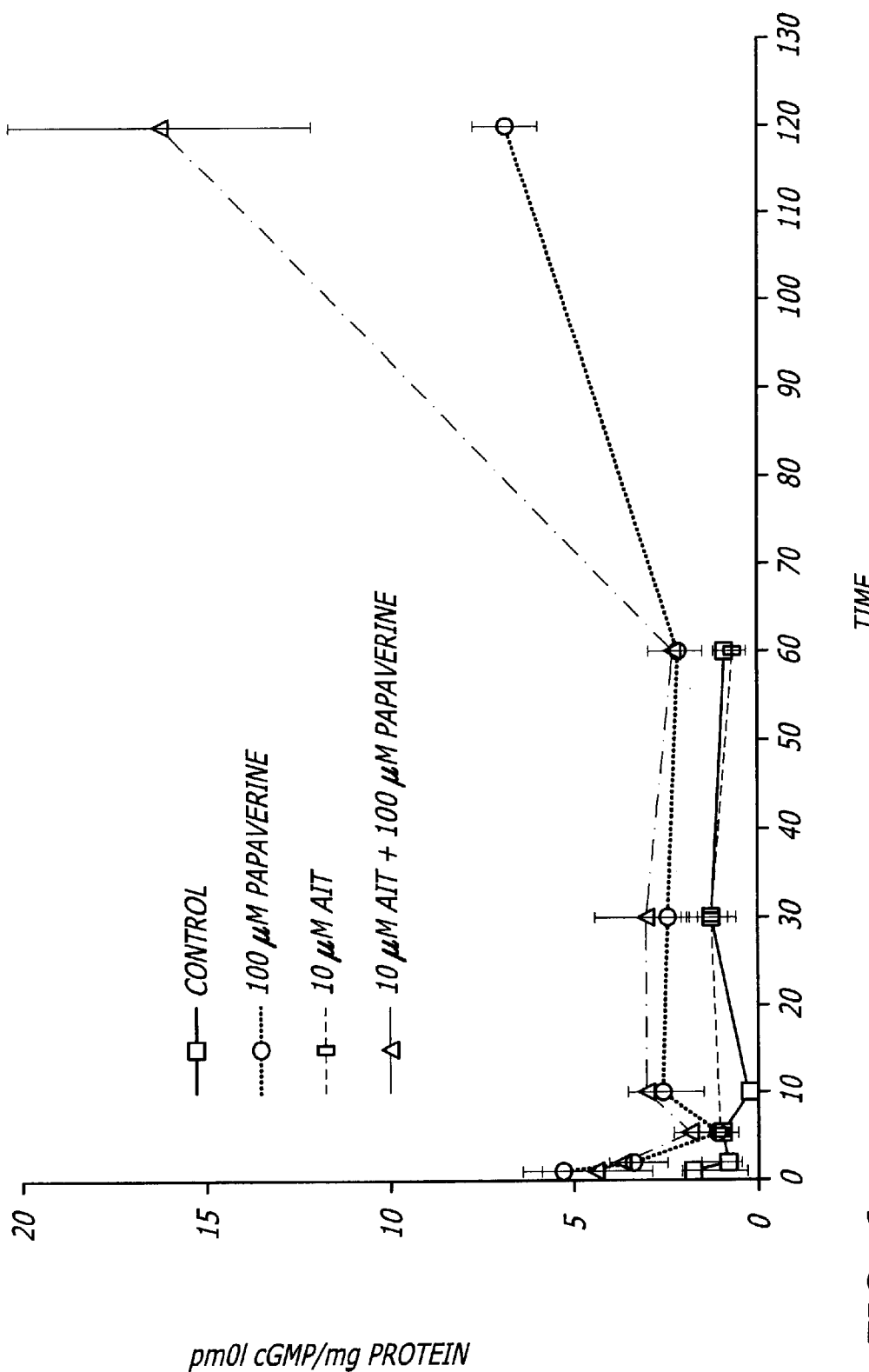
FIG. 6 is a graphical comparison of cyclic GMP production in neuronal cells grown in culture with the purine derivative AIT-082 and without AIT-082.

As shown in FIG. 6, the addition of AIT-082 increased the production of cGMP in PC12 cells indicating that AIT-082 acts by modifying the activity of the carbon monoxide-dependent enzyme guanylyl cyclase.

EXAMPLE 16

Effect of AIT-082 on Genetic Expression of Neurotrophin mRNA

To demonstrate that AIT-082 induced the in vivo genetic expression and resultant cellular production of neurotrophins, naturally occurring, genetically encoded molecules, as well as enhancing their activity, the following experiment was performed. Induction of neurotrophin mRNA was determined by northern blot analysis of astrocytes cultured with AIT-082, NGF, or both. The cells were harvested and RNA extracted at 24 hours after treatment.

More particularly, astrocytes from the cerebral cortex of NIH Swiss mice (Harlan) were isolated. Briefly, newborn pups (0–24 hours) were decapitated. Their brains were removed under aseptic conditions and were placed in modified Dulbecco's medium (DMEM) containing 20% heat-inactivated horse serum (Hyclone) ("complete medium"). The neopallium was then dissected from each cerebral hemisphere and minced into 1 mm cubes.

The astrocytes were then isolated by mechanical dissociation. The cubes were vortexed at maximum speed for one minute. The cell suspension was then passed first through 75 mm Nitex then through 10 mm Nitex. The resulting cell suspension was diluted in complete medium to a final concentration of one brain per 10 ml of complete medium. Ten milliliters of the diluted cell suspension was added to each 100 mm Falcon tissue culture plate (Fisher). After 3 days the medium was replaced with 10 ml fresh complete medium and subsequently was replaced twice weekly with DMEM containing 10% heat inactivated horse serum ("growth medium"). After two weeks in culture the astrocytes formed a confluent monolayer.

For RNA extraction, astrocytes were trypsinized. The astrocytes were then replated onto 100 mm PORN coated plates at a cell density of $10^6$ cells per plate (10 ml growth medium). After 2 hrs PBS, guanosine (Guo), or GTP at 10 mM were added to the appropriate plates. Total RNA was harvested from $1.5 \times 10^7$ cells for each treatment, 4 and 24 hrs after treatment using TRIzol reagent and supplier protocol (GIBCO BRL/Life Technologies, Inc.). For slot blots, total RNA was bound to Hybond-N filters (Amersham/United States Biochemicals) as described in *Transfer and Immobilization of Nucleic Acids and Proteins to S & S Solid Supports* (S and S Protocols: Schleicher & Schuell, New Hampshire, USA). Northern blots were also performed using 10–20 mg total RNA from each sample. These were electrophoresed in 1% agarose gels containing formaldehyde and blotted onto Hybond-N filters according to S and S protocols.

The blots were probed with $^{32}$P-labeled cDNA (NGF, NT-3 and BDNF probes) or oligonucleotide probe (FGF-2) by hybridization in Piperazine-N,N'-bis-(2-ethanesulfonic acid) (PIPES) buffer (50 mM PIPES, pH 6.8; 50 mM NaH$_2$PO$_4$; 0.1 M NaCl; 5% SDS and 1 mM EDTA) overnight at 50° C. The blots were then washed twice with (2×SSC, 0.1% SDS) wash buffer at room temperature for 20 minutes each, and then with (0.1×SSC, 0.1% SDS) wash buffer twice at 52° C. for 20 minutes each. 1×SSC is 0.15 M NaCl and 15 mM sodium citrate, pH 7.0. Damp membranes were wrapped in Saran wrap and autoradiography was performed using Hyperfilm-MP (Amersham/USB) and a cassette with intensifying screens. Various concentrations (0.25 to 4 mg of total RNA), as determined by spectrophotometry, of each sample were blotted and probed so that quantification could be done after insuring a linear film response. Quantification was performed using MCID Image Analysis (St. Catherine's, Ontario, Canada).

To provide probes, a cDNA clone of the mouse NGF gene in the plasmid pGEM.NGF(+), and cDNA clones of human NT-3 and BDNF in Bluescript were isolated. After isolation, the cDNA probes were labeled with $^{32}$P-dCTP (ICN Biomedicals Canada, Ltd.) using a Random Primed DNA Labeling Kit (Boehringer Mannheim Biochemica) as described in the kit.

A 40-mer antisense oligonucleotide was synthesized (MOBIX, McMaster University) as a probe for FGF-2. This was complementary to the 5' end of mouse FGF-2 coding sequence on the mRNA. The oligo was 5' end-labeled using polynucleotide kinase, One-Phor-All buffer, and the protocol supplied by Pharmacia Biotech Inc., and ATPgP32 (ICN Biomedicals Canada, Ltd.).

The results of the study for the production of four different neurotrophic factors are shown below in Table G.

TABLE G

Northern Blot Analysis of Neurotrophin mRNAs from Astrocytes

| Neurotrophin mRNA | Control | NGF 40 ng/ml | AIT-082 100 mM | AIT-082 (100 mM) + NGF (40 ng/ml) |
|---|---|---|---|---|
| NGF | – | – | ++ | + |
| FGF-2 | + | – | ++ | + |
| BDNF | + | + | + | + |
| NT-3 | – | – | ++ | + |

The conditions which produced a detectable amount of each of the neurotrophin mRNAs are indicated by a "+", with a "++" indicating that at least twice the detectable amount was present. Those blots which were negative are indicated by a "–".

The results indicate that AIT-082 induced the expression of mRNAs for several neurotrophic factors, including NGF. More importantly, these data clearly establish that AIT-082 selectively and controllably induced the in vivo genetic expression of at least one naturally occurring genetically encoded molecule in a mammal treated in accordance with the teachings of the present invention. Administering this exemplary purine derivative selectively induced the expression of mRNA encoding three of the four identified neurotrophic factors, NGF, FGF-2, and NT-3, but did not induce activation or derepression of the gene encoding for BDNF mRNA. This selective control coupled with the ease of administration provided by the compounds and methods o the present invention effectively overcomes the limitations of the prior art. Rather than administering these molecular compounds directly to cells through complex and potentially dangerous techniques, the present invention is able to treat a mammalian patient utilizing traditional, noninvasive drug delivery routes that induce the treated cells to express the genetic material encoding the desired compounds resulting in their direct in vivo delivery and administration. Though potentially useful in conjunction with modified genes or other molecular biology techniques, with the present invention, genetic modification is unnecessary.

It has been shown previously that, within the hippocampus from Alzheimer's patients, there is an altered program of gene expression leading to aberrant levels of mRNA for neurotrophic factors. A number of animal and clinical studies have demonstrated that administration of single neurotrophins are inadequate to treat neurodegenerative disease. Accordingly, the ability of the compounds of the present invention to stimulate the production of multiple neurotrophin mRNAs within cells substantially increases their potential as treatments for a variety of neurodegenerative diseases by providing a method for the effective direct administration of these naturally occurring genetically encoded molecules to a patient through the induction of their in vivo genetic expression.

The preceding examples show that AIT-082 stimulates neuritogenesis in vitro in PC12 cells alone and enhances the effect of nerve growth factor (NGF). Further, the neuritogenic effect of AIT-082 was reduced by methemoglobin (which captures and removes nitric oxide and carbon monoxide), methylene blue (which inhibits guanylyl cyclase), and by zinc protoporphyrin IX (an inhibitor of heme oxygenase 2, which produces carbon monoxide). The neuritogenic effect of AIT-082 was unaffected by L-NAME or NOLA, inhibitors of NO production. In addition, AIT-082 stimulated the production of a number of different neurotrophic factors as evidenced by increased mRNA levels of these factors in astrocytes after AIT-082 administration in vitro. Moreover, since AIT-082 is orally active and rapidly passes the blood-brain barrier as shown in Example 2, it has significant therapeutic potential as an NGF-mimetic agent in Alzheimer's disease and in other neurodegenerative diseases.

In view of the previous results, studies were performed to demonstrate the effectiveness of using AIT-082 to treat neurodegenerative diseases. Loss of memory represents the core symptom of Alzheimer's disease as it does in a number of other neural afflictions. Specifically working (or episodic) memory is impaired in Alzheimer's disease, amnesia, aging and after hippocampal lesions in monkeys. The effects of AIT-082 in ameliorating this memory loss was used to demonstrate the efficacy of the compounds of the present invention with respect to the treatment of neurodegenerative diseases.

EXAMPLE 17

Comparison of Memory Trace in Different Mice Strains

The win-shift T-maze paradigm has been shown to specifically model working memory in rodents and is a widely accepted method. The rodent's natural behavior is to forage for food when hungry and therefore it will not return to the same location after it has consumed any food that was present. This model was not designed to account for all of the vast data on memory. Data from hypoxia and ischemia studies, procedures which selectively damage CA1 hippocampal cells, produce deficits in working memory while other types of memory are not affected. This strongly suggest that there are several types of memories which have different anatomical sites and most likely different neurochemical inputs. Accordingly, while the win-shift model may not account for all neurochemical inputs involved in working memory, the model does provide a useful art accepted tool in designing pharmacological experiments to provide information on the mechanism by which memory can be modified.

Male Swiss Webster mice six months (young adult) and eleven months (old) of age, obtained from the National Institute on Aging, were maintained in individual cages, on a 22 hour light/dark cycle with continuous access to water. Food was limited so that the mice stabilized at 80% of free feeding weight. Mice were weighed and handled daily for one week. The win-shift model was run as described in the literature and consists of a T-maze in which the correct response alternates after each correct trial. The interval between trials is varied and allows for the determination of the longest period between trials that a subject can remember the correct response on the previous trial. This allows the measure of the duration of the memory trace. A score of 5 (5 correct responses per 10 trials, 50% correct) is considered chance; that is, the animal does not remember which box it selected for positive reward on the previous trial. The reward goal box is alternated after each correct trial. Ten trials per mouse are run each day. If the animal establishes a spatial learning set (right side only), they would return to the same goal each trial and have a correct response rate of significantly less than 50% correct. The latency time to leave the start box is recorded as a measure of motivation, the running time (the time from leaving the start box to reaching the goal box) is recorded as a measure of performance, and the number of correct responses as a measure of memory.

The data in Table H illustrate the effect of increasing the inter-trial interval in young adult mice without any drug treatment.

TABLE H

Effect of Inter-Trial Interval in Win-Shift Paradigm[1]

| | Inter-Trial Interval (Seconds) | | | | |
|---|---|---|---|---|---|
| | 30 | 60 | 90 | 120 | 150 |
| Swiss Webster mice | 7.5* | 7.5* | 5.0 | | |
| C57BL/6 mice | 7.0* | 7.4* | 7.0* | 7.8 | 5.6 |

[1]Score is the mean number of correct responses per 10 trials. Saline was administered 1 hour prior to testing.
*$p < 0.05$. Data analysis following significant ANOVA, a Dunnett test was run comparing drug tested groups with controls. An Arc Sign transformation was performed on percentage data.

From the data in Table H, it can be seen that Swiss Webster mice are capable of remembering the win-shift strategy when the inter-trial delay interval is 30 or 60 seconds. Few mice with saline treatment scored above chance (50%) with the 90-second inter-trial delay interval. These data indicate that the "memory trace" in these animals disappears between 60 and 90 seconds All drug evaluation tests in normal adult Swiss Webster mice were conducted with the 90-second inter-trial interval except where indicated otherwise. In C57BL/6 mice, the duration of the memory trace was 120 seconds.

EXAMPLE 18

Effect of AIT-082 on Memory Trace Duration

The activity of AIT-082 was compared with tacrine (THA) and physostigmine (PHY), experimental anticholinesterase agents which enhance memory in animals. The drugs were also evaluated for their effects on locomotor activity. In the win-shift memory paradigm, AIT-082 was evaluated for its ability to induce tolerance after 18 days of drug administration. In addition AIT-082 was tested for its activity to modify learning in a modified T-maze discrimination task.

The drugs used in this example are 4-((3-(1,6-dihydro-6-oxo-9-purin-9-yl)-1-oxopropyl)amino) benzoic acid (AIT-082), as an exemplary potassium salt, tacrine hydrochloride (tetrahydroaminoacridine, THA, Sigma Chemical Co., St. Louis, Mo.), and physostigmine, hemisulfate salt (PHY, Sigma Chemical Co., St. Louis, Mo.). The drugs were dissolved in saline and prepared fresh daily. All injections were made at a volume of 0.1 ml/10 grams body weight. When testing drug effects, intraperitoneal (i.p.) injections of AIT-082 or THA were made one hour prior to the start of testing. Due to its shorter duration of action, PHY was injected 30 minutes prior to testing. Control subjects receive a similar injection of saline (vehicle).

To determine the duration of the memory trace, subjects were administered drug or saline and 30 minutes (PHY) or 1 hour (AIT-082 or THA) later they were given a single reference run with the milk reward in both goal boxes. After the indicated inter-trial delay, subjects were returned to the start box and given the first test trial with the milk reward only in the goal box opposite to the one entered on the previous correct trial. The subjects were given 10 trials with the reward alternating only after correct responses.

To determine if tolerance to the biological effects of AIT-082 developed, drug or saline was administered daily for 18 days prior to the testing in the standard win-shift paradigm.

Subjects were also trained in the same T-maze used for the win-shift model discussed above. As in the win-shift method, subjects were shaped and then given a single reference run in which reward was available in both goal boxes. The subject was only allowed to consume the milk reward in the goal box selected. On the next run, the reward and thus the correct response was in the same goal box selected for the reference run and was not alternated. The subject was required to learn that there was no shift in the goal box for the correct response. The subjects were given 10 trials per day and continued until the subject had at least 8 out of 10 correct responses on two consecutive days. The number of days to reach this criteria of performance was recorded. After the subject reached criteria, the goal box for the correct response was reversed. The number of days taken to reach criteria on reversal was recorded.

The results of the T-maze learning task and win-shift memory test are presented in Table I directly below.

TABLE I

Effect of AIT-082, THA and PHY at 90-Second Inter-Trial Interval in Swiss Webster Mice

| Type of Test[1] | Control | THA | AIT-082 Dosage (mg/kg) | | PHY |
|---|---|---|---|---|---|
| | Saline | 1.25 | 0.5 | 30.0 | 0.125 |
| Win-shift Memory Test | | | | | |
| Correct responses (Correct responses/10 trials) | 4.6 | 7.1* | 6.5* | 8.2* | 6.5 |
| Latency time (seconds) | 2.68 | 8.22* | 1.95 | 2.03 | |
| Running time (seconds) | 1.95 | 3.65* | 2.20 | 1.95 | 2.65 |
| Locomotor Activity[2] | 343 | 671* | 323 | 378 | N/T |
| T-maze Learning (days to reach criteria) | | | | | |
| Learning | 3.6 | N/T[3] | 3.0 | 3.3 | N/T |
| Reversal | 4.2 | N/T | 3.78 | 3.5 | N/T |
| Tolerance (Correct responses/10 trials) | 4.9 | N/T | N/T | 7.6* | N/T |

[1]at least 8 animals were run per group.
[2]Spontaneous movements per hour.
[3]Not tested.
*Indicates p < 0.05. Data analysis following significant ANOVA, a Dunnett test was run comparing drug tested groups with controls. An Arc Sine transformation was performed on percentage data and latencies were transformed to reciprocal time scores or speed scores.

As can be seen from the data in Table I, AIT-082 treatment resulted in an increased number of correct responses (memory) compared to saline control. While the effect was in the same range as with THA and PHY, both THA and PHY also increased latency time (prolonged the time to leave the start box, evidencing decreased motivation) and THA increased spontaneous locomotor activity. AIT-082 had no effect on learning or reversal and no tolerance developed to the memory enhancing effect of AIT-082 after 18 days of pre-treatment. Only AIT-082 enhanced memory function without affecting learning, motivation, performance and locomotor activity. Similar data have been observed with oral administration of AIT-082.

EXAMPLE 19

Effect of AIT-082 Dosage on Memory Trace Duration

Figure 7:
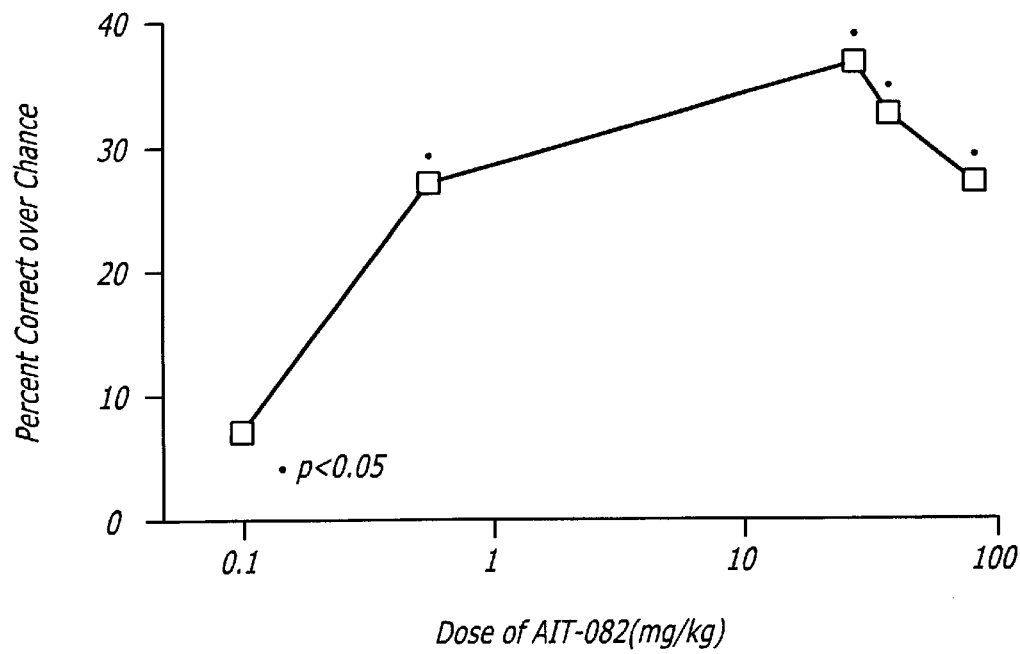
FIG. 7 is a graphical representation of the effects of different doses of the purine derivative AIT-082 on learning as measured in Swiss Webster mice using a win-shift memory test.
Figure 8:
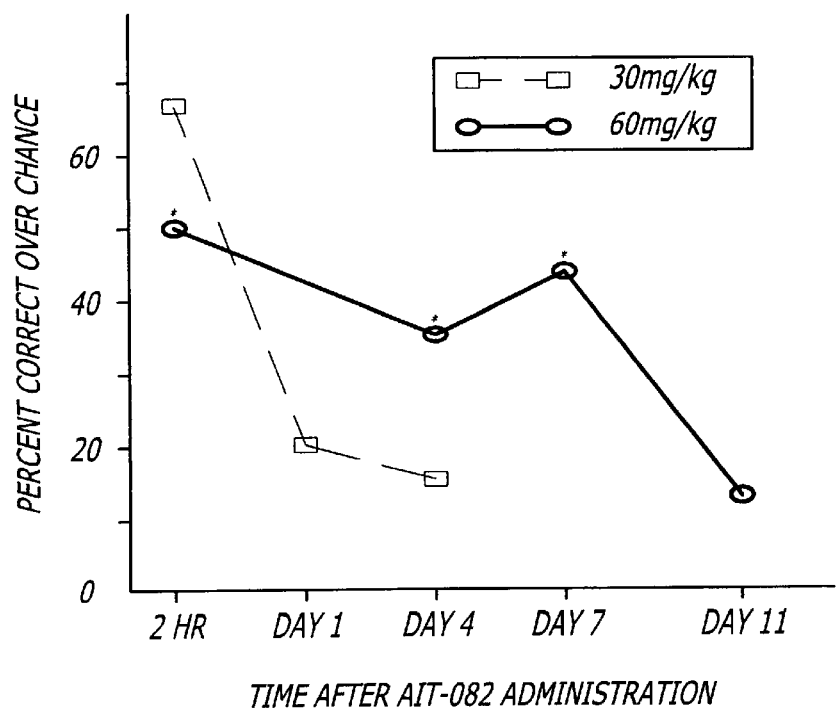
FIG. 8 is a graphical comparison of the duration of action of the purine derivative AIT-082 measured over time for single doses of 60 mg/kg and 30 mg/kg.

The dose response and duration of action of AIT-082 was studied in young adult Swiss Webster mice. The results are presented as the percent correct response over chance; chance being 50% correct. As shown in FIG. 7, AIT-082 is active in improving memory in normal adult Swiss Webster mice over a dose range from 0.5 to 60 mg/kg, with the optimal effect at 20 to 30 mg/kg. Further, as shown in FIG. 8, the onset of action is rapid (1 hour, data not shown) and lasts for more than seven days after a single dose of 60 mg/kg. Those skilled in the art will appreciate that the extended duration of the drug's effects will substantially lower the frequency of administration providing benefits in terms of patient compliance and cost.

EXAMPLE 20

Effect of AIT-082 on Memory Trace Duration in C57BL/6 Mice

Previous work has established that normal adult Swiss Webster mice have a memory trace duration of 60 seconds in the win-shift paradigm which may be increased by the administration of AIT-082. In order to further demonstrate the applicability and operability of the methods and compositions of the present invention, an alternative strain of mice having a different duration of memory trace was administered AIT-082, using the preceding protocol. The results are shown in Table J directly below.

TABLE J

Duration of Memory Trace in C57BL/6 Mice

| | Treatment Groups | | | | | |
|---|---|---|---|---|---|---|
| | Control (Saline) | | AIT-082 (30 mg/kg) | | Physostigmine (0.125 mg/kg) | |
| Inter-trial interval (sec) | No. above chance/ Total # | Correct a | No. above chance/ Total# | Correct ◇ | No. above chance/ Total# | Correct a |
| 30 | 3/5 | 70 ± 11** | | | | |
| 60 | 3/5 | 70 ± 16** | | | | |
| 90 | 4/5 | 70 ± 6** | | | | |
| 120 | 4/5 | 78 ± 16** | | | | |
| 150 | 1/5 | 56 ± 10 | | | | |
| 180 | 2/7 | 58 ± 12 | 4/6 | 70 ± 15** | 3/6 | 65 ± 16* |
| 210 | | | 4/6 | 78 ± 15** | 1/6 | 53 ± 9 |
| 240 | | | 0/6 | 50 ± 6 | | |
| 270 | | | 0/6 | 50 ± 6 | | |

\# = No. subjects above chance (60% correct)/Total No. subjects tested
a = Mean score ± S.E.
** = p < 0.01 (t-test against chance)
* = p < 0.05 (t-test against chance)

Typically, in the win-shift foraging paradigm, C57BL/6 mice have a duration of memory trace of 120 seconds. As shown in Table J, at 30 mg/kg i.p., AIT-082 prolonged the duration of the memory trace to over 210 seconds. While physostigmine also prolonged the duration of the memory trace from 120 to 180 seconds in this model, it was not as active as AIT-082.

EXAMPLE 21

Treatment of Age Induced Memory Disorders using AIT-082

In light of the preceding results, studies were performed to demonstrate that AIT-082 improves memory in mammals with neuronal disorders as well as in healthy subjects. Twelve-month old male Swiss Webster mice were screened for performance in the win-shift foraging test. Subjects were tested at various time delays, beginning at 10 seconds and increasing the inter-trial time interval to 30, 60, 90 and 120 seconds. The results for untreated mice are shown in Table K directly below.

TABLE K

Age-Induced Working Memory Deficits in Swiss Webster Mice

| Duration of Memory Trace | No. of Subjects | % of Subjects | Degree of Memory Impairment |
|---|---|---|---|
| less than 10 seconds | 6 | 25 | Severe |
| 10 seconds | 8 | 33 | Moderate |
| 30 seconds | 10 | 42 | Mild |
| Total | 24 | 100 | |

The results in Table K demonstrate that individual subjects can be classified by the degree of working memory impairment. Subjects with severe impairment could not remember the correct response at 10 seconds while subjects with mild deficit could remember the correct response with a 30 second inter-trial interval but not at 60 seconds. Subjects with a moderate deficit could remember the correct response with a 10 second inter-trial interval but not 20 at 30 seconds. Thus, the win-shift model can detect age-induced impairments in working memory. As will be appreciated by those skilled in the art, this observation is important since it provides the ability to use age-matched subjects with varying degrees of impairment for evaluation of potential therapeutic agents.

Figure 9:
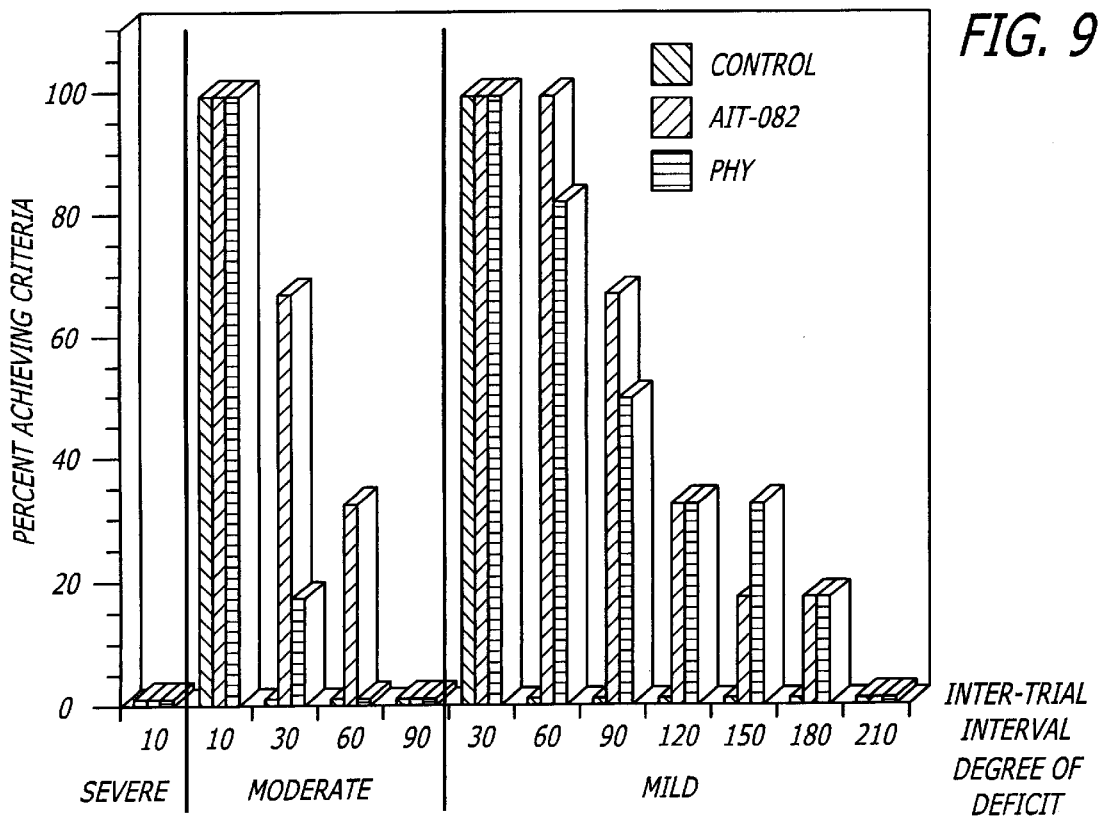
FIG. 9 is a graphical comparison of learning abilities of age-induced memory deficit Swiss Webster mice treated with the purine derivative AIT-082 and the drug physostigmine.

Following the establishment of a baseline, six subjects in each of the three groups were treated with AIT-82 (30 mg/kg, one hour before testing) or physostigmine (0.125 mg/kg, 30 minutes before testing) using the win-shift foraging test. The results are presented in Table L directly below and graphically represented in FIG. 9.

TABLE L

Effect of AIT-082 and PHY on the Duration of Memory Trace in Swiss Webster Mice with Age-Induced Deficits

| Degree of Deficit | Inter-trial Interval (sec) | Control (Saline) | AIT-082 30 mg/kg | PHY 0.125 mg/kg |
|---|---|---|---|---|
| Mild | 60 | 0/6 | 6/6* | 5/6* |
| | 90 | | 4/6 | 3/6 |
| | 120 | | 2/6 | 2/6 |
| | 150 | | 1/6 | 2/6 |
| | 180 | | 1/6 | 1/6 |
| | 210 | | 0/6 | 0/6 |
| Moderate | 30 | 0/6 | 4/6* | 1/6 |
| | 60 | | 2/6 | 0/6 |
| | 90 | | 0/6 | |
| Severe | <10 | 0/6 | 0/6 | 0/6 |

Data is presented as the number of subjects performing significantly above chance/total number of subjects;
*Indicates $p < 0.05$ (t-test)

Six subjects had a severe deficit with no memory trace, they could not remember the task at 10 seconds. None of these subjects showed memory restoration with either AIT-082 or PHY treatment. In the six subjects with a moderate memory deficit who had a duration of memory trace of 10 seconds, AIT-082 increased the duration of the memory trace to greater than 30 seconds in 4 subjects (67% of the subjects) and increased the memory trace to greater than 60 seconds in two subjects (50%). In the six subjects with a mild memory deficit who had a duration of memory trace of 30 seconds, AIT-082 increased the duration of the memory trace in 2 subjects to 60 seconds, in 2 subjects to 90 seconds and in one subject each to 120 and 180 seconds. PHY increased the duration of the memory trace from 10 seconds to 30 seconds in only one animal in the moderate deficit group. In the mild deficit group, PHY increased the duration of the memory trace in 2 subjects to 60 seconds, in one subject to 90 seconds and in two subjects to at least 180 seconds. Thus, AIT-082 is more active than physostigmine in the moderate deficit group and at least as active in the mild deficit group.

EXAMPLE 22

Treatment of Age Deficit Memory Disorders using AIT-082

Figure 10:
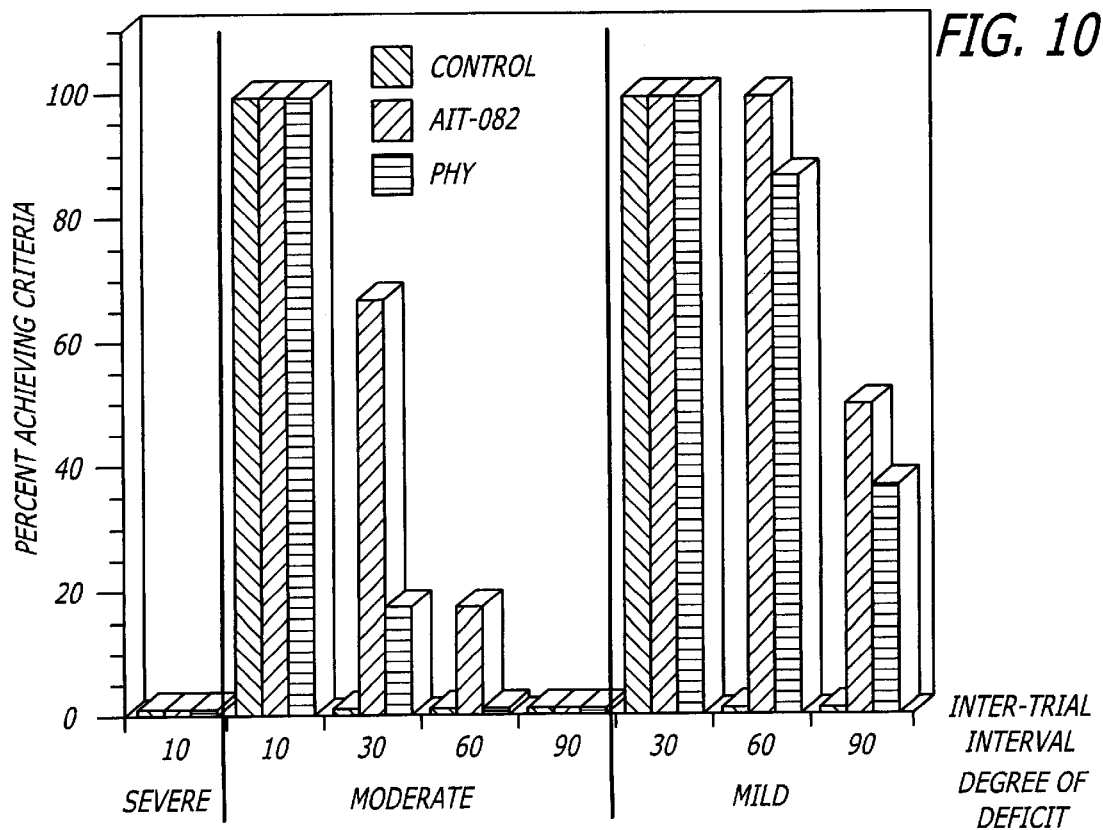
FIG. 10 is a graphical comparison of learning abilities of age-induced memory deficit C57BL/6 mice treated with the purine derivative AIT-082 and the drug physostigmine.

Twelve-month old male C57BL/6 mice were screened for performance in the win-shift foraging test. Subjects were tested at various inter-trial time intervals. Subjects who could not perform to criteria (>60% correct) at 10 seconds delay were classified as having a severe deficit. Subjects who performed to criteria at 10 seconds but not at 30 seconds were classified as having a moderate degree of deficit and subjects who performed to criteria at 30 seconds but not at 60 seconds were classified as having mild deficit. As in Example 21, subjects in each group were treated with either AIT-082 or PHY to determine the extent to which the working memory trace was prolonged. The results are presented in Table M directly below and graphically represented in FIG. 10.

TABLE M

Effect of AIT-082 and PHY on the Duration of Memory Trace in C57BL/6 Mice with Age-Induced Deficits

| Degree of Deficit | Inter-trial Interval (sec) | Control (Saline) | AIT-082 30 mg/kg | PHY 0.125 mg/kg |
|---|---|---|---|---|
| Mild | 60 | 0/6 | 4/4* | 7/8* |
|  | 90 |  | 2/4* | 3/8 |
|  | 120 |  |  | 2/8 |
|  | 150 |  |  | 2/8 |
|  | 180 |  |  | 2/8 |
|  | 210 |  |  | 0/8 |
| Moderate | 10 | 6/6 | 6/6* | 6/6 |
|  | 30 | 0/6 | 4/6 | 1/6 |
|  | 60 |  | 1/6 | 0/6 |
|  | 90 |  | 0/6 |  |
| Severe | <10 | 0/6 | 0/6 | 0/6 |

Data is presented as the number of subjects performing significantly above chance/total number of subjects;
*Indicates p < 0.05 (t-test)

In the mild deficit group, AIT-082 prolonged the duration of the memory trace from 30 to 90 seconds, from 10 to 30 seconds in the moderate deficit group. While PHY prolonged memory in the mild group, it was ineffective in the moderate group. Therefore AIT-082 restored working memory deficits in both normal mice and mice with age induced neronal disorder for both Swiss Webster and C57BL/6 strains. Specifically, the results show the AIT-082 restores working memory in mice with mild and moderate memory deficits. Based on the other Examples previously provided it is reasonable to conclude that it accomplishes this restoration by modifying the carbon monoxide dependent guanylyl cyclase system.

EXAMPLE 23

Prophylaxis of Age Deficit Memory Disorders using AIT-082

Figure 11:
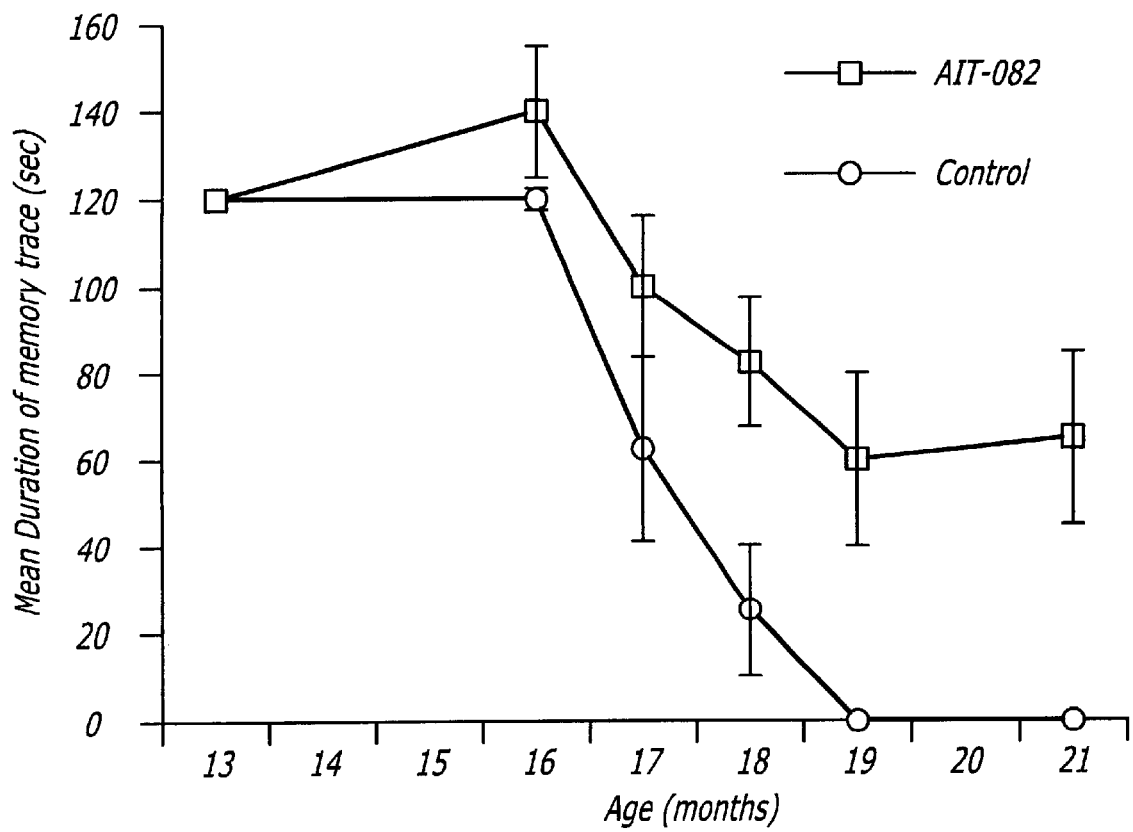
FIG. 11 is a graphical comparison of age-induced memory deficit prophylaxis in mice treated with the purine derivative AIT-082 and untreated mice.

It has been observed that age-induced memory deficits typically begin to manifest themselves in mice between 14 and 16 months of age. Therefore, the treatment of mice was begun at 14 months of age with AIT-082 (30 mg/kg/day) in their drinking water. The animals were measured monthly for their memory using the win-shift foraging tests previously described. The results are shown in FIG. 11 and show that the administration of AIT-082 delayed the onset and severity of memory deficits.

EXAMPLE 24

Prophylaxis of Alcohol-Induced Deficit Memory Disorders using AIT-82

In order to demonstrate the broad applicability of the methods of the present invention with respect to different types of neurodegenerative disorders, AIT-082 was used to retard the production of alcohol induced memory deficit. Six month old male C57BL/6 mice were evaluated in the win-shift model in combination with treatment with ethanol, a non-specific memory suppressant, and AIT-082. Subjects were treated with saline (control) or AIT-082 (30 mg/kg. i.p.) 1 hour prior to testing. Ethanol was administered at a dose of 0.5 gm/kg i.p. ten minutes prior to testing. The results of a pilot study are presented in Table N directly below.

TABLE N

Working Memory Deficit Produced by Ethanol and its Reversal by AIT-082

| | Treatment | | |
|---|---|---|---|
| | Control | Ethanol | Ethanol + AIT-082 |
| Correct trials[1,2] | 8.08 ± 0.29 | 6.5 ± 26* | 7.89 ± 0.54† |
| Latency time (sec)[2] | 1.24 ± 0.17 | 1.18 ± 0.10 | 1.77 ± 0.27 |
| Running time (sec)[2] | 1.44 ± 0.35 | 1.17 ± 0.08 | 3.22 ± 0.61*† |
| Number of subjects | 13 | 13 | 9 |

[1]Indicates mean number of correct responses per 10 trials;
[2]Indicates mean values ± S.E.;
*Indicates p < 0.05 (t-test) compared to control;
† Indicates p < 0.05 (t-test) compared to ethanol.

The results in Table N demonstrate that it is possible to identify a dose of a blocking agent that can produce a memory deficit as measured in the win-shift model. Ethanol was selected as a non-specific blocking agent and its effects were reversed by administration of AIT-082 prior to the treatment with ethanol. Therefore it would appear feasible to evaluate other more specific blocking agents which have activity at specific receptor sites.

In addition to AIT-082 other purine derivatives are believed to play a role in neuronal survival, synaptogenesis and recovery of function following injury or cell death in the central nervous system. For example, similarities between guanosine and AIT-082 indicate that AIT-082 and guanosine act through comparable mechanisms. That is, both appear to act as carbon monoxide dependent guanylyl cyclase modulators. Further, it is known that after cells are damaged, they leak massive amounts of both purine nucleosides and nucleotides to the extracellular space. The extracellular concentration of guanosine in the region of a focal brain injury may reach 50 mM and is elevated up to five fold for at least seven days. Therefore, following injury, astrocytes or glia and neurons are exposed to high extracellular concentrations of guanosine.

Accordingly, the following studies were undertaken in order to demonstrate the effectiveness of using other exemplary purine derivatives such as guanosine to modulate the carbon monoxide dependent guanylyl cyclase system.

EXAMPLE 25

Astrocytes Produce Trophic Gactors Upon Exposure to Guanosine and GTP

Astrocytes appear to proliferate in response to extracellular guanosine or guanosine triphosphate (GTP). GTP or guanosine may also stimulate the release of trophic factors from cultures of neocortical astrocytes from neonatal mouse brains. Astrocytes were incubated with different concentrations of guanosine or GTP respectively. Neurotrophin imunoreactivity in the culture medium from treated cells was then measured by ELISA.

Briefly, 96 well Falcon plates (Fisher) were coated with 1 mg/ml of sheep mono-specific anti-NGF IgG (affinity column purified) contained in 0.1M sodium carbonate buffer pH 9.6. After an overnight incubation at 4° C. blocking solution (PBS with 10% goat serum) was added to remove excess antibody. After a four hour incubation at room temperature the plates were washed three times with PBS containing 0.05% Tween 20. The conditioned media and standard 2.5S HPLC purified NGF were added and incubated overnight. The next day plates were washed 3 times with PBS-0.05% Tween 20. The secondary antibody, rabbit mono-specific anti-NGF IgG conjugated with β-galactosidase (Pierce-SPDP method) (1:500 dilution) was added. The plates were incubated overnight at 4° C. The next day the plates were washed 3 times with PBS-0.05% Tween 20. To each, well substrate, 0.2 mM 4-methylumbelliferyl-β-galactoside (MUG) in 0.1 M phosphate buffer (1 MM $MgCl_2$ pH 7.2) was added. After a 4 hour incubation at room temperature the reaction was stopped by the addition of 0.1 M glycine, pH 10.3. Samples were then read using Microfluor ELISA reader (excitation 360 nm; emission 450 nm). The sensitivity of this assay was 10 pg/well NGF.

Figure 12A:
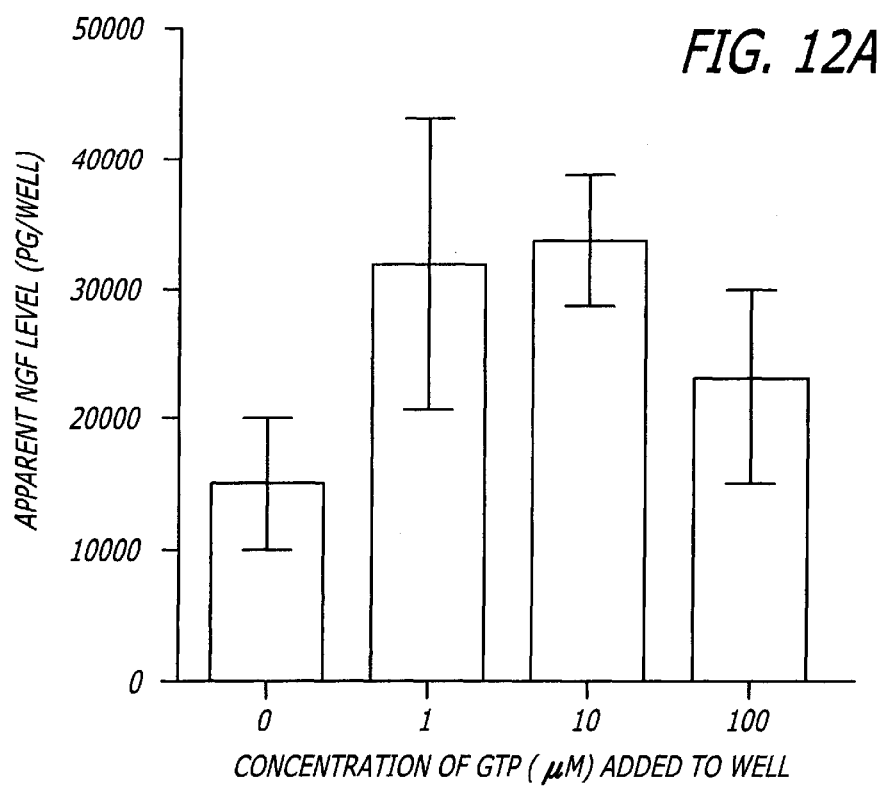
FIGS. 12A and 12B are graphical comparisons of the production of nerve growth factor by murine cortical astrocytes in response to the addition of purine derivatives as measured using an ELISA assay.
Figure 12B:
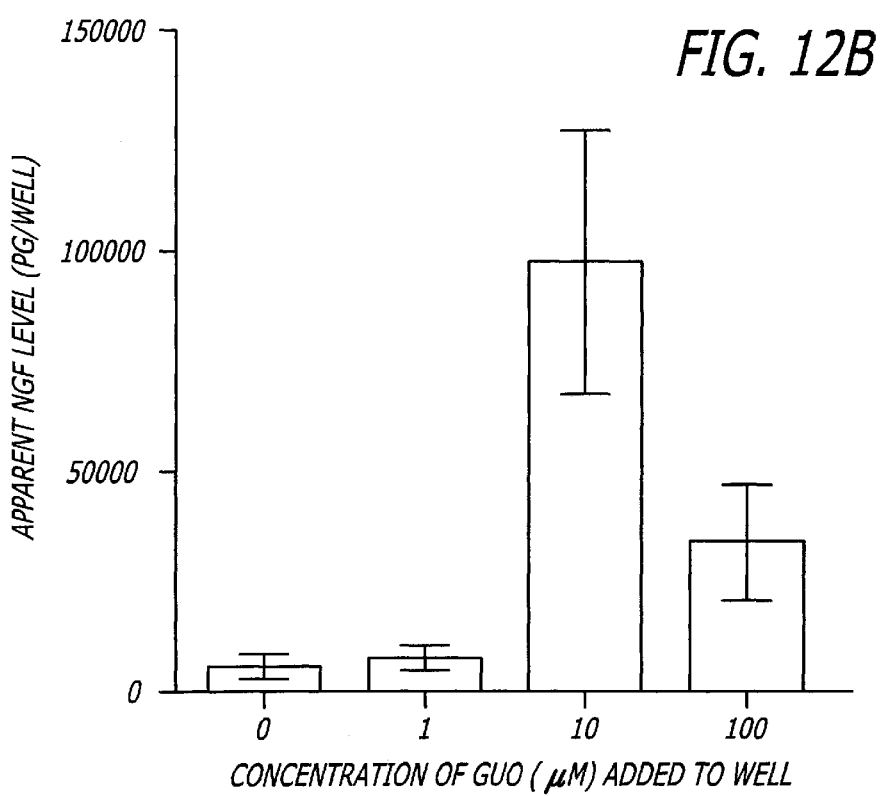

The ELISA assay detected neurotrophins NGF and NT-3 with ahnost equal affinity and BDNF with 100 times less affinity. As shown in FIGS. 12A and 12B, both guanosine and GTP increased the amount of NGF-like immunoreactivity in the culture medium. The astrocytes exposed to the various levels of guanosine produced a much stronger response than those exposed to equivalent concentrations of GTP.

EXAMPLE 26

Astrocytes Produce Neurotrophic Factors Upon Exposure to Guanosine

Figure 13A:
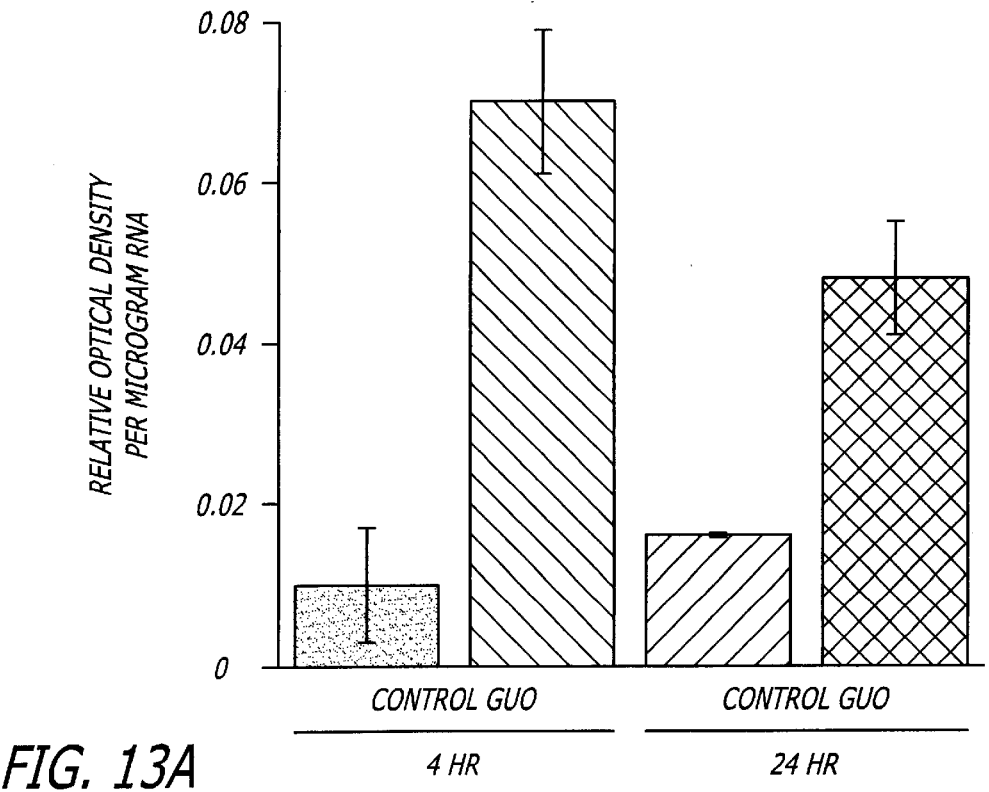
FIGS. 13A and 13B are graphical comparisons of the production of various neurotrophic factor mRNA by murine cortical astrocyte cells grown in the presence and absence of guanosine at different times.
Figure 13B:
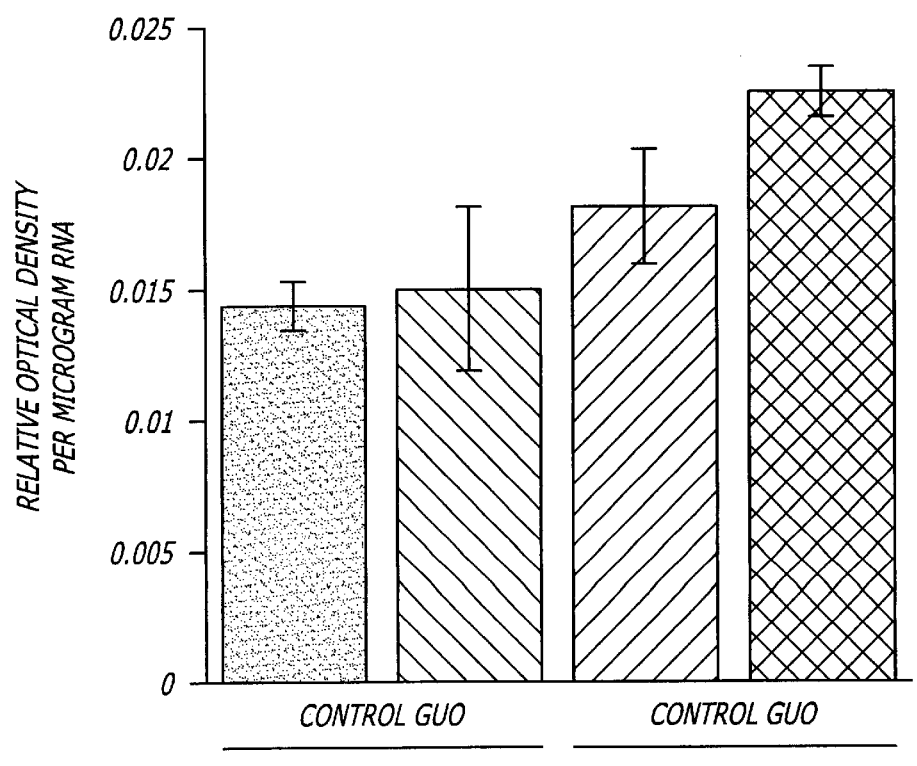

In order to confirm the results of the previous assay, mRNA levels of the tropic factors FGF-2 and NGF were measured in astrocytes which had been exposed to guanosine. The mRNA levels were measured using the same protocol used previously in Example 16. As shown in FIGS. 13A and 13B, the addition of guanosine increased NGF and FGF-2 mRNA at 4 hours and at 24 hours, respectively, after it was added to astrocytes. The observed increase in neurotrophin mRNA is important following brain injury or recovery from brain injury when the extracellular concentration of guanosine is considerably high. As cells are exposed to a high concentration of guanosine for several days following brain injury, this data indicates that guanosine may be responsible for some of the recovery of function.

As previously discussed, an agent that can penetrate the blood brain barrier and increase concentrations of neurotrophic factors as measured here by mRNA levels should have a substantial positive effect on neuronal survival and on the formation of collateral nerve circuits. In turn, this should enhance functional recovery in many different neurological diseases or after damage to the nervous system.

EXAMPLE 27

Neurons Undergo Neuritogenesis Upon Exposure to Guanosine

Figure 14A:
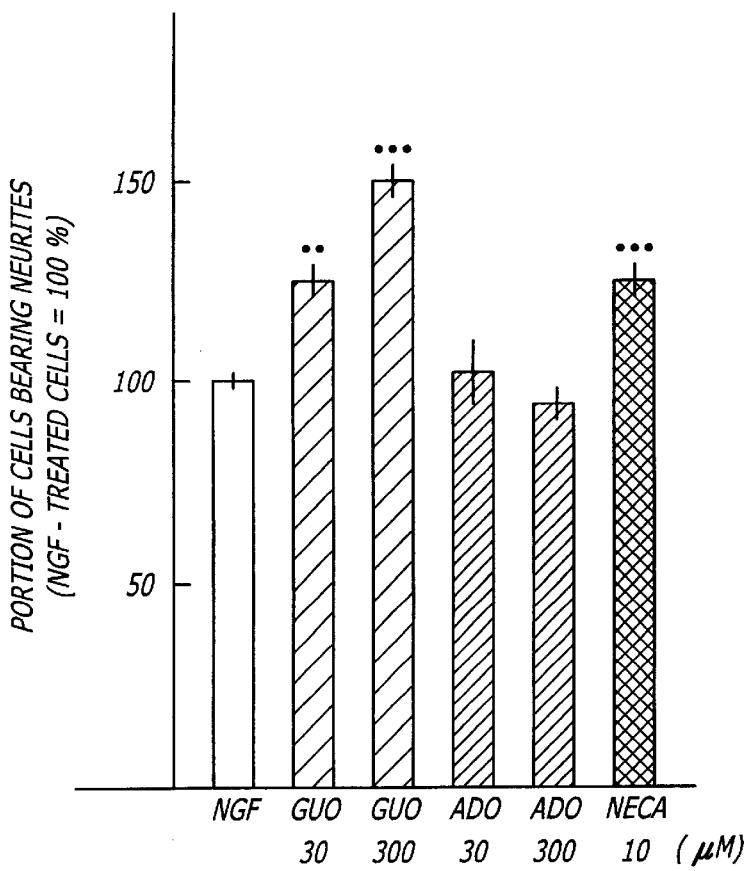
FIGS. 14A, 14B and 14C are graphical comparisons of neuritogenic responses to different concentrations of purine derivative in the presence and absence of nerve growth factor.
Figure 14B:
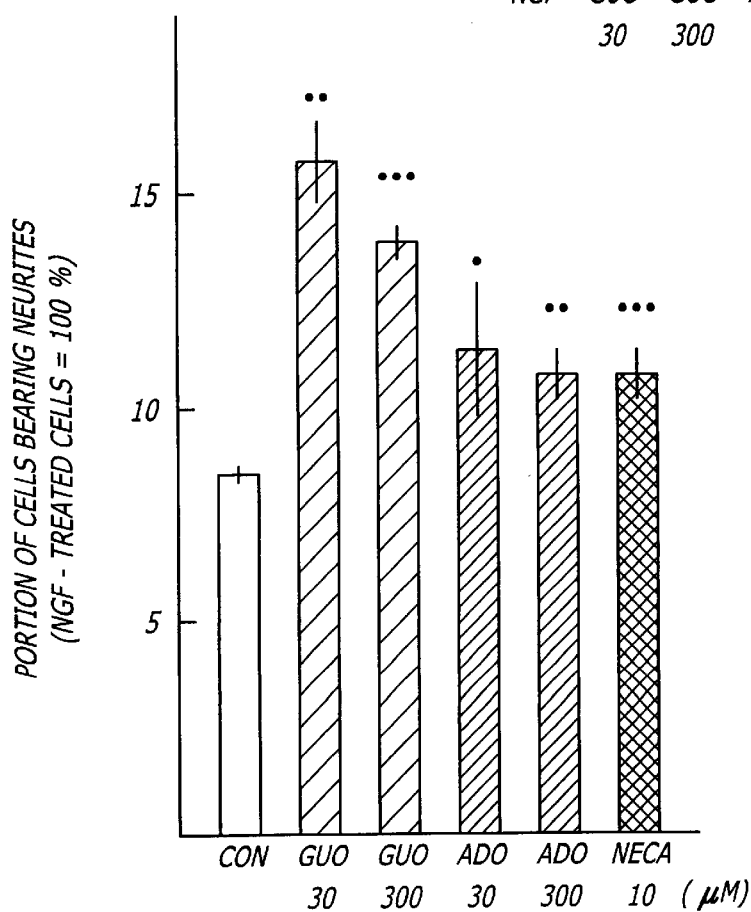

In addition to changes in glia or astrocytes, important neuronal changes also take place following focal brain injury. Neuritic processes of surviving neurons may undergo neuritogenesis. Accordingly, based on previous results using AIT-082, studies were performed to demonstrate that guanosine may also modify carbon monoxide guanylyl cyclase to stimulate neuritogenesis. As previously discussed, because PC12 cells constitute a homogeneous population of neuronal-like cells, without contaminating astroglia-type cells, the direct effects of the exemplary purine derivatives of the present invention on neurite outgrowth in these cells can be observed easily. Accordingly, PC12 cells were exposed to guanosine and adenosine with and without NGF and monitored as in Example 12. The effects of exposure to purine derivatives in the presence of NGF are shown in FIG. 14A while exposure to purine derivatives in the absence of NGF is shown in FIG. 14B. A direct comparison of the effects of these purine derivatives in the presence or absence of NGF is shown for each compound in FIG. 14C.

As shown in FIG. 14A, guanosine, but not adenosine, enhanced the neurite outgrowth induced by NGF in PC12 cells after 48 hours. The enhancement was significant over that of NGF alone at guanosine concentrations of 30 and 300 mM. Adenosine did not enhance NGF induced neurite outgrowth at any concentration. This indicates that neurite outgrowth induced by purines is not just a generalized phenomenon. 5'-N-ethylcarboxamidoadenosine (NECA), an adenosine $A_1$ and $A_2$ receptor agonist, also enhanced neuritogenesis, but not to the same extent as guanosine.

On their own, in the absence of NGF, both adenosine and guanosine slightly increased the proportion of cells with neurites as shown in FIG. 14B. The effects of guanosine at both 30 and 300 mM were greater than adenosine at the same concentrations. In the presence of NECA, there was little stimulation of neurite outgrowth. Because the effects of the compounds in the presence of NGF were much more readily scored and less variable from experiment to experiment than with the compounds alone, most of the data for enhancement of neurite outgrowth was determined in the presence of NGF.

Figure 14C:
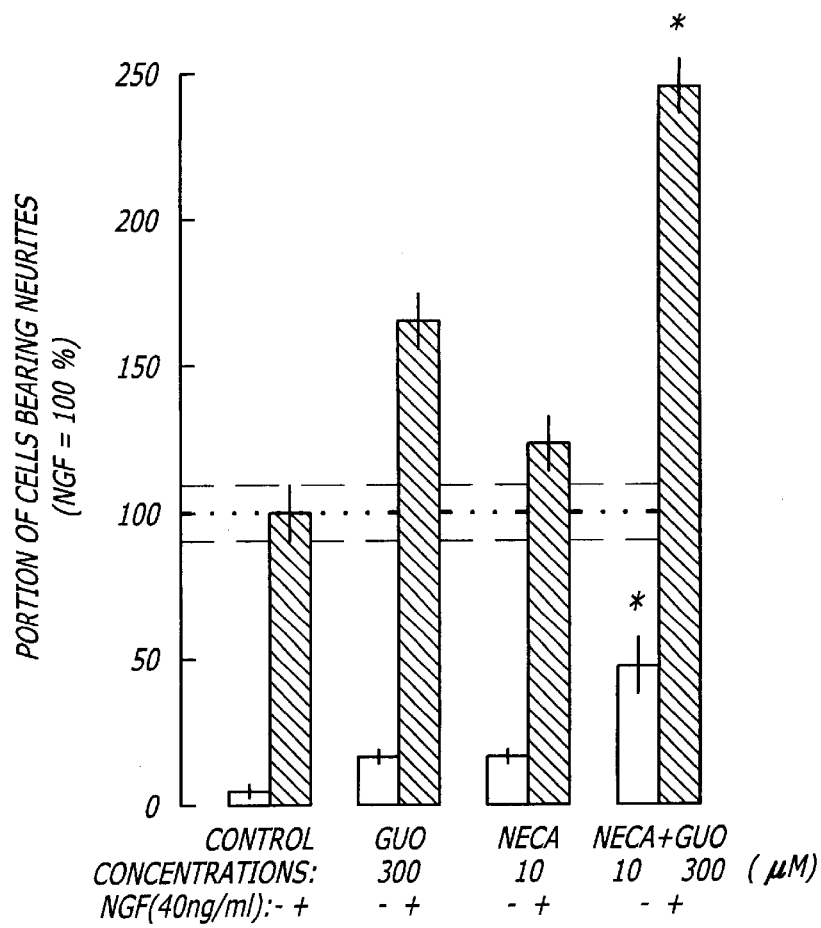

The comparative data shown in FIGS. 14A and 14B and emphasized in FIG. 14C show that guanosine causes some neurite extension, but can also react synergistically to enhance the trophic effects of NGF. Adenosine, although slightly enhancing neurite outgrowth on its own does not enhance the effects of NGF. Interestingly, NECA but not adenosine could synergistically enhance the actions of guanosine, both in the presence and absence of NGF as shown in FIG. 14C. The fact that adenosine did not increase NGF-dependent neurite outgrowth in PC12 cells but that guanosine did, suggests that they interact differently with PC12 cells. Adenosine would interact with adenosine receptors, such as the A2 purinoceptor. This would activate adenylate cyclase which increases intracellular cAMP. NECA apparently acts in this manner. But the effects of NECA were synergistic with those of guanosine. This indicates that guanosine and NECA use different signaling pathways to enhance neurite outgrowth.

EXAMPLE 28

Various Purine Derivatives Provide Different Rates of Neuritogenesis

In view of the previous results, other exemplary purine derivatives were examined to demonstrate the specificity of those compounds which modulate carbon monoxide dependent guanylyl cyclase to modify neural activity. Specifically, different concentrations of the purine derivatives inosine, hypoxanthine and xanthine were tested in the presence of NGF using the protocol of Example 12 to demonstrate their ability to modify neural activity.

Figure 15A:
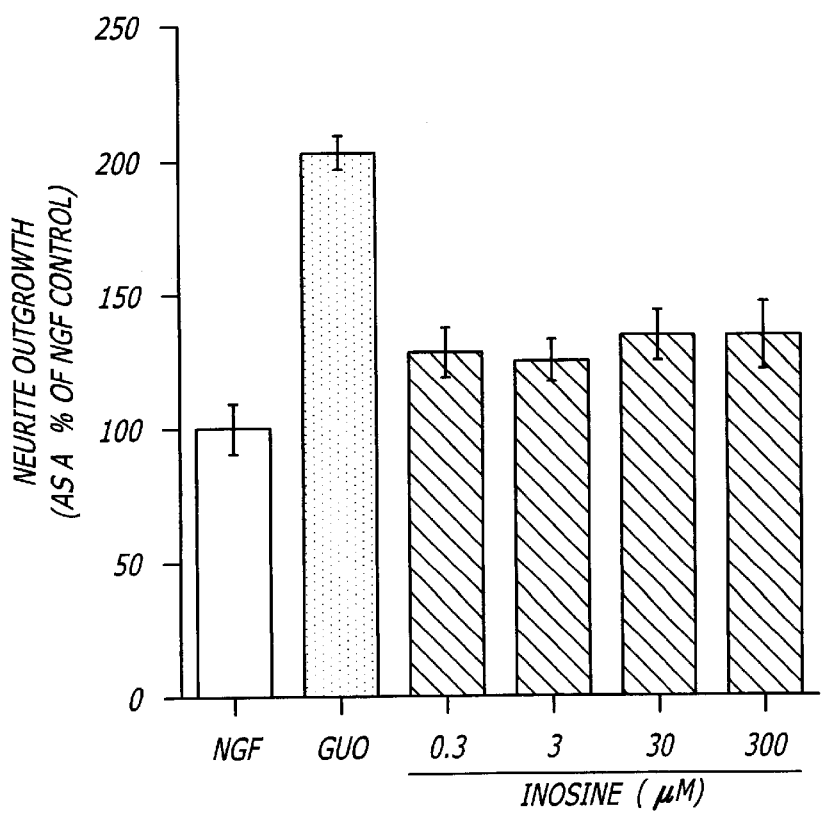
FIGS. 15A, 15B and 15C are graphical comparisons of nerve growth factor mediated neuritogenic responses in neurons grown in the presence of various concentrations of different purine derivatives.

As shown in FIG. 15A, inosine only slightly enhanced neurite outgrowth over that produced in cells treated with NGF alone. This was true for concentrations of inosine ranging from 0.3 to 300 mM. FIG. 15A also shows that the action of inosine on the enhancement of neurite outgrowth was much less effective than that of guanosine.

Figure 15B:
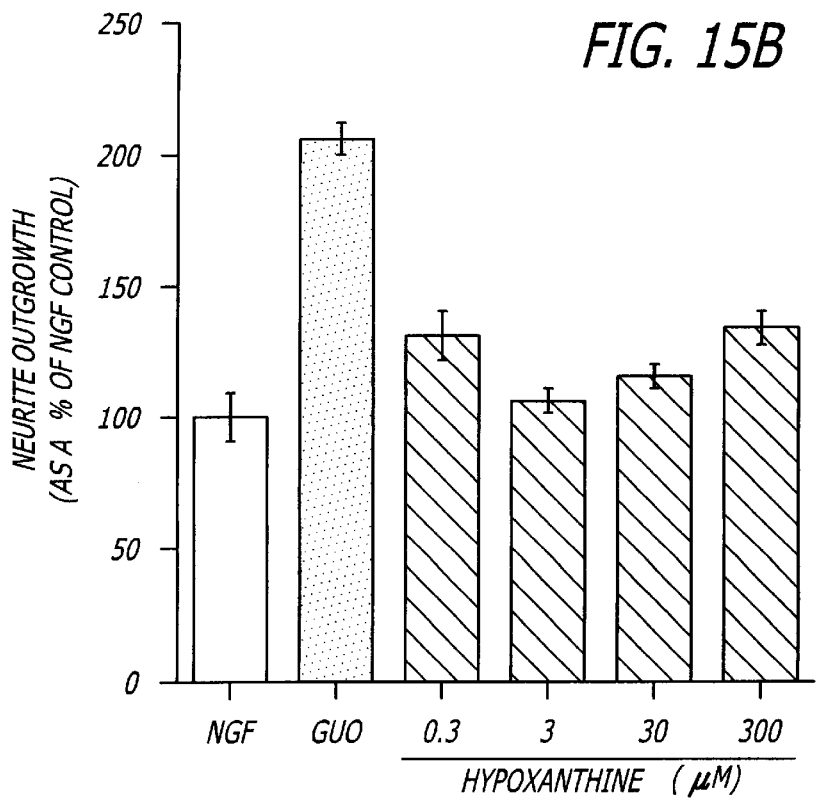
Figure 15C:
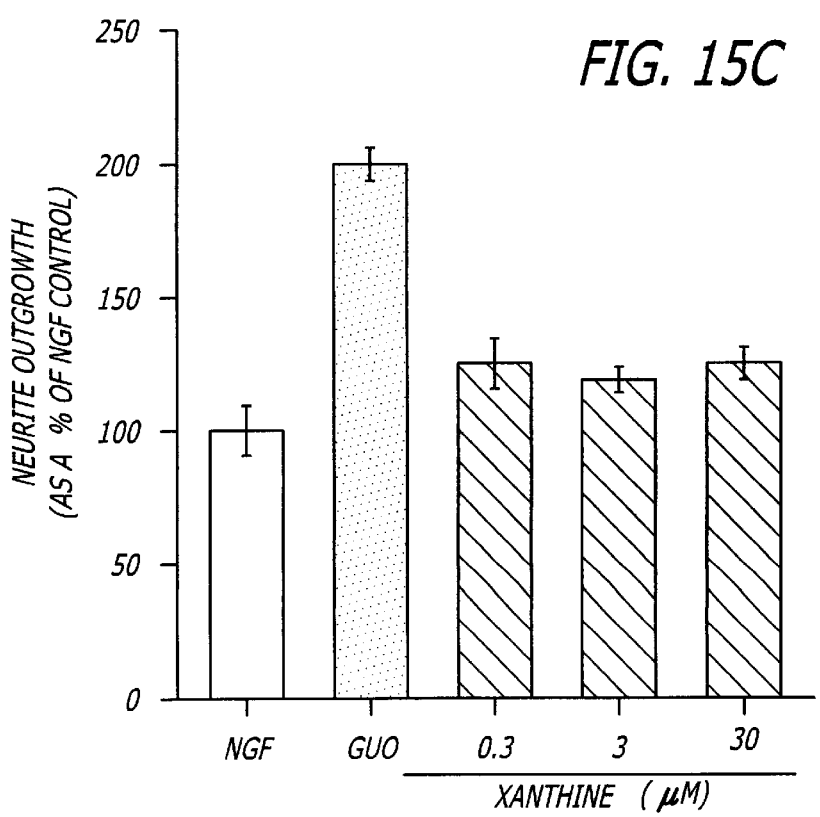

FIGS. 15B and 15C also show that hypoxanthine and xanthine each produced results similar to that of inosine on NGF-induced neuritogenesis. In FIG. 15C xanthine, in concentrations from 0.3 to 30 mM (300 mM was toxic to the cells), only slightly enhanced NGF-induced neurite outgrowth. FIG. 15B shows that hypoxanthine showed the greatest, although still modest, enhancement at concentrations of 0.3 and 300 mM, although other concentrations had no significant enhancement. Even though some enhancement of neurite outgrowth was observed with hypoxanthine, the relative amount of enhancement was not nearly as great as was the effect of guanosine. These results indicate that inosine, xanthine and hypoxanthine do not modulate the carbon monoxide-dependent guanylyl cyclase system to modify neural activity but rather influence other signaling mechanisms to the extent that enhancement was observed.

EXAMPLE 29

Effects of AIT-34 on Neuritogenesis

Figure 16:
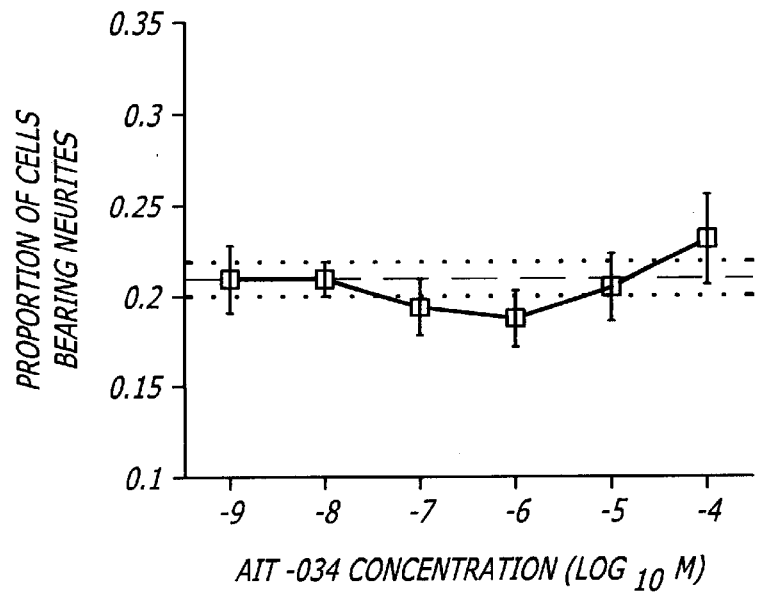
FIG. 16 is a graphical representation of nerve growth factor mediated neuritogenesis measured for neuronal cells grown at various concentrations of the purine derivative AIT-034.

To demonstrate the effects of compounds similar to AIT-082 on neuritogenesis, PC12 cells were exposed to AIT-34, otherwise known as 3-(1,6 dihydro-6-oxo-9h purin-9-yl)-N-(3-(2-oxopyrrolidin-1-yl)propyl) propanamide, during growth and monitored according to Example 12. As shown in FIG. 16, different concentrations of AIT-034 did not enhance NGF-induced neuritogenesis as is observed with AIT-082.

EXAMPLE 30

Effects of ATP and GTP on Neuritogenesis

To further demonstrate that purine derivatives having different functional groups may be used in accordance with the teachings of the present invention, PC12 cells were exposed to adenosine triphosphate (ATP) and guanosine triphosphate (GTP) and monitored for neuritogenesis using the protocol of Example 12.

Figure 17:
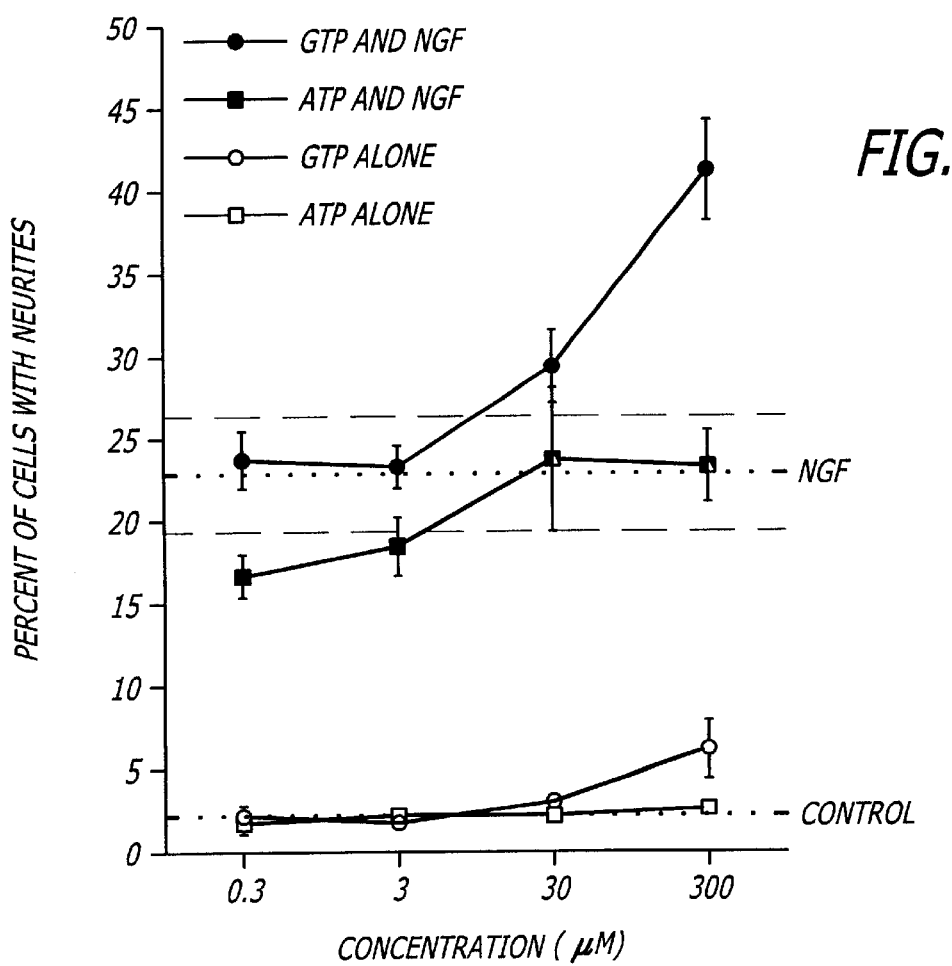
FIG. 17 is a graphical comparison of neuritogenic response of neuronal cells grown at various concentrations of guanosine triphosphate and adenosine triphosphate with and without nerve growth factor.

In a manner very similar to the actions of adenosine and guanosine on neurite outgrowth in PC12 cells, their corresponding nucleotides ATP and GTP had parallel effects on neurite outgrowth. As shown in FIG. 17, ATP did not enhance neuritogenesis in either NGF treated cells or on its own. In sharp contrast, GTP at 30 and 300 mM did enhance neuritogenesis in the presence of NGF and further elicited neurite outgrowth on its own.

Figure 18:
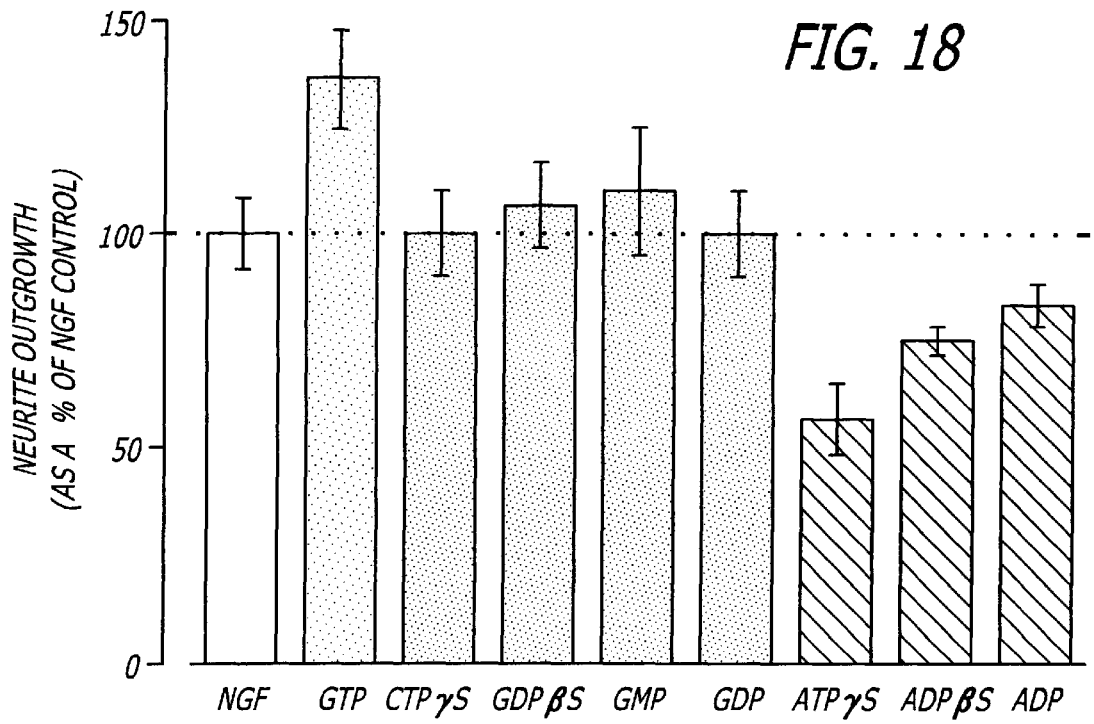
FIG. 18 is a graphical comparison of nerve growth factor mediated neuritogenic response to monophosphate, diphosphate, and triphosphate purine derivatives of guanosine and adenosine.

However, as shown in FIG. 18, GTP) did not appear to be acting as a source from which guanosine was released in a controlled manner. If GTP were hydrolyzed to guanosine diphosphate (GDP), guanosine monophosphate (GMP) and finally to guanosine by ectoenzymes, one would predict that GDP and GMP would also enhance neurite outgrowth from PC12 cells because those less highly phosphorylated molecules would also be converted to guanosine by hydrolysis. Yet, neither GDP nor GMP were effective alone or with NGF in eliciting neurite outgrowth. By way of comparison, the adenine-based compounds all had an inhibitory effect.

EXAMPLE 31

Guanosine but not GTP Increases cGMP in PC12 Cells

Figure 19:
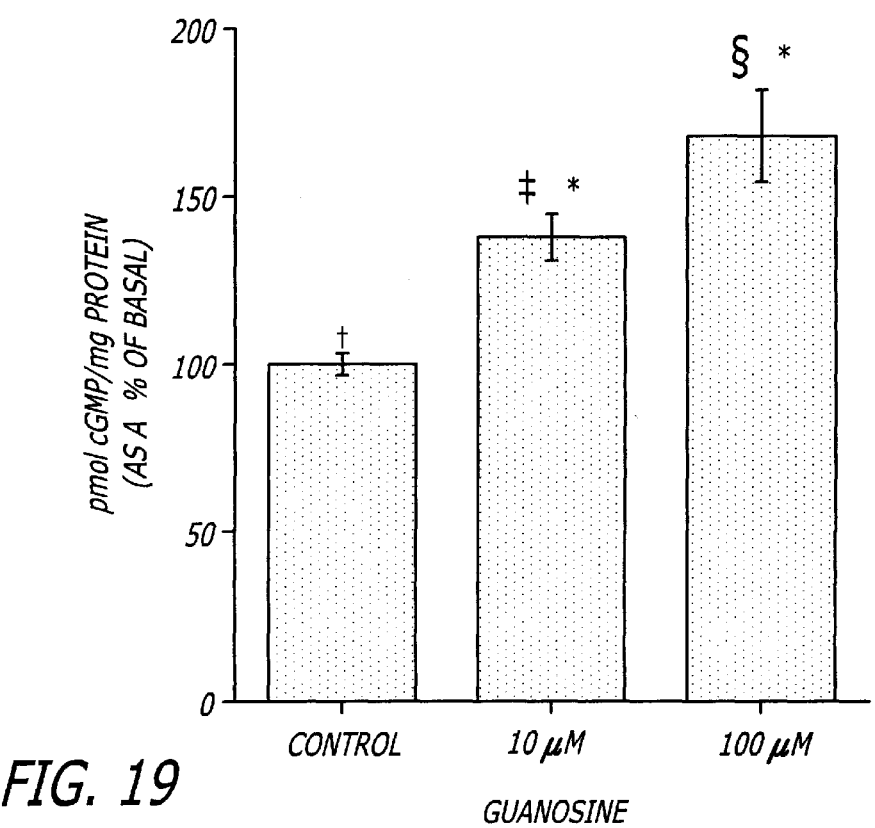
FIG. 19 is a graphical comparison of cyclic GMP produced in neuronal cells grown in the presence of different concentrations of the purine derivative guanosine.

Based on the previous examples, a study was conducted to demonstrate the neuritogenic mechanisms of GTP and guanosine respectively. Guanosine and GTP have been shown to increase intracellular cyclic 3',5'-guanosine monophosphate (cGMP) in arterial smooth muscle. Since cGMP analogues have been reported to stimulate neurite outgrowth from neuroblastoma cells it was possible that both guanosine and GTP might exert their effects through increasing intracellular cGMP. As shown in FIG. 19, guanosine increased intracellular cGMP in PC12 cells as determined by radioimmunoassay using the protocol detailed in Example 15. Such an increase would be expected of a carbon monoxide dependent guanylyl cyclase modulator. In contrast, it was found that GTP did not increase levels of cGMP, indicating that any GTP-stimulated neuritogenesis occurs by another mechanism.

EXAMPLE 32

Use of Non-Selective Inhibitors of Guanylyl Cyclase Reduces Guanosine Neuritogenesis To demonstrate that guanosine modifies the carbon monoxide-dependent guanylyl cyclase system, studies were conducted to show that increased levels of intracellular cGMP were necessary for guanosine to enhance NGF's neuritogenic effects on PC12 cells. In particular, different concentrations of three inhibitors of guanylyl cyclase were added to PC 12 cells with guanosine. Neuritogenesis was then determined using the protocol of Example 12.

Figure 20A:
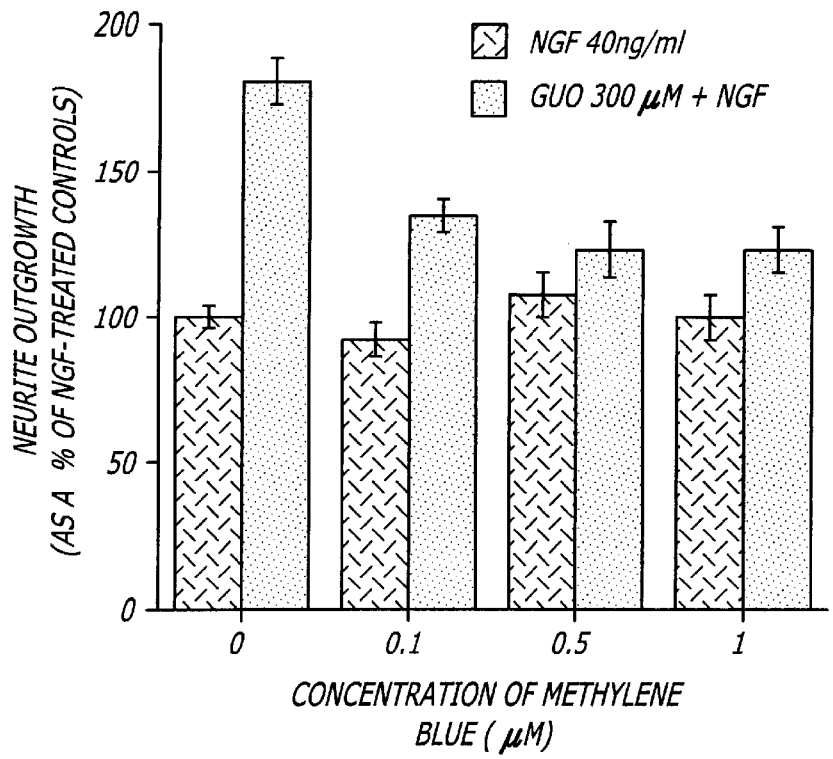
FIGS. 20A, 20B and 20C are graphical comparisons of nerve growth factor mediated neuritogenic responses of cells grown with and without the purine derivative guanosine in the presence of various concentrations of three different inhibitors.

Methylene Blue (MB) inhibits soluble guanylyl cyclase (sGC), the enzyme that synthesizes cGMP. As shown in FIG. 20A the addition of MB (0.1–5 mM) to cultures of PC12 cells abolished the synergistic effects of guanosine with NGF. Conversely, MB had no effect on NGF-stimulated neurite outgrowth.

Figure 20B:
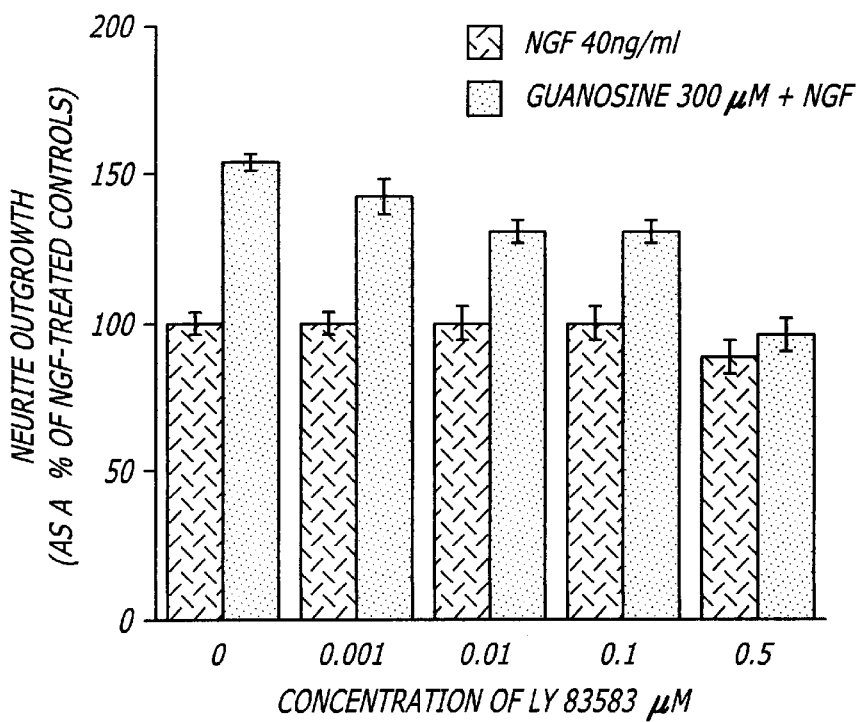

LY83583 inhibits both particulate and sGC. FIG. 20B shows that the neurite outgrowth response elicited by guanosine was inhibited by LY83583, but the response elicited by NGF was unaffected. The mechanism by which LY83583 inhibits guanylyl cyclase is unresolved, but is likely indirect, involving glutathione metabolism. Therefore, two non-selective inhibitors of guanylyl cyclase, each with a different mechanism of action, attenuated the neuritogenic action of guanosine.

These data indicate that guanosine and NGF act through different mechanisms. They also indicate that increases in intracellular cGMP were necessary, although possibly not sufficient, for guanosine to exert its neuritogenic effects.

Figure 20C:
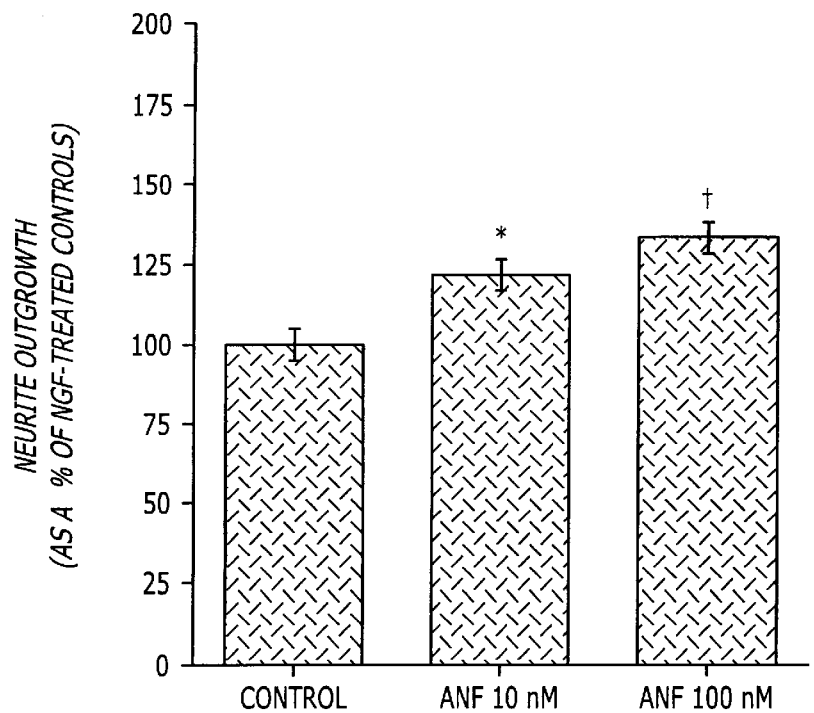

To test whether increases in cGMP were sufficient to cause neurite outgrowth, atrial natriuretic factor (ANF) was added to cell cultures in a manner similar to that used for guanosine. ANF is a hormone whose only known signal transduction pathway is through activation of particulate guanylyl cyclase. As shown in FIG. 20C, ANF, like guanosine, enhanced NGF-stimulated neurite outgrowth from PC12 cells indicating that increased intracellular cGMP production, induced by carbon monoxide dependent guanylyl cyclase or other mechanisms, assisted in stimulating neurite outgrowth.

EXAMPLE 33

Nitric Oxide or Carbon Monoxide Promotes Guanosine Neuritogenesis

Since guanosine increased intracellular cGMP as shown in Example 31, studies were performed to demonstrate whether its signal could be transduced through production of NO or CO. If NO were involved, then addition of nitric oxide donors that liberate NO should mimic the effects of guanosine.

Figure 21:
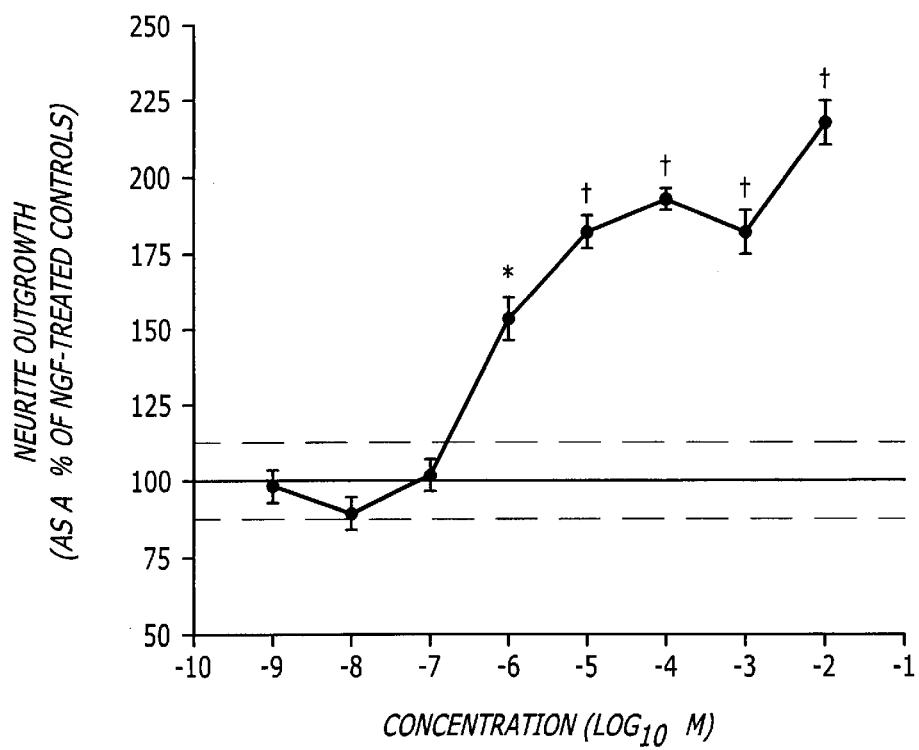
FIG. 21 is a graphical representation of nerve growth factor-mediated neuritogenic responses for neurons grown in the presence of sodium nitrate, an inorganic nitric oxide donor.
Figure 22A:
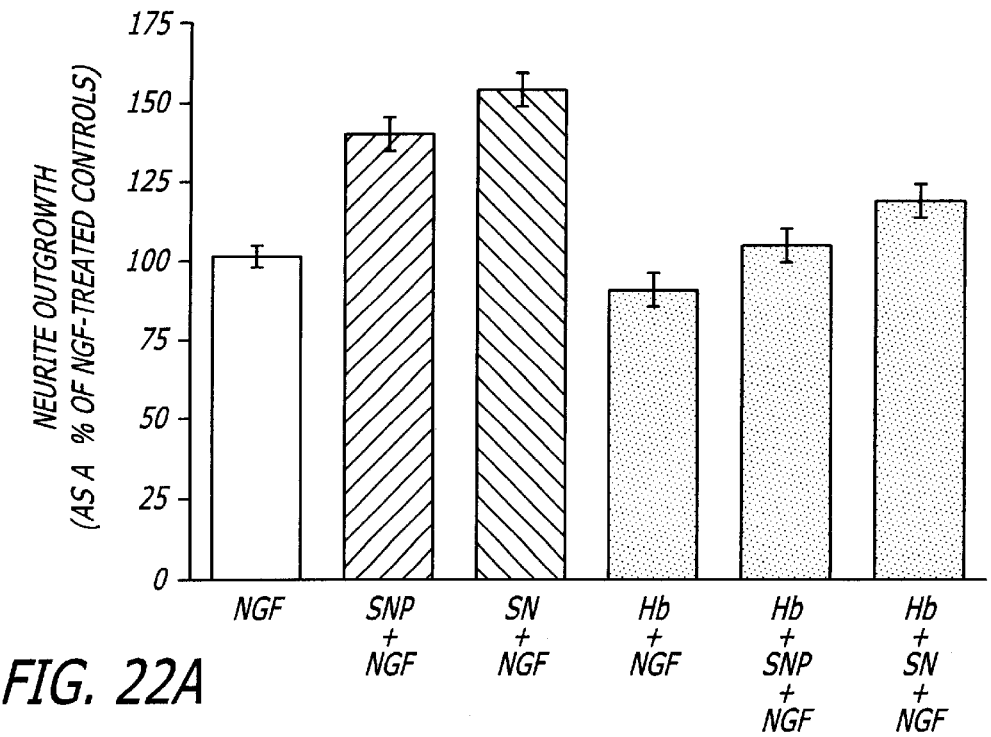
FIGS. 22A and 22B are graphical comparisons of nerve growth factor mediated neuritogenic response of neurons grown in the presence of nitric oxide donors and scavengers of nitric oxide and carbon monoxide.
Figure 22B:
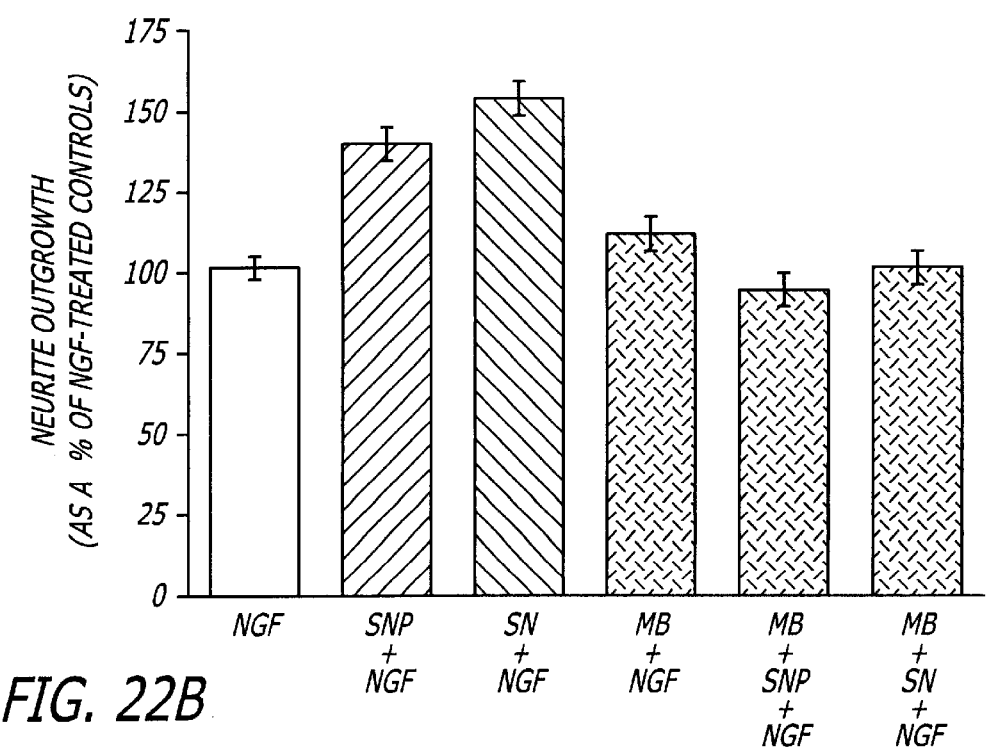

PC12 cells were grown for 48 hours in the presence of sodium nitroprusside (SNP) or sodium nitrite (SN), both of which liberate NO. Alone, neither SNP nor SN elicited neurite outgrowth from PC 12 cells. However, like guanosine, both SNP and SN enhanced NGF-mediated neurite outgrowth in a synergistic manner as shown for the addition of SN in FIG. 21. Further confirming the effect, FIGS. 22A and 22B show that the neuritogenic properties of the NO donors were inhibited by both hemoglobin (Hb) and methemoglobin (MB). Both are substances which scavenge NO and CO with high affinity and preclude these agents from being used as signal transmitters.

Figure 23:
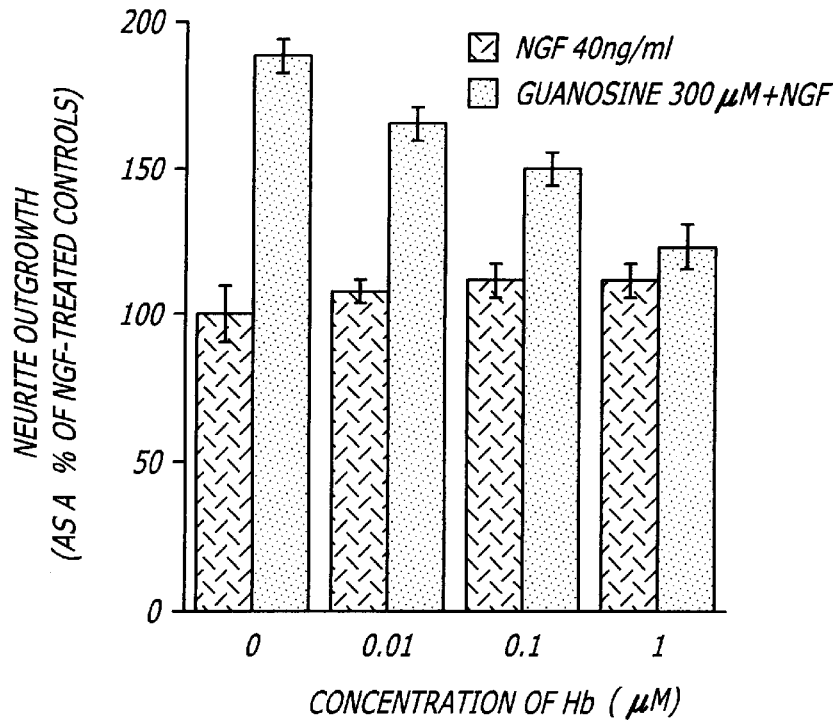
FIG. 23 is a graphical comparison showing the nerve growth factor mediated neuritogenic response of cells grown in various concentrations of hemoglobin with or without the purine derivative guanosine.

Accordingly, if NO or CO mediates the neuritogenic effects of guanosine, then these effects should be reduced by addition of hemoglobin to the cultures. The expected effect is clearly shown in FIG. 23 where Hb (0.1–1 mM) inhibited the neuritogenic effects of guanosine but not those of NGF. This indicates that the neuritogenic action of guanosine, but not that of NGF, requires synthesis of NO or CO.

Several facts indicate that it is CO rather than NO which interacts with guanosine to modify neural activity. For example, if the effects of guanosine were mediated through NO, then addition of guanosine to the PC12 cells should stimulate cNOS in PC12 cells to produce NO. However, cNOS had not been reported in PC12 cells and untreated (guanosine and NGF naive) PC12 cells did not stain for diaphorase, an enzyme that co-localizes with NOS. Since cNOS is calcium/calmodulin-sensitive, its activity should increase after adding a calcium ionophore, thus leading to increased cGMP levels. Addition of the ionophore A23187 to cultures of PC 12 cells failed to elicit an increase in cGMP.

EXAMPLE 34

Carbon Monoxide, not Nitric Oxide, Mediates the Effects of Guanosine on Neuritogenesis Based on the results of the previous examples, studies were performed to demonstrate that the purine derivatives of the present invention, including guanosine, modulate the carbon monoxide-dependent guanylyl cyclase system to modify neural activities.

Figure 24:
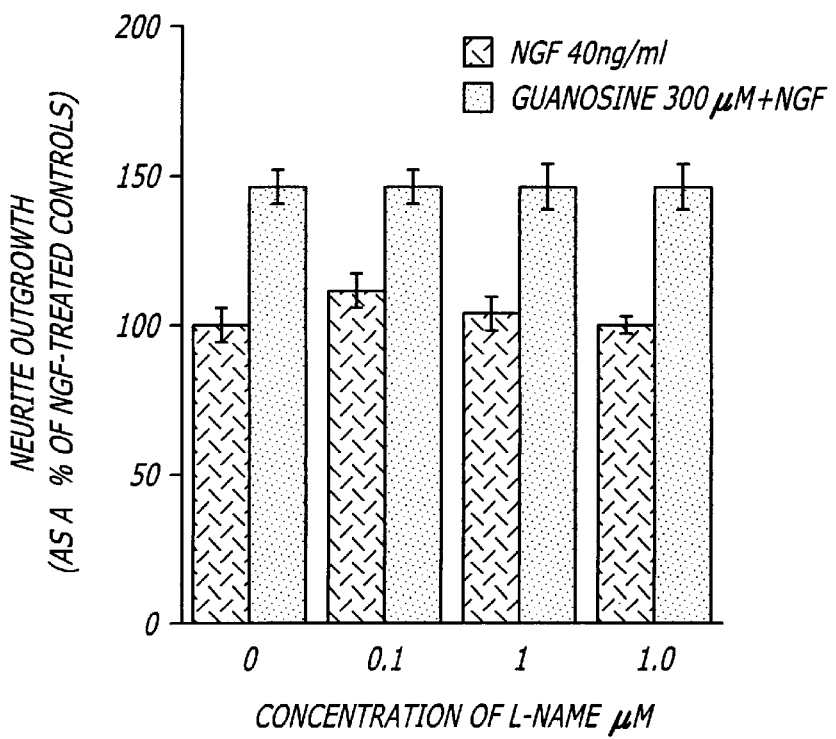
FIG. 24 is a graphical comparison showing the nerve growth factor mediated neuritogenic response of cells grown in various concentrations of L-nitro arginine methyl ester (L-NAME) with and without the purine derivative guanosine.

As in Example 6 where it was shown that carbon monoxide mediates the effects of AIT-082 through the use of inhibitors, the same techniques demonstrate that guanosine also interacts with the carbon monoxide dependent system. Specifically, as shown in FIG. 24, the cNOS inhibitor L-nitro arginine methyl ester (L-NAME) did not affect the ability of guanosine to enhance NGF-mediated neurite outgrowth. These data confirm that cNOS was not involved in the signal transduction pathway that mediated the neuritogenic effects of guanosine on PC 12 cells.

Figure 25:
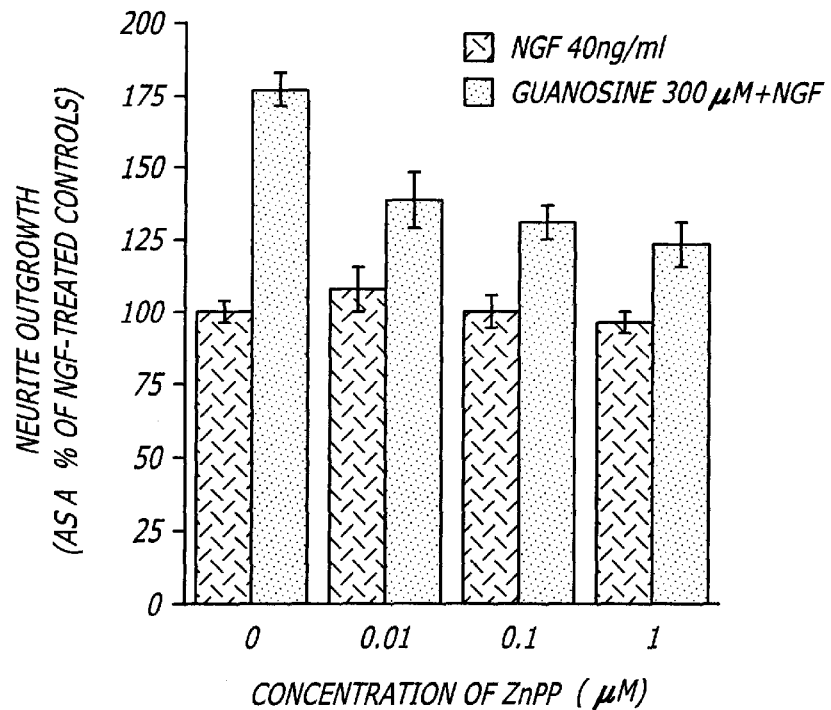
FIG. 25 is a graphical comparison of the nerve growth factor mediated neuritogenic response for cells grown in the presence of various concentrations of zinc protoporphyrin IX (ZNPP), an inhibitor of CO synthesis, with and without guanosine.
Figure 26:
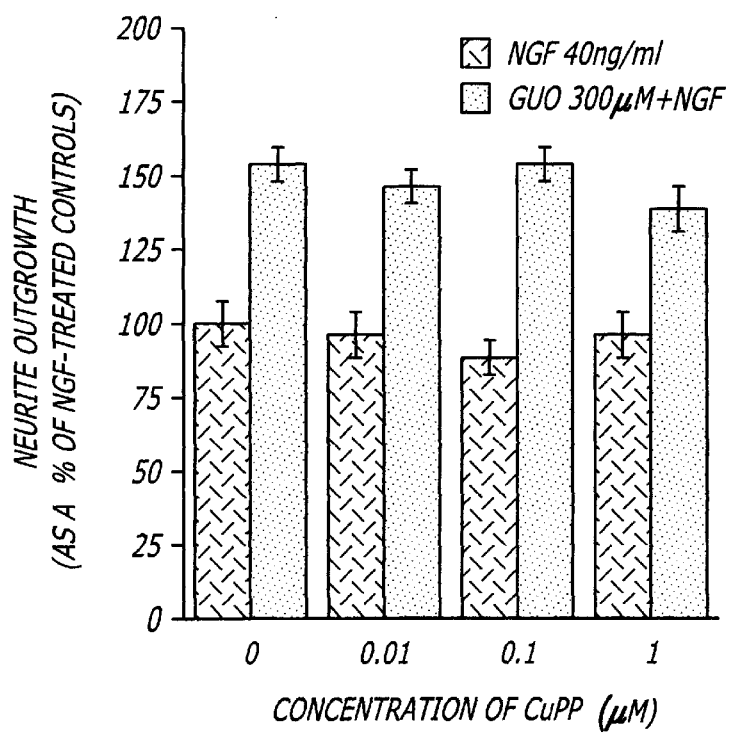
FIG. 26 is a negative control for the graphical comparison shown in FIG. 25 and is a graphical comparison of nerve growth factor mediated neuritogenic response for cells grown in various concentrations of copper protopoiphyrin IX (CUPP), with and without the purine derivative guanosine.

To further demonstrate that CO, rather than NO, mediated the neuritogenic effects of guanosine, zinc protoporphyrin IX (ZnPP), which inhibits heme oxygenase and hence inhibits CO synthesis, was added to the cells during growth. As shown in FIG. 25, ZnPP abolished the neuritogenic effects of guanosine, but did not affect those of NGF. In contrast, a related protoporphyrin derivative, copper protoporphyrin IX (CuPP), does not inhibit heme oxygenase. Accordingly, FIG. 26 shows that copper protoporphyrin IX did not reduce the ability of guanosine to enhance NGF-dependent neurite outgrowth from PC12 cells. As with AIT-082, these data indicated that guanosine increased CO synthesis. In turn, CO activated sGC and increased intracellular GMP, thereby promoting neuritogenesis.

EXAMPLE 35

Inosine Pranobex Enhances Neuritogenesis

To provide further evidence of the scope and operability of the present invention, neuritogenic studies were performed using inosine pranobex. Specifically, inosine pranobex is a mixture of inosine and DIP-PacBa at a 1:3 molar ratio. Various concentrations of this compound were added to PC12 cells with NGF which were then monitored according to the protocol of Example 12.

Figure 27:
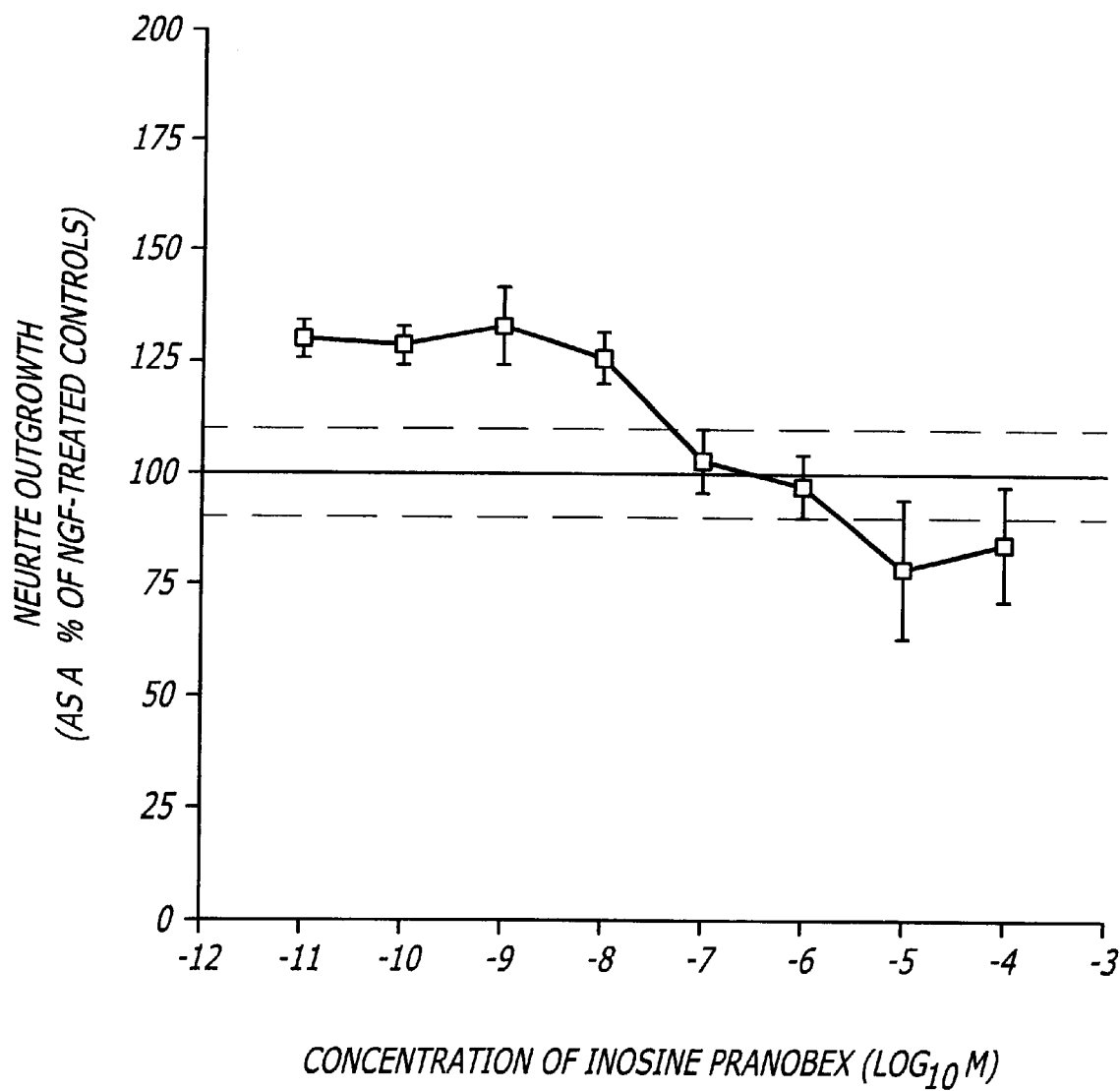
FIG. 27 is a graphical representation of the nerve growth factor mediated neuritogenic response for neuron cells grown in the presence of various concentrations of the purine derivative inosine pranobex.

As shown in FIG. 27, inosine pranobex substantially enhanced the amount of neurite outgrowth of the treated cells. The curve shown in FIG. 27 represents the different levels of inosine pranobex plus saturating concentrations of NGF while the horizontal lines represent the NGF control with attendant confidence levels. Here the treated cells are above the control baseline at most of the selected concentrations.

The modification of neural activity in accordance with the teachings of the present invention may be used to treat neurodegenerative diseases in order to provide recovery of neural function. Thus the methods of the present invention may be used to treat neurodegeneration from any cause including disease, trauma, age and exposure to harmful physical or chemical agents. Similarly, the methods disclosed herein may be used to treat neurological diseases including, but not limited to, Alzheimer's Disease and related degenerative disorders, Parkinson's disease and related disorders such as striato-nigral degeneration, spino-cerebellar atrophies, motor neuronopathies or "motor system diseases" including amyotrophic lateral sclerosis, Werdnig-Hoffman disease, Wohlfart-Kugelberg-Welander syndrome and hereditary spastic diplegia, damage to neurons by ischemia (as in strokes), anoxia, or hypoglycemia (as, for example after prolonged circulatory arrest), Huntington's disease, cerebral palsy, multiple sclerosis, psychiatric disorders including affective disorders, schizophrenia, epilepsy and seizures, peripheral neuropathies from any cause, learning disabilities and disorders of memory. Also, damage to neurons or their processes by physical agents such as radiation or electrical currents or by chemical agents including alcohol, aluminum, heavy metals, industrial toxins, natural toxins and legal or illegal drugs may be treated. The methods may further be used to treat victims of trauma to the brain or spinal cord resulting in neuronal damage or age related conditions such as benign forgetfulness and deterioration of sensory, motor, reflex or cognitive abilities due to loss of neurons or neuronal connectivity. Simply administering an effective dosage of the carbon monoxide dependent guanylyl cyclase modulating purine derivative to a subject suffering from any of the foregoing neural disorders will induce intracellular neuronal changes producing restoration of function.

Specifically, modification of the carbon monoxide dependent guanylyl cyclase system in accordance with the methods of the present invention produces changes in neural activity in neurons and glia cells including astrocytes. For example, using the present invention the neural activity of astrocytes may be modified to synthesize various neurotrophic factors and cytokines including fibroblast growth factor (FGF), nerve growth factor (NGF), brain derived neurotrophic factor (BDNF) and neurotrophin-3 (NT-3). These factors can influence the sprouting of neuritic processes from surviving neurons as well as promote the development of new cells. New synapses may then form and provide some recovery of function. These neurotrophic factors also play a neuroprotective role, thus inducing their production can ameliorate further neural damage.

Numerous purine derivatives may be used in accordance with the teachings of the present invention. However, the ability to modify neural activity by modulating the carbon monoxide dependent guanylyl cyclase system is not a general property of all purines or purine derivatives. For example, as shown in the data below, inosine, adenosine, hypoxanthine and xanthine were all relatively ineffective at modifying neural activity. Other purine derivatives which failed to modify neural activity include 3-(6-amino-9H-purin-9-yl)propionic acid, ethyl ester (AIT-0026), 3-(1,6-dihydro-6-oxo-9H-purin-9-yl)-N-{3-(2-oxopyrolidin-1-yl) propyl)propanamide (AIT-0034) and propentofylline. Moreover, while other purines and purine derivatives such as 5'-N-ethylcarboxamidoadenosine (NECA) were shown to stimulate neurite outgrowth, they did not do so by modulation of the carbon monoxide dependent guanylyl cyclase mechanism. Accordingly, the scope of the invention is defined by the functional reactivity of purine derivatives which modify neural activity as described herein and as shown by the data presented. Of course, those skilled in the art will appreciate that functionally equivalent isomers, analogues and homologues of the compounds of the present invention may be substituted to provide the desired neural modifications.

EXAMPLE 36

AIT-082 Protects Against Neurotoxicity in vitro and in vivo

Enhanced release of glutamate has been implicated in the pathophysiology of neuronal degeneration following acute disorders of the brain. Specific antagonists of glutamate receptors are not therapeutically useful since they impair synaptic plasticity and excitatory transmission, thus reducing learning and memory.

High levels of extracellular adenosine have been found in these pathological conditions and this overproduction presents an opportunity to reduce the neurodegeneration since extracellular adenosine inhibits glutamate release. However, adenosine A1 receptor agonists have not yet been introduced in current therapy because of their many side effects and unsuitable clinical pharmacokinetics.

Glial cells are a major source of extracellular purines and neuroprotective neurotrophic factors (NFs) in the CNS. Systemic administration of NFs as therapeutic agents is limited by their poor penetration across the blood-brain barrier and by the occurrence of peripheral side effects. Thus, good therapeutic strategy for these disorders may be to stimulate the local production of indigenous extracellular adenosine and NFs.

After acute injuries the extracellular concentration of the purine guanosine is higher than that of adenosine and, unlike adenosine, remains elevated for extended periods. Extracellular guanosine has significant neurotrophic and neuroprotective effects, including stimulating the release of adenosine from cells and increasing synthesis of NFs. So guanosine may ameliorate the effects of acute CNS injury. The synthetic purine derivative AIT-082 mimics many of the biological effects of guanosine. Therefore, it was investigated whether AIT-082 might also exhibit the same activities and hence exert neuroprotective effects. Specifically, it was determined whether: (1) AIT-082 protects against long term excitotoxic neuronal damage induced by NMDA, in vitro and in vivo; and (2) the neuroprotective properties of AIT-082 are mediated through its effect on astrocytes.

The exposure of cultured astrocytes to AIT-082 for one hour caused a dose-dependent increase of the outflow of radioactive adenine-based purines, which returned to the basal value two or three hours after the end of the drug treatment. The experiments were carried out on cultured astrocytes of rat hippocampus at the fourth day in vitro (DIV), obtained from primary cultures replated in 35 mm Petri dishes (2×10 cells/dish) and preloaded with [$^3$H]-adenosine ($5 \times 10^{-8}$ M for a specific activity of 20.0 Ci/mM) for 30 minutes at 37° C.

Figure 28:
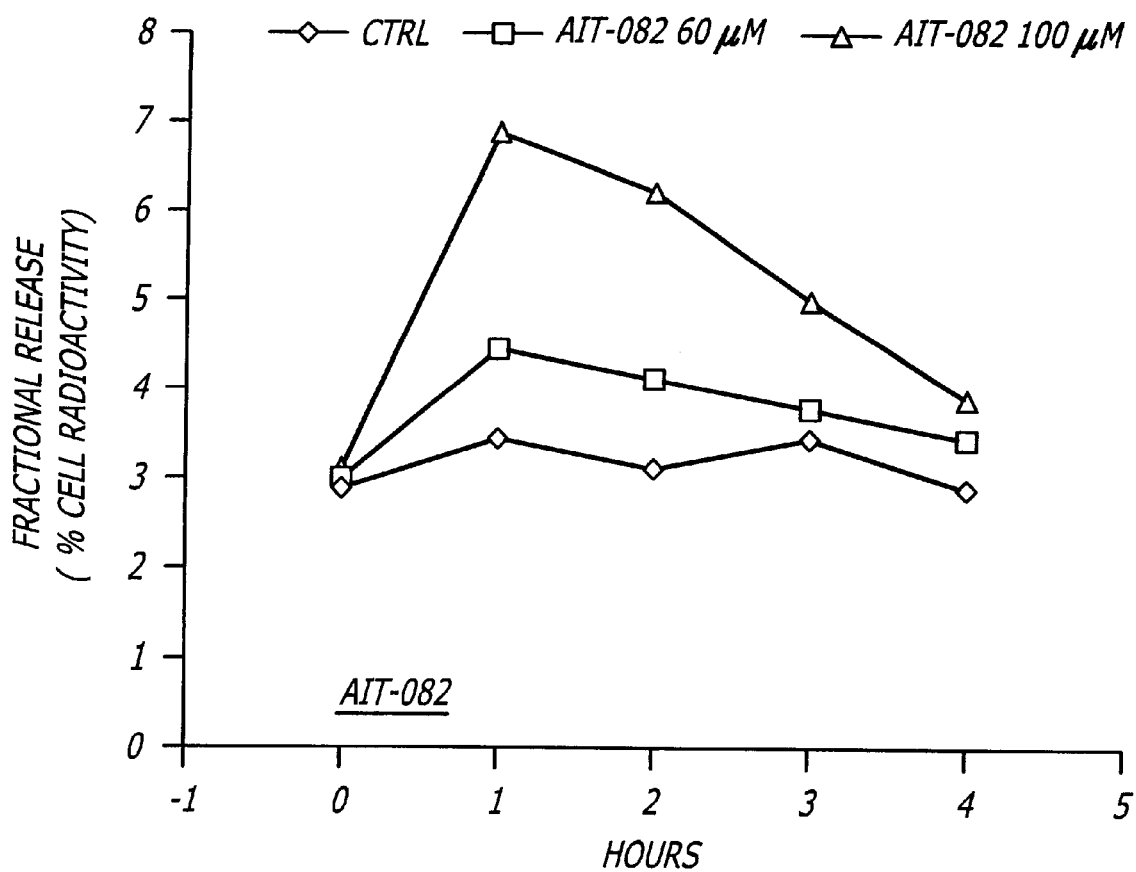
FIG. 28 is a graph showing the dose-dependent increase of the outflow of radioactive adenine-based purines for a limited period after exposure to AIT-082.

The results are shown in FIG. 28. This shows the dose-dependent increase of the outflow of radioactive adenine-based purines for a limited period after exposure.

The effect of GTP and guanosine on proportional release of radioactively labeled adenine nucleosides and nucleotides from rat cultured astrocytes is shown in Table P.

The exposure of astrocytes to GTP (300 μM) for one or three hours significantly stimulated the release of all adenine nucleotides, in particular that of [$^3$H]ADP and [$^3$H]AMP. The release of [$^3$H]adenosine and that of [$^3$H]hypoxanthine was markedly reduced. Conversely, guanosine (300 μM) did not affect the release of radioactively labeled adenine nucleotides but it increased the outflow of [$^3$H]adenosine and to a greater extent that of [$^3$H]inosine.

The effect of AIT-082 on the proportional release of radioactively labeled adenine nucleosides and nucleotides from rat cultured astrocytes is shown in FIGS. 29A and 29B. Culture medium collected during the first hour of the release was analyzed by high performance liquid chromatography (HPLC) and the radioactivity associated with the different adenine compounds was measured and expressed as a percentage of the total radioactivity released. The results are shown for ATP, ADP, and AMP in FIG. 29A, and for adenosine, inosine, and hypoxanthine in FIG. 29B. The exposure of the cultures to AIT-082 increased the release of adenosine and inosine in a dose-dependent fashion, without effecting the release of hypoxanthine and the adenine nucleotides ATP, ADP, or AMP. These results are very similar to those obtained by treating the cultures with guanosine (Table O).

TABLE O

NMDA-Induced Toxicity in Cultured Rat Hippocampal Neurons

|  | 1 hour | | | 3 hours | | |
| --- | --- | --- | --- | --- | --- | --- |
|  | Control | GTP, 300 μM | Guanosine, 300 μM | Control | GTP, 300 μM | Guanosine, 300 μM |
| ATP | 0.37 ± 0.03 | 1.28 ± 0.13 | 0.71 ± 0.09 | 0.29 ± 0.04 | 0.54 ± 0.05 | 0.39 ± 0.04 |
|  | (0.78 ± 0.6) | (10.9 ± 1.1)* | (5.5 ± 0.7) | (4.7 ± 0.7) | (4.4 ± 0.4) | (3.1 ± 0.32) |
| ADP | 0.43 ± 0.03 | 2.10 ± 0.31 | 0.84 ± 0.09 | 0.32 ± 0.04 | 1.05 ± 0.09 | 0.50 ± 0.07 |
|  | (9.0 ± 0.6) | (17.8 ± 2.6)** | (6.5 ± 0.7) | (5.3 ± 0.7) | (8.6 ± 0.7)** | (4.0 ± 0.6) |
| AMP | 0.58 ± 0.05 | 2.76 ± 0.28 | 1.58 ± 0.22 | 0.53 ± 0.06 | 4.32 ± 0.48 | 1.37 ± 0.14 |
|  | (12.2 ± 1.0) | (23.5 ± 2.4)** | (12.3 ± 1.7) | (8.7 ± 1.0) | (40.0 ± 3.9)*** | (11.9 ± 1.0) |

TABLE O-continued

NMDA-Induced Toxicity in Cultured Rat Hippocampal Neurons

| | 1 hour | | | 3 hours | | |
|---|---|---|---|---|---|---|
| | Control | GTP, 300 μM | Guanosine, 300 μM | Control | GTP, 300 μM | Guanosine, 300 μM |
| Adenosine | 0.43 ± 0.04 | 0.47 ± 0.06 | 1.53 ± 0.10 | 0.33 ± 0.04 | 0.31 ± 0.02 | 1.16 ± 0.15 |
| | (9.1 ± 0.8) | (4.0 ± 0.5)** | (11.9 ± 0.8)* | (5.4 ± 0.7) | (2.5 ± 0.2)** | (9.3 ± 0.9)** |
| Inosine | 0.86 ± 0.10 | 1.65 ± 0.2 | 4.64 ± 0.51 | 0.69 ± 0.08 | 1.19 ± 0.19 | 4.09 ± 0.41 |
| | (17.9 ± 2.1) | (14.0 ± 1.7) | (36.0 ± 3.9)** | (11.4 ± 1.3) | (9.7 ± 1.2) | (3.25 ± 3.3)*** |
| Hypoxanthine | 1.62 ± 0.15 | 2.20 ± 0.31 | 3.41 ± 0.20 | 3.41 ± 0.42 | 3.11 ± 0.45 | 3.29 ± 0.34 |
| | (33.9 ± 3.1) | (18.4 ± 2.6)** | (24.7 ± 1.5)* | (56.4 ± 6.9) | (25.0 ± 3.7)** | (26.3 ± 2.7)** |

Radioactivity released in the culture medium and identified by HPLC analysis is reported as cpm × $10^3$. In the parentheses the values are expressed as proportional release, calculated as the percentage of the total [$^3$H]-purines released. The values are the mean ± SEM of 4 experiments
* = p < 0.05;  = p < 0.01; * = p < 0.001 (unpaired Student's t test)

Figure 30A:
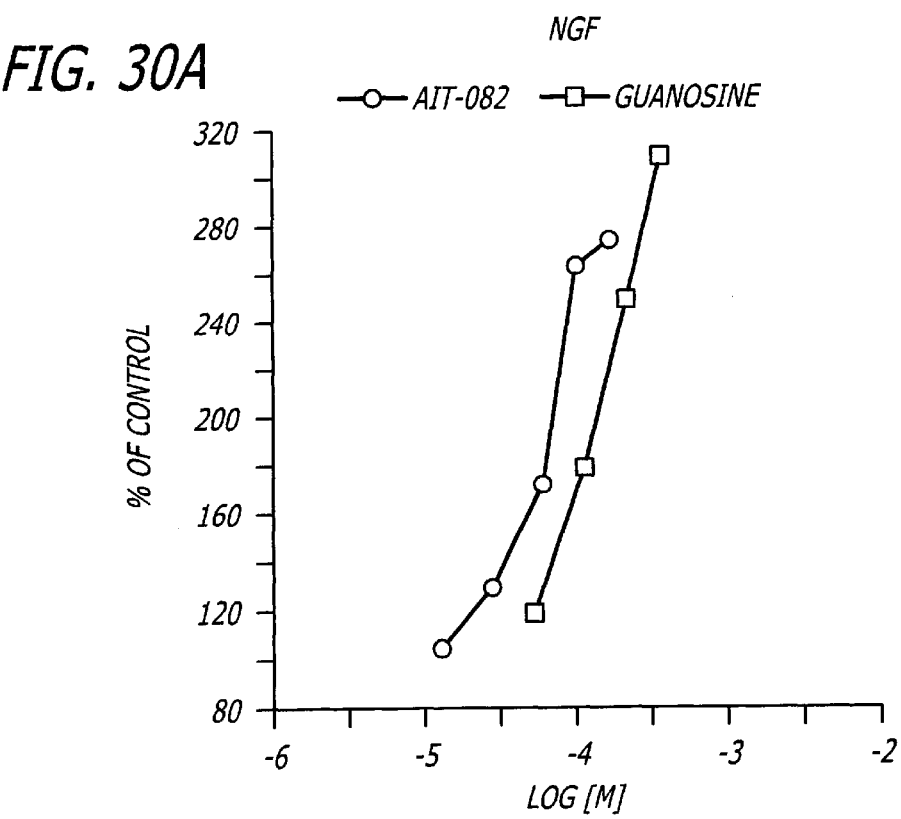
FIG. 30 is a graph showing the dose response for AIT-082 and guanosine on nerve growth factor and S100β protein release from rat culture astrocytes: (A) nerve growth factor; (B) S100β protein.
Figure 30B:
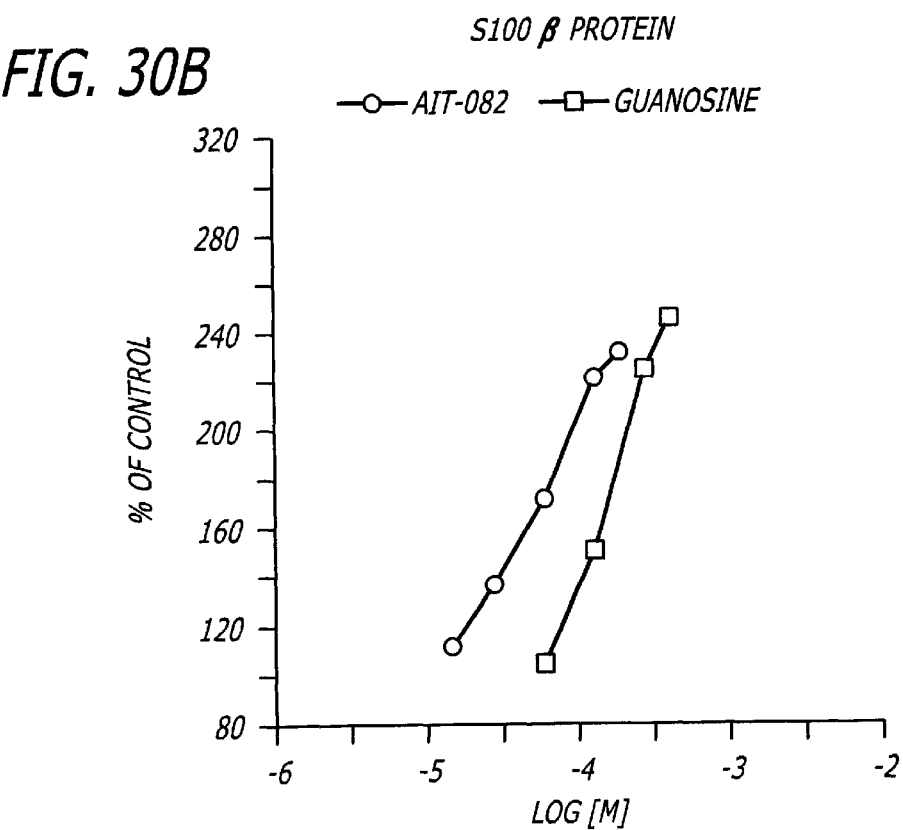

The dose response for AIT-082 and guanosine on nerve growth factor and S100β protein release from rat culture astrocytes is shown in FIG. 30. The release of nerve growth factor is shown in FIG. 30A, while the release of S100β protein is shown in FIG. 30B. NGF was assayed by a double-site ELISA, using a monoclonal anti-NGF antibody, coupled or not to β-galactosidase according to the method of I. D. Laviada et al., "Phosphatidylcholine-Phospholipase C Mediates the Induction of Nerve Growth Factor in Cultured Glial Cells," *FEBS Lett.* 364: 301–304 (1995).

The S100β protein was measured by using an ELISA as described in A. Aurell et al., "The S-100 Protein in Cerebrospinal Fluid: A Simple ELISA Method," *J.Neurol. Sci.* 89: 157–164 (1989).

Previous evidence indicated that AIT-082 or guanosine increased the expression of mRNA for some neurotrophic factors in neurons and in astrocytes. The exposure of astrocytes to these periods for 24 hours also caused a dose-dependent increase of the release of NGF and S100β protein, a calcium binding protein able to promote at nanomolar concentrations neuronal differentiation and astrocyte proliferation. The spontaneous rate of NGF secretion was about 6 pg/hr/2×$10^5$ cells whereas the release of S100β protein was about 40 fold higher.

Figure 31:
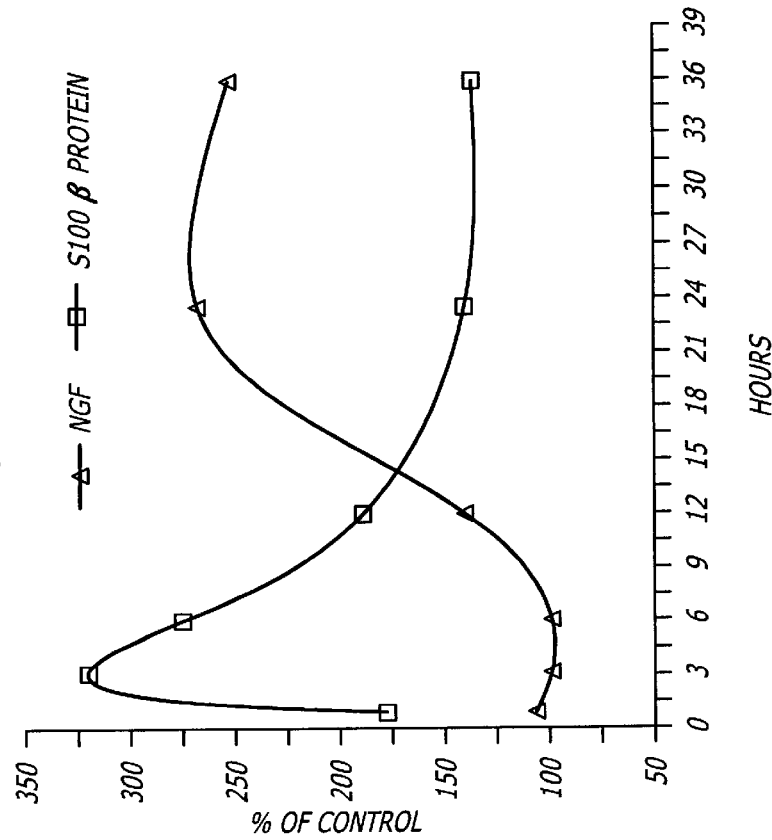
FIG. 31 is a graph showing the time course of AIT-082 induced release of NGF and S100β protein from rat cultured astrocytes.

The time course of AIT-082 induced release of NGF and S100β protein from rat cultured astrocytes is shown in FIG. 31. The NGF and S100β protein were measured by removing the cultured medium for the ELISA assays at each indicated time point. The release of S100β protein from astrocytes peaked within three hours of exposure to AIT-082 (100 μM), and then progressively decreased. In contrast, the release of NGF was only enhanced 12 hours after the exposure to the drug and reached a maximum at 24 hours.

Figure 32:
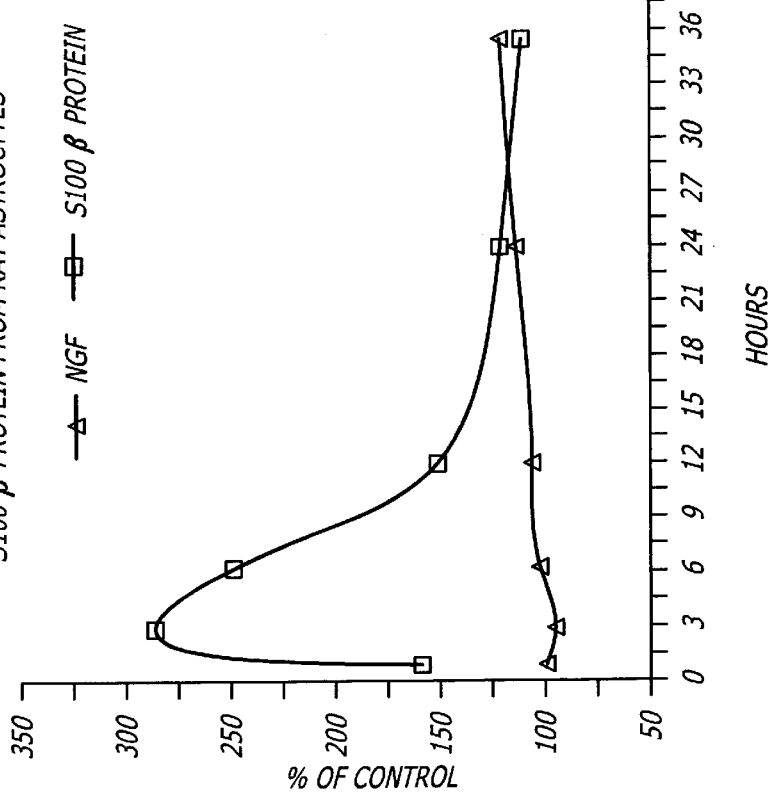
FIG. 32 is a graph showing the time course of AIT-082 induced release of NGF and S100β protein from rat cultured astrocytes.

FIG. 32 shows the effects of cycloheximide on AIT-082-evoked release on NGF and S100β protein from rat cultured astrocytes. To determine whether the release of the neurotrophic factors was linked to new protein synthesis, cultured astrocytes were exposed to an inhibitor of protein synthesis, cycloheximide (0.5 μg/ml). This treatment abolished the stimulatory effect of AIT-082 (100μ) on the release of NGF, whereas the accumulation of S100β protein in the medium was only slightly modified.

To determine whether or not AIT-082 afforded in vitro neuroprotection, the effect of AIT-082 on toxicity induced by N-methyl-D-aspartate (NMDA) in cultured rat hippocampal neurons was studied. In primary cultures of hippocampal neurons, a pulse of 10 min. with NMDA (100 μM) induced within 24 hours a dramatic increase of dead cells, determined by Trypan blue staining or LDH release. Such an increase is consistent with the death of nearly 75% of the cultured neurons as shown in Table P.

TABLE P

NMDA-Induced Toxicity in Cultured Rat Hippocampal Neurons

| | Count of Dead Cells (Trypan Blue Staining) | LDH (mOD/min) |
|---|---|---|
| Basal | 33.4 ± 5.5 | 22.5 ± 4.6 |
| NMDA (100 μM) | 401.4 ± 27.3 | 262.8 ± 13.4 |

To determine whether AIT-082 protected against neuronal toxicity induced by NMDA, and whether astrocytes might be involved, cultured astrocytes were exposed to AIT-082 for 6 hr. The drug was then removed and cultures were kept in fresh medium for the following 20 hr. This conditioned medium was then added to primary cultures of rat hippocampal neurons on the seventh day in vitro, immediately after they had been exposed to a toxic pulse of NMDA.

Figure 33:
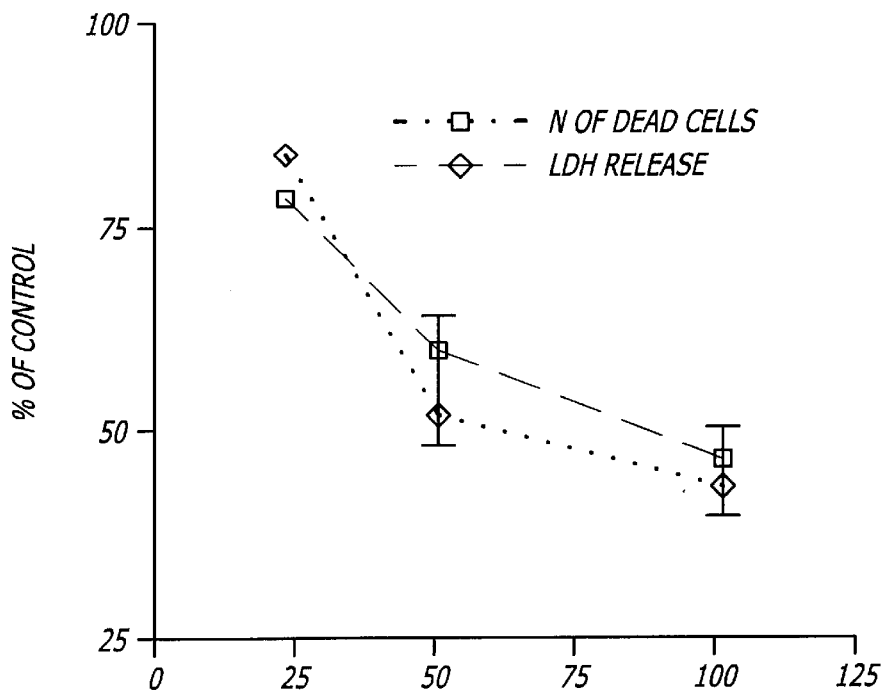
FIG. 33 is a graph showing the effect of conditioned medium removed from astrocytes previously treated with AIT-082 on the toxicity induced by NMDA as measured by the number of dead neurons and the production of LDH.

The results are shown in FIG. 33. Conditioned medium removed from astrocytes, which had been treated with AIT-082 (50–100 μM), reduced by 50% the number of the dead neurons and the production of LDH caused by NMDA treatment.

Figure 34:
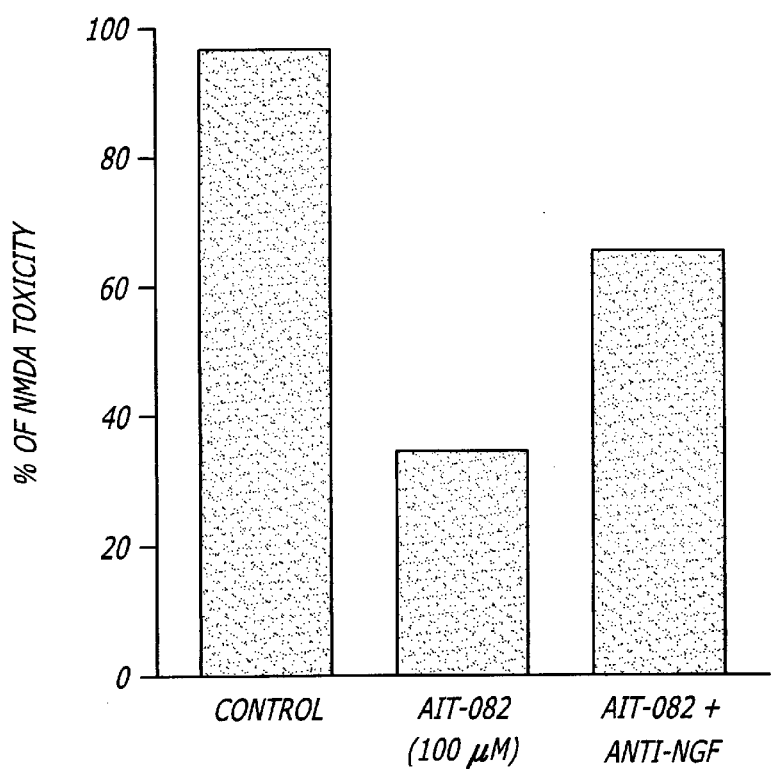
FIG. 34 is a graph showing the effect of anti-NGF antibody on AIT-induced protection of glial conditioned medium in cultured hippocampal neurons damaged by NMDA.

To confirm this, the effect of anti-NGF antibody on AIT-induced protection of glial conditioned medium in cultured hippocampal neurons damaged by NMDA was determined. The results are shown in FIG. 34. The neuroprotective activity of the conditioned medium from astrocytes was strongly reduced by adding a neutralizing antibody specific for NGF.

The effect of AIT-082 on in vivo neuroprotection was also assessed by assaying for glutamic acid decarboxylase (GAD) activity.

Figure 35:
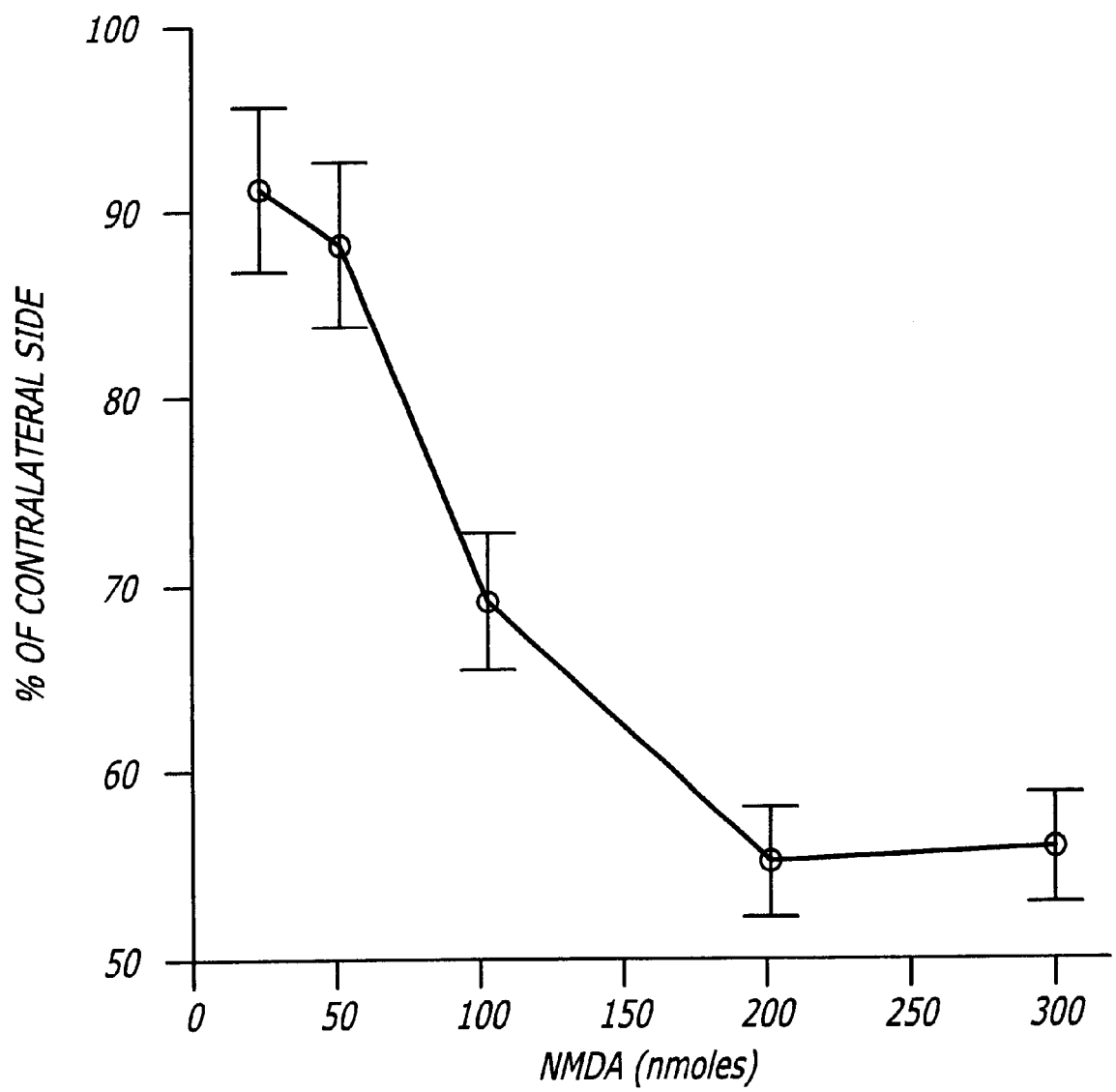
FIG. 35 is a graph showing the damage to glutamic acid decarboxylase (GAD) activity in rat caudate nuclei caused by administration of NMDA.
Figure 36:
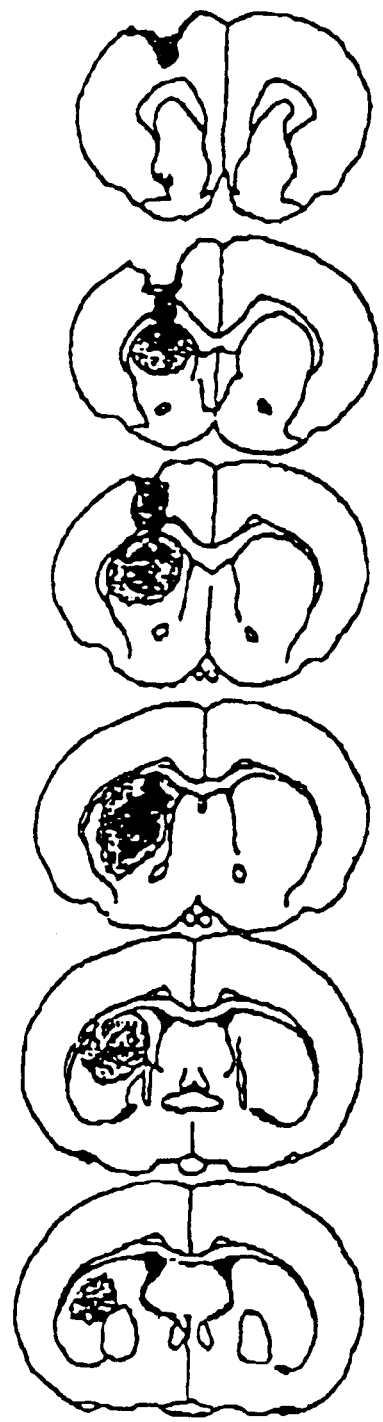
FIG. 36 is a photomicrograph showing the serial frontal sections across the extension of the caudate nuclei from a rat locally infused with 200 nmoles of NMDA.

GAD activity in rat caudate nuclei was damaged in vivo by NMDA. The results are shown in FIG. 35. Increasing amounts of NMDA (25–300 nmoles) were unilaterally infused into caudate nuclei of rats. Eight to 10 days after the injections, glutarnic acid decarboxylase (GAD) activity was assayed, as an index of the loss of GABA-ergic neurons. NMDA produced a dose-dependent lesion, which at its maximal extension caused a reduction of GAD activity by 50% in comparison with that of contralateral sham-operated nuclei (control). FIG. 36 shows the serial frontal sections across the extension of the caudate nuclei from a rat locally infused with 200 nmoles of NMDA. The necrotic areas are in white, whereas the shadow is the surrounding edema GAD activity was evaluated by measuring the ex novo formation of [$^3$H]GABA from dissected striata exposed to 1 $\mu$Ci of [$^3$H]glutamate for 1 hour at 37° C. GABA was assayed by HPLC with fluorescence detection and the [3H] label associated with GABA was measured.

Figure 37:
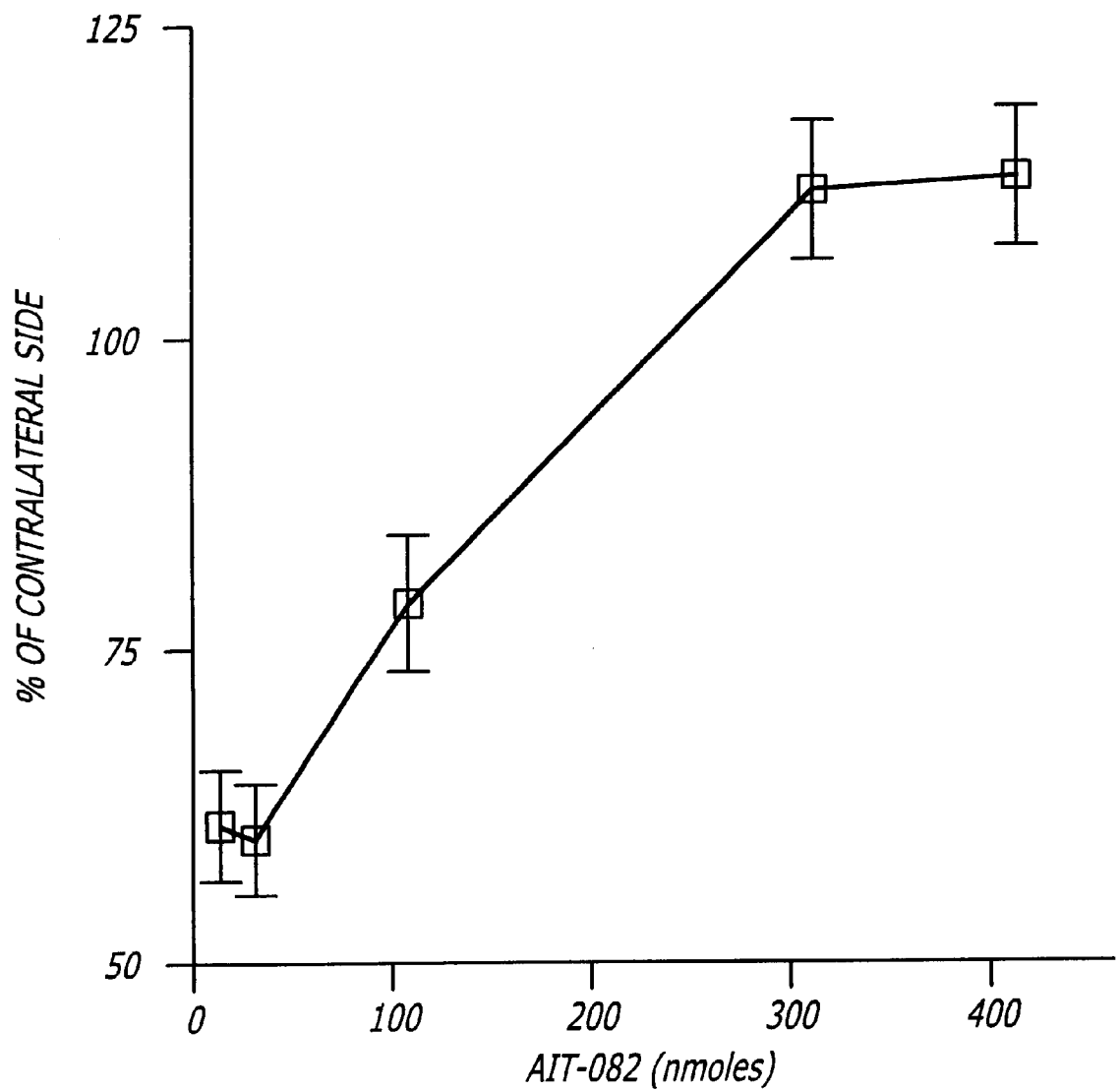
FIG. 37 is a graph showing the effect of local administration of AIT-082 on NMDA-induced unilateral lesion of rat striatum.

The effect of local administration of AIT-082 on NMDA-induced unilateral lesion of rat striatum is shown in FIG. 37. The local adninistration of 300 mnoles of AIT-082, coinfused with 200 nmoles of NMDA, almost completely prevented the loss of GAD activity.

Figure 38:
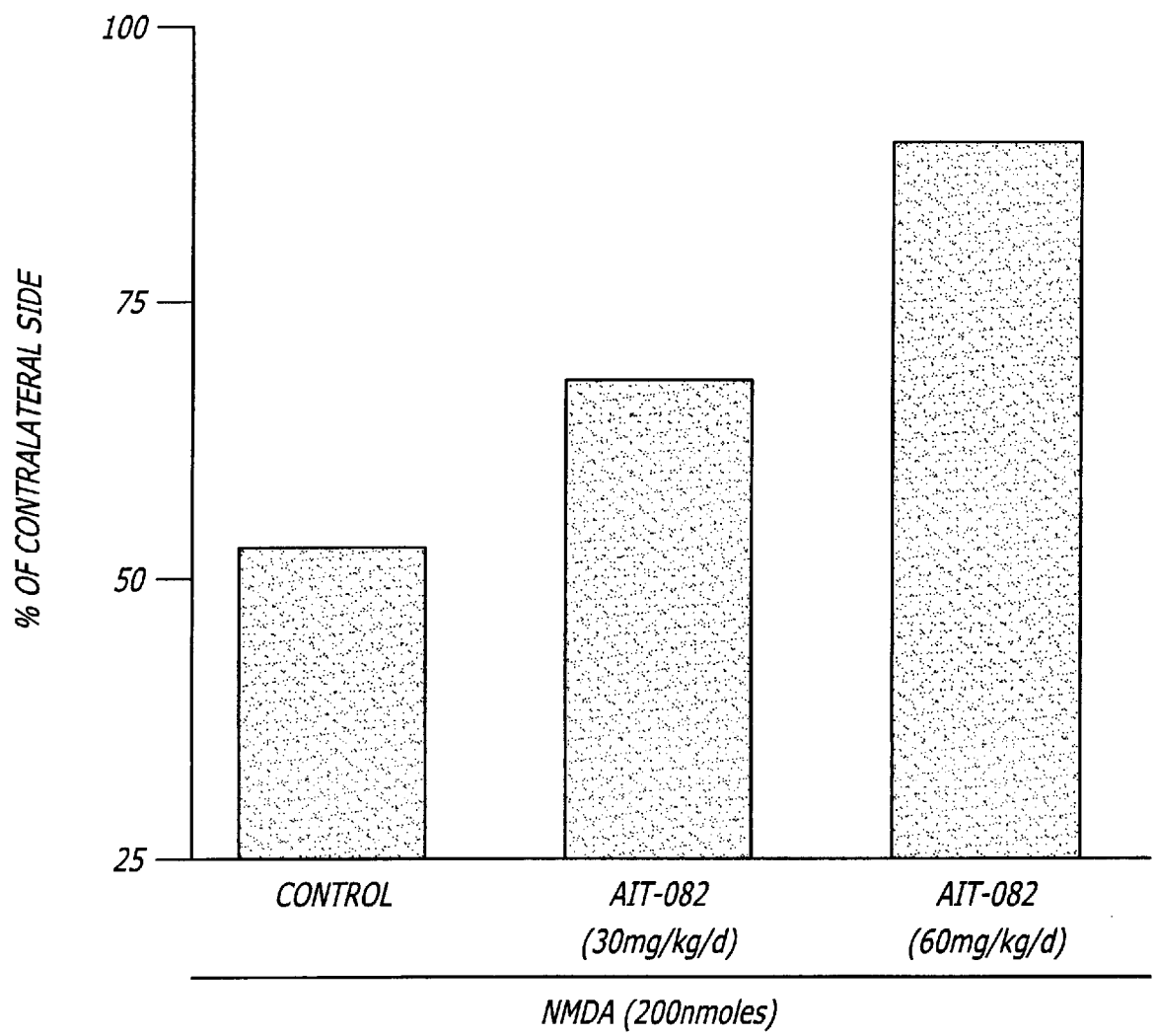
FIG. 38 is a graph showing the effect of systemic administration of AIT-082 on GAD activity in rat caudate nuclei damaged by NMDA.

The effect of systemic administration of AIT-082 on GAD activity in rat caudate nuclei damaged by NMDA is shown in FIG. 38. AIT-082 was administered to rats by daily intraperitoneal injection for seven days. This treatment nearly completely preserved GAD activity in the striata damaged by a local injection of 200 mnoles of NMDA.

Figure 39:
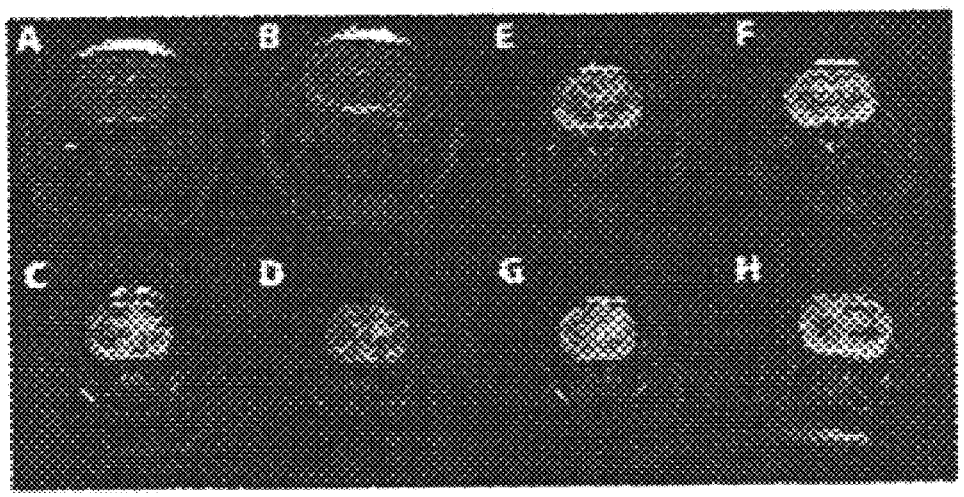
FIG. 39 is a photograph of MRI images of rat striatum injected with saline (A, B), NMDA (C, D), NMDA locally co-injected with AIT-082 (E, F), or NMDA with systemic administration of AIT-082 (G, H)

These results were confirmed by magnetic resonance imaging (MRI). The MRI results are shown in FIG. 39; Table Q shows the identification of each sample for which MRI results are shown in FIG. 39. T-2 weighted MRI photos of transverse brain 3-mm thick slices were performed (TR/TE=7400/115 ms; matrix 483×1024; FLV 250). Magnetic resonance images were acquired using 1.5 T scanner (Vision, Siemens-Erlangen). The control injection of saline did not produce any change (A, B). A focal hyperintensity at the NMDA injection site was observed in brain slices after two days (C) and decrease in the hyperintensity was observed after nine days (D). The brightness of the lesion disappeared when AIT was locally co-injected with NMDA (E, F), and it was significantly reduced with systemic (intraperitoneal) administration of AIT-082 (60 mg/kg) (G, H). All animals survived the surgery and continued to receive treatment for an additional three days, at which time they were sacrificed and tissues were collected as described above.

TABLE Q

MRI of Rat Striatum (FIG. 39)

| Days After Injection in the Left Striata | 2 Days | 9 Days |
| --- | --- | --- |
| Saline | A | B |
| NMDA (200 mmoles) | C | D |
| AIT-082 + NMDA (Local co-injected) | E | F |
| AIT-082 (Systemic i.p.) | G | H |

In conclusion, in cultured astrocytes AIT-082, like guanosine, induce a large increase of the extracellular levels of adenine nucleosides. This contributes to the astrocyte-mediated neuroprotective effect of AIT-082.

In addition to a direct activity of neurons, AIT-082 exerts a potent neuroprotective activity by stimulating astrocytes to synthesize and release neurotrophic factors, such as NGF. S100$\beta$ protein can play a role in the AIT-082-mediated neuroprotection. It may be involved in a cascade of positive feedback mechanisms which raise NGF production.

EXAMPLE 37

Effect of N-4-CARBOXYPHENYL-3-(6OXOHYDROPURIN-9-YL) Propanamide on Growth Factor mRNA Levels Following Splnal Cord Hemisection To determine the effect of the administration of N-4-carboxyphenyl-3-(6-oxohydropurin-9-yl) propanamide on neurotrophic factor levels in the spinal cords of rats, the levels of such neurotrophic factors were measured under various conditions.

Methods

T8 Lesion Surgery

Figure 40:
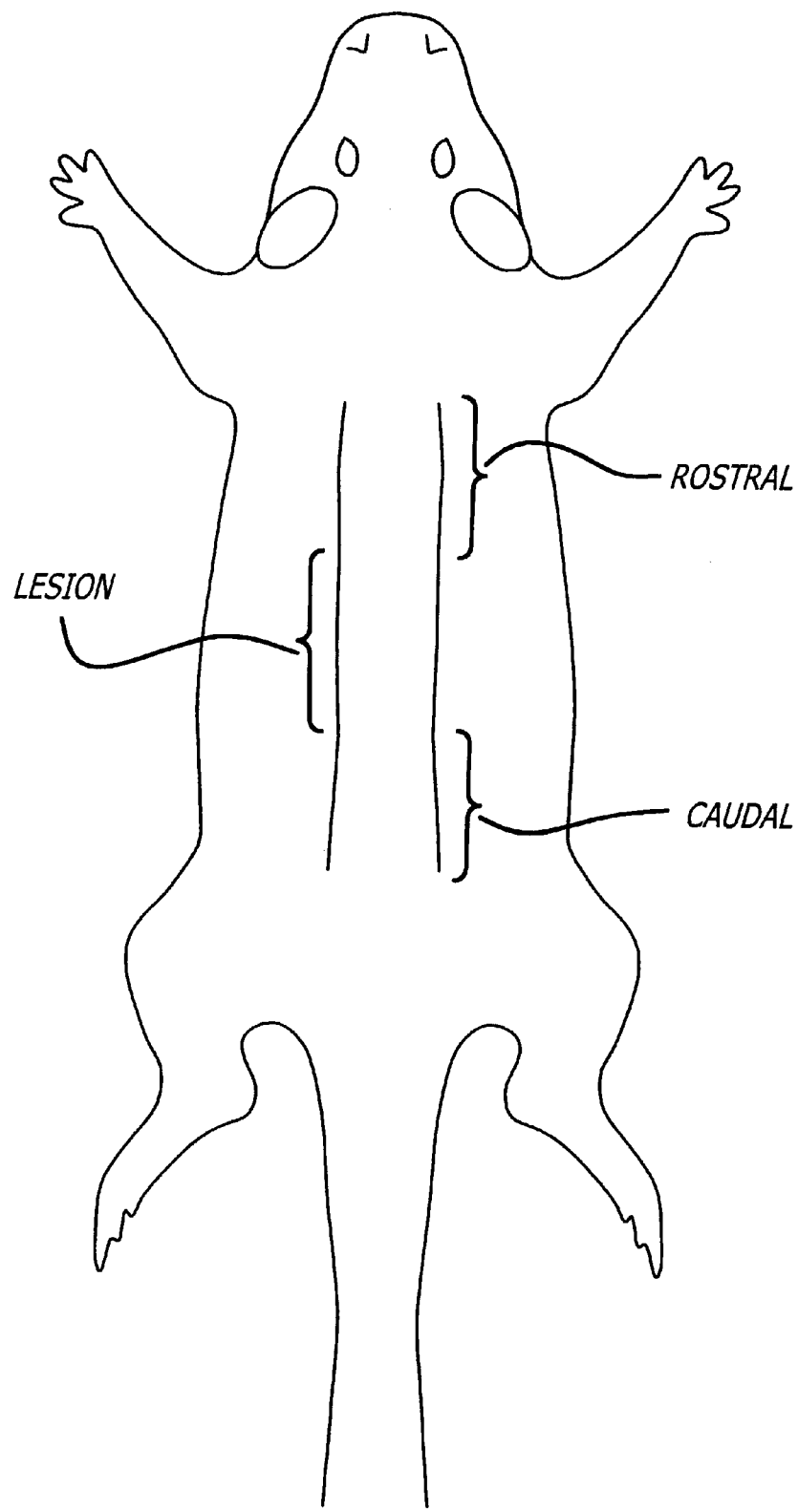
FIG. 40 is a diagram of the location of the lesions made in the spinal cord of rats to which AIT-082 was administered in Example 37.

Male Wistar rats (250 g) anesthetized with ketamine/xylazine received either a partial laminectomy (sham operated control) or full laminectomy and unilateral transection of the spinal cord with a miniscalpel at the level of the eighth thoracic vertebrae. The animals were assigned into four groups: two control groups, one group receiving N-4-carboxyphenyl-3-(6-oxohydropurin-9-yl) propanamide (20 mg/kg day) in the drinking water and the other receiving no treatment. The two other groups were both lesion groups of untreated and treated with N-4-carboxyphenyl-3-(6-oxohydropurin-9-yl) propanamide. A lesion was judged successful by the complete loss of withdrawal reflex 24 hours post surgery. At the end of the treatment period the animals were euthanized and perfused with saline. A 2 cm segment of cord was taken around the laminectomy site, called the lesion sample. Samples were also taken 2 cm above and 2 cm below the lesion (rostral and caudal sections respectively). A diagram of the lesion regions is shown in FIG. 40.

RNA Extraction and RT-PCR

Total RNA was extracted from coded unfixed spinal tissue samples using TRIzol reagent (Gibco-BRL). Total RNA (3 $\mu$g) was reversed transcribed using a recombinant MMLV reverse transcriptase (RT) called Superscript II (Gibco-BRL) in a 20 $\mu$l reaction primed with oligo-dT$_{18}$ (MOBIX) using buffer and dithiothreitol supplied with the enzyme. Two aliquots (1 and 2.5 $\mu$l) of the RT mixture were amplified in a mixture containing 0.2 mM dNTPs, 1×PCR buffer, 1.5 mM MgCl$_2$, Taq polymerase (Gibco-BRL) and 0.1 $\mu$g of sense and antisense primer (MOBIX). The quantitation of products was done from ethidium bromide stained gels using an LKB laser scanner using the ratio of the 1 $\mu$l to 2.5 $\mu$l replicates to ensure that threshold fluorescence had not been reached. All samples were read in the exponential phase of the amplification curve for the primer set. All three primers sets were run from the same RT sample. The equivalence of the amount of RNA in each of the samples was corrected for the expression of the housekeeping gene, G3PDH.

Results

RT-PCR was used to measure the mRNA levels of 3 neurotrophic factors, CNTF, BDNF, and NT-3 in 3 sections of the spinal cord as illustrated in FIGS. 41–43, after 3 or 7 days of treatment with N-4-carboxyphenyl-3-(6-oxohydropurin-9-yl) propanamide. The levels of gene expression were normalized to G3PDH expression. The results are expressed as relative ng of DNA after RT-PCR which are considered to reflect the levels of mRNA expression in the original RNA samples.

Rostral to the lesion, 3 days of treatment with N-4-carboxyphenyl-3-(6-oxohydropurin-9-yl) propanamide significantly increased the levels of BDNF and CNTF mRNA in sham-operated animals over the lesion animals. This trend was reversed for BDNF after 7 days of treatment with the compound when the relative levels of mRNA expression were significantly higher in the lesioned animals treated with the compound than in the lesioned animals that had not been treated with the compound. The compound, after 7 days, increased CNTF mRNA levels relative to lesion alone (p=0.056). However, in the control animals, the drug treatment induced a robust increase (p=0.017) in CNTF levels over water alone. At the rostral level, the surgical treatment alone did not significantly alter CNTF mRNA levels. At the level of the lesion, treatment with the compound increased mean CNTF mRNA levels over control animals, although not statistically so. There were no significant differences due to surgery or drug treatment at this level.

Caudal to the lesion for the control animals, NT-3 mRNA was decreased after 3 days of treatment with the compound. BDNF mRNA was higher in the sham-operated animals than in the lesioned animals when both groups received the compound. There were no significant effects with 7 days of treatment with the compound post surgery.

Figure 41B:
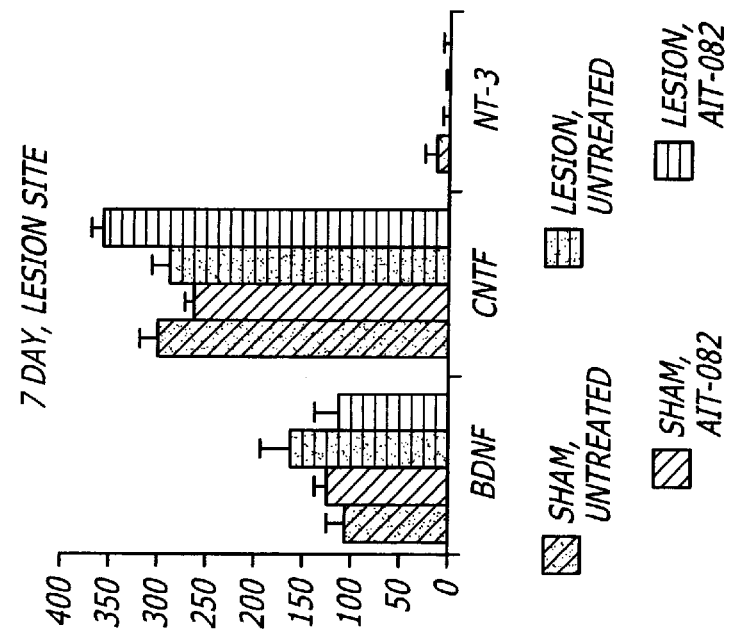
FIG. 41 is a graph of the level of niRNA for the neurotrophic factors brain-derived neurotrophic factor (BDNF), ciliary neurotrophic factor (CNTF), and NT-3 at the lesion site for animals lesioned or sham-lesioned in Example 37: (a) levels measured 3 days after lesioning or sham-lesioning; (b) levels measured 7 days after lesioning or sham-lesioning.
Figure 41A:
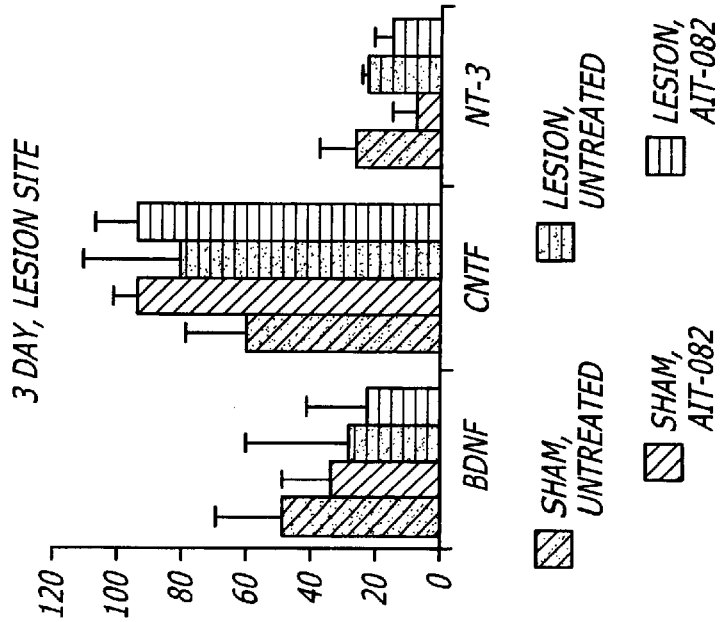

The levels of mRNA at the lesion site for the neurotrophins are shown in FIG. 41 (FIG. 41a, after 3 days of treatment; FIG. 41b, after 7 days of treatment). The animals were treated for 3 (FIG. 41a) or 7 days (FIG. 41b) as indicated. The error bars represent S.E.M.s (n=3 or 4). There were no significant differences between treatment groups. The mRNA levels shown in FIG. 41 were measured by RT-PCR on a 2 cm portion of the spinal cord at the T8 lesion site as described above.

Figures 42A, 42B:
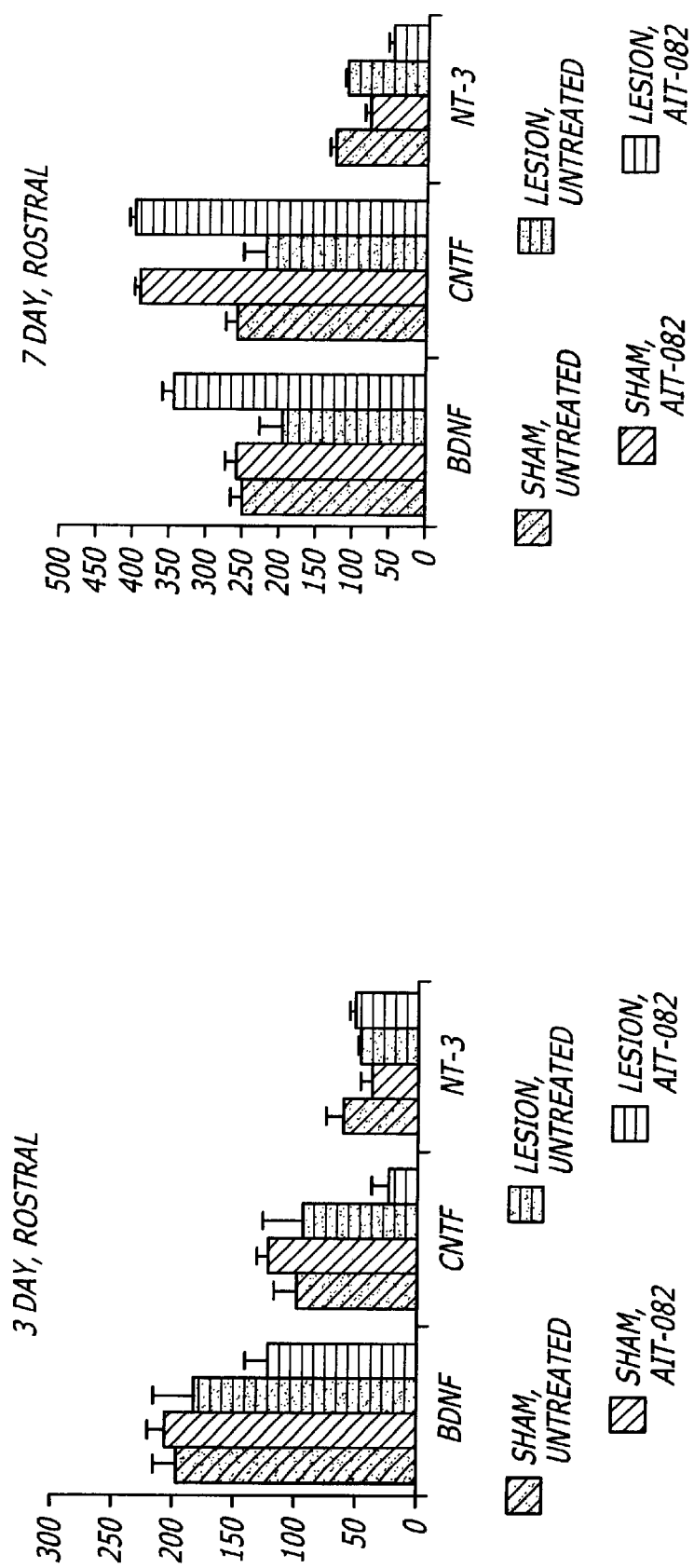
FIG. 42 is a graph of the levels of mRNA for BDNF, CNTF, and NT-3 rostral to the lesion for animals lesioned or sham-lesioned in Example 37: (a) levels measured 3 days after lesioning or sham-lesioning; (b) levels measured 7 days after lesioning or sham-lesioning.

The effects of the compound on levels of mRNA rostral to the lesion are shown in FIG. 42 (FIG. 42a, after 3 days of treatment; FIG. 42b, after 7 days of treatment). The animals were treated for 3 (FIG. 42a) or 7 days (FIG. 42b) as indicated. The mRNA levels were measured by RT-PCR on a 2 cm portion of the spinal cord 1 cm up from the T8 lesion site as described above. Statistical significance was determined by one-way Anova testing. Error bars represent S.E.M.s (n=3 or 4). The level of mRNA for CNTF in the sham-lesioned animals treated with the compound were significantly different from sham-lesioned animals treated only with water (p<0.05) after 7 days of treatment. The level of mRNA for BDNF was also significantly different when lesioned animals treated with the compound were compared with lesioned animals treated only with water (p<0.05) after 7 days of treatment. The level of BDNF mRNA after 3 days of treatment in control animals (i.e. sham-lesioned animals) treated with the compound was significantly different from lesioned animals treated with the compound (p<0.05). Finally, the level of CNTF mRNA at 3 days of treatment in control animals treated with the compound was again significantly different from lesioned animals treated with the compound (p<0.01).

Figures 43A, 43B:
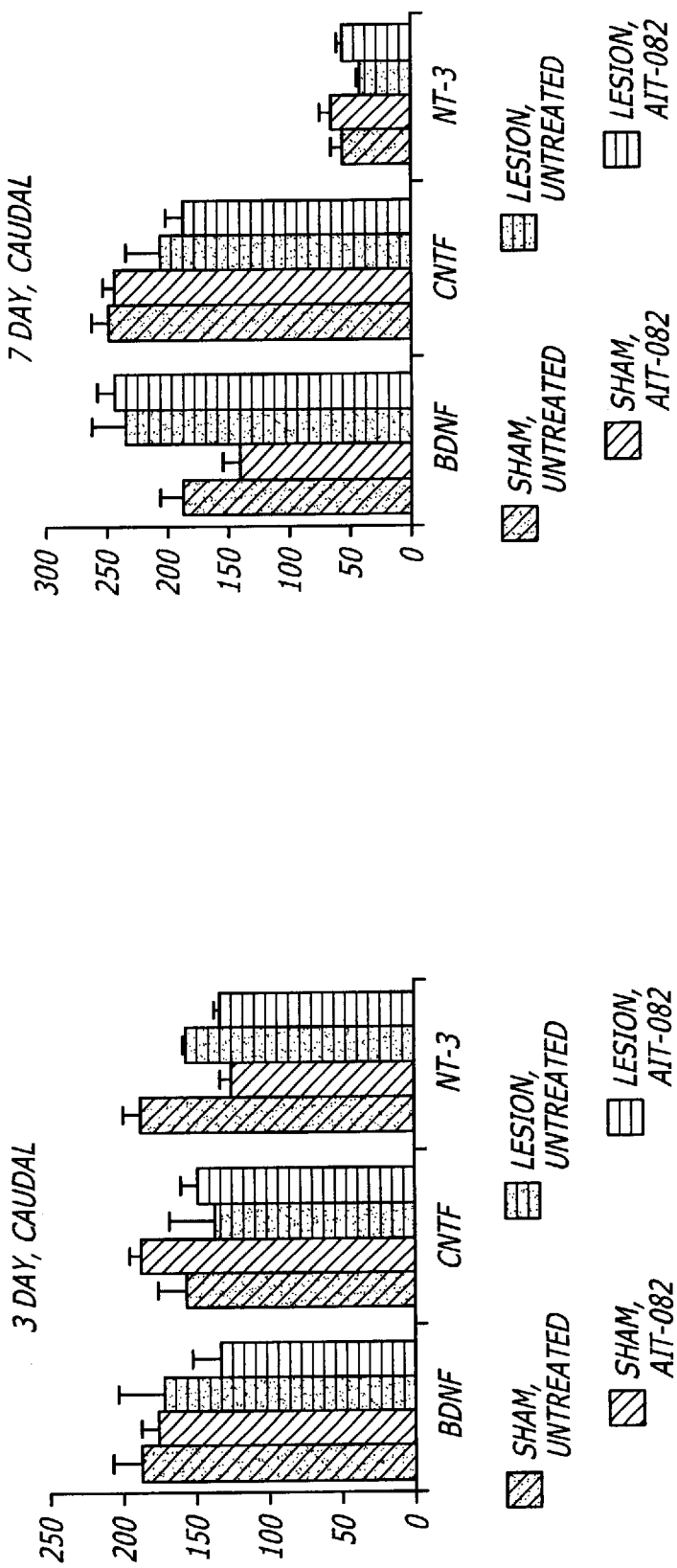
FIG. 43 is a graph of the levels of mRNA for BDNF, CNTF, and NT-3 caudal to the lesion for animals lesioned or sham-lesioned in Example 37: (a) levels measured 3 days after lesioning or sham-lesioning; (b) levels measured 7 days after lesioning or sham-lesioning.

The effects of the compound on levels of mRNA caudal to the lesion are shown in FIG. 43 (FIG. 43a, after 3 days of treatment; FIG. 43b, after 7 days of treatment). The mRNA levels were measured by RT-PCR on a 2 cm portion of the spinal cord I cm down from the T8 lesion site as indicated above. The animals were treated for 3 (FIG. 43a) or 7 days (FIG. 43b) as indicated. Statistical significance was determined by one-way Anova testing. Error bars represent S.E.M.s (n=3 or 4). The level of NT-3 mRNA was lower after treatment with the compound in sham-lesioned animals as compared with sham-lesioned animals not treated with the compound (p<0.05) after 3 days of treatment.

In conclusion, the compound appeared to suppress neuronal production of NT-3 at three days of treatment in the cords of control (sharn-lesioned) animals. While the effect was significant only in the segment caudal to the lesion, the trend was seen in all three segments of the cord. Seven days of treatment with the compound resulted in increased CNTF in the cords of control animals, though statistical significance was seen only in one segment. BDNF was markedly elevated in lesioned animals treated with the compound in the cord rostral to the lesion. The elevated expression seen in this segment may reflect the increased population of neuronal cells that were present at this level of the cord.

EXAMPLE 38

AIT-082 Effects on Neurotrophic Factor Production in the Brain

Studies in this example examine whether AIT-082: (1) promotes a survival of basal forebrain: cholinergic neurons after fimbria-fornix lesions; (2) influences the production of neurotrophic factors in the brain; and (3) influences cellular and neurotrophin changes in the aged brain. It was found that AIT-082 influences levels of the nervous system growth factors BDNF, GDNF, and NT-3 in specific regions of the brain under specific conditions.

Promotion of Survival of Basal Forebrain Cholinergic Neurons After Fimbria-Fomix Lesions by AIT-082

This model is the gold standard for examining the effects of neurotrophic factors, neurotrophic factor-releasing agents, and neurotrophic factor analogues in the central nervous system (CNS). Fimbria-fornix transections (FFT) are performed to induce the degeneration of basal forebrain cholinergic (BFC) neurons. In the absence of treatment, the number of BPC neurons is reduced to ~25% of normal numbers two weeks after the lesion, as identified by choline acetyltransferase (ChAT) immunolabeling or p75 (low affinity neurotrophin receptor) immunolabeling. The infusion of nerve growth factor completely prevents the degeneration of these neurons. In this experiment, animals received AIT-082 to determine whether it would prevent lesion-induced degeneration of BFC neurons.

Methods

Adult female F344 rats received an intraperitoneal (IP) injection of AIT-082 (30 mg/kg) or saline one hour prior to receiving a unilateral fimbria-fornix transection (FFT) (n=6 per group). All animals survived the surgery and continued to receive IP injections of AIT-082 or vehicle every three days following the lesion. All animals were perfused with fixative at 14 days post-lesion and brains were sectioned and processed for choline acetyltransferase (ChAT) and p75 immunoreactivity. For analysis, three sections, 240 $\mu$m apart, were taken at the level of the medial septum and ChAT positive cells were counted both ipsilateral and contralateral to the lesion.

Results

Figure 44:
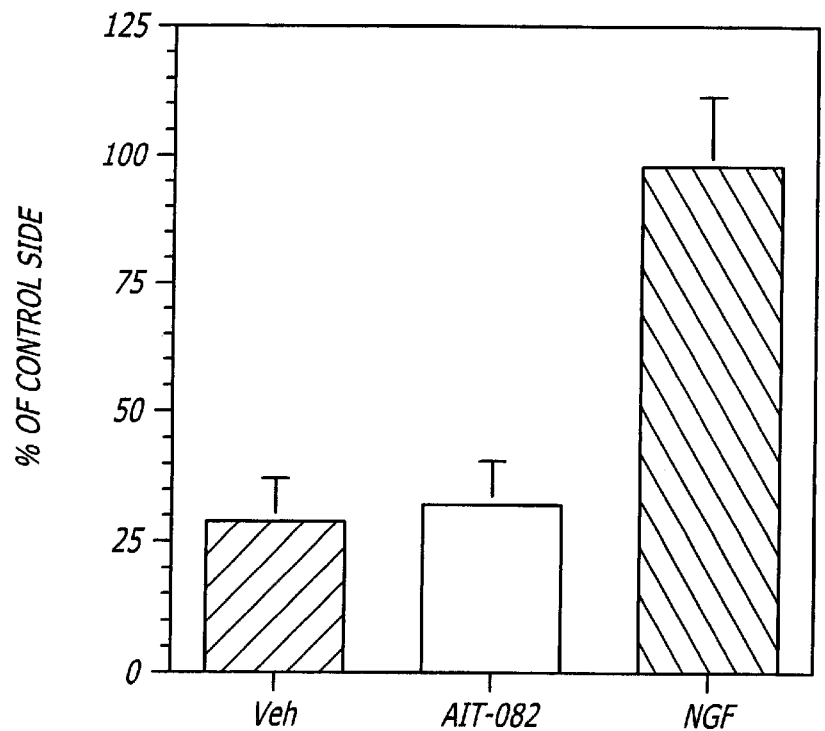
FIG. 44 is a graph showing the effect of AIT-082 treatment upon medial septum cholinergic neurons following fimbria-fornix transections.

Vehicle-infused control animals demonstrated a characteristic 70–75% loss of ChAT-positive cells on the side ipsilateral to the lesion. Administration of AIT-082 did not reduce lesion-induced loss of ChAT-labeled cells in the BFC region (FIG. 44). For the results of FIG. 44, ChAT-positive cells were counted in three sections, 240 $\mu$m apart. Data was expressed as a ratio of cell counts ipsilateral to the lesion divided by counts contralateral to the lesion. Animals were given intraperitoneal injections of either AIT-082 (30 mg/kg/day; n=6) or saline (n=6) every three days beginning on the day of the lesion. Injections were administered throughout the post-lesion survival interval of 14 days. No significant differences were seen in the number of ChAT positive cells on the lesion side as a result of the AIT-082 treatment. NGF data was obtained from Barnett et al. (*Exp. Neurol.* 110:11–24(1990)) using mouse NGF (25 $\mu$g/ml) and illustrates a robust rescue effect following the FFT lesion.

Influence of Neurotrophic Factors in the Brain by AIT-082

Previously it had been shown that AIT-082 influences expression of the growth factors NGF, neurotrophin-3 (NT-3) and fibroblast growth factor 2 (FGF-2 or bFGF) but not brain-derived neurotrophic factor (BDNF) in vitro and in vivo. Previous in vivo studies used RT-PCR, which is semi-quantitative and is not clearly related to levels of neurotrophin proteins in vivo. Therefore, it was determined whether AIT-082 upregulates NGF, BDNF, NT-3, and GDNF protein expression (by ELISA) in the brain and spinal cord.

Influence of AIT-082 on the Production of Neurotrophic Factors in the Intact Adult Brain.

Methods

Adult female F344 rats were given either AIT-082 (doses: 30 mg/kg/day or a higher dose of 30 mg/ml (~3,000 mg/kg/day); n=6 rats per group) in their drinking water, or water alone, as a vehicle for control. The duration of the study was seven days, at which time the rats were anesthesized and perfused with ice-cold saline. The brains of the rats were rapidly removed. The brains were placed on a chilled glass plate and dissected into the following regions: basal forebrain, frontal cortex, parietal cortex, cerebellum, spinal cord, and hippocampal formation. Tissues were stored at −70° C. until assayed in a specific two-site ELISA for either NGF, BDNF, NT-3, or GNDF.

Figure 45:
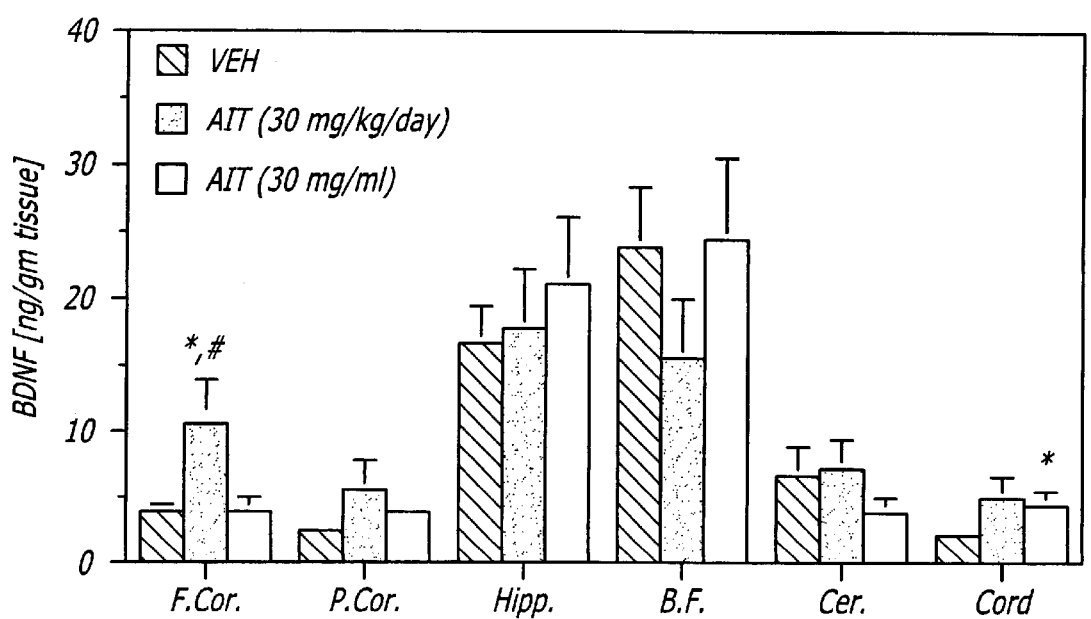
FIG. 45 is a graph showing the effect of AIT-082 treatment on BDNF protein levels in the intact adult rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)

The results are shown in FIGS. 45 (BDNF), 46 (NT-3), 47 (GDNF) and 48 (NGF). For the results shown in FIGS. 45–48, animals were given only water (VEH, n=6) or water with AIT-082 at either 30 mg/kg/day (n=6) or 30 mg/ml (n=6) for seven days. The levels of each growth factor were determined in the frontal cortex (F. Cor.), parietal cortex (P.Cor.), hippocampal formation (Hipp.), basal forebrain (B.F.), cerebellum (Cer.), or spinal cord (Cord) using a specific two-site ELISA for each growth factor. An asterisk (*) indicates that the results were significantly different ($p<0.05$) from vehicle-treated animals; a # sign indicates that the results were significantly different from animals treated with AIT-082 at 30 mg/ml ($p<0.05$).

All animals receiving the compound AIT-082, at high and low doses, appeared normal and showed no overt signs of weight loss during the one week of administration. AIT-082 at 30 mg/kg/day increased BDNF levels in frontal cortex more than twofold over vehicle controls (FIG. 45). This effect was not seen in animals treated with AIT-082 at 3000 mg/kg/day.

Figure 46:
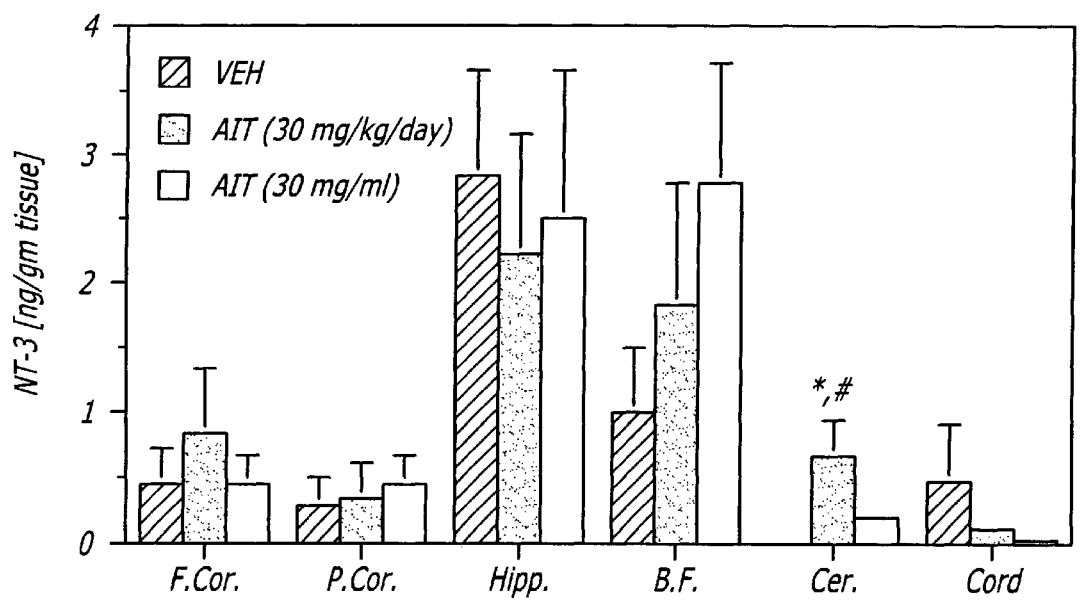
FIG. 46 is a graph showing the effect of AIT-082 treatment on NT-3 protein levels in the intact adult rat brain as measured by an ELISA assay as determined in the frontal cortex (F. Cor.), parietal cortex (P.Cor.), hippocampal formation (Hipp.), basal forebrain (B.F.), cerebellum (Cer.), or. spinal cord (Cord)
Figure 47:
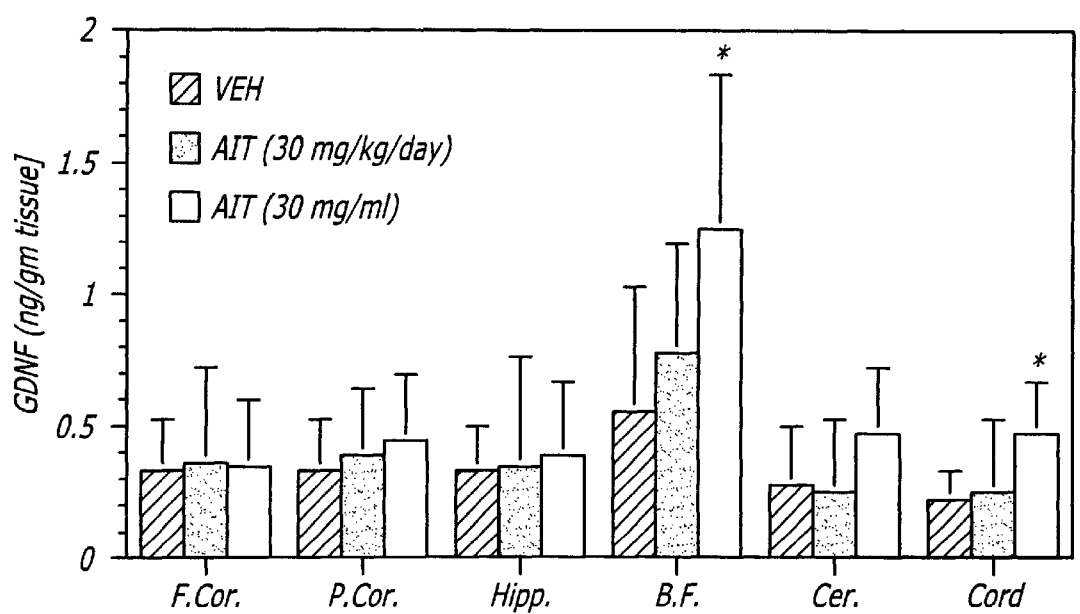
FIG. 47 is a graph showing the effect of AIT-082 treatment on GDNF protein levels in the intact adult rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)
Figure 48:
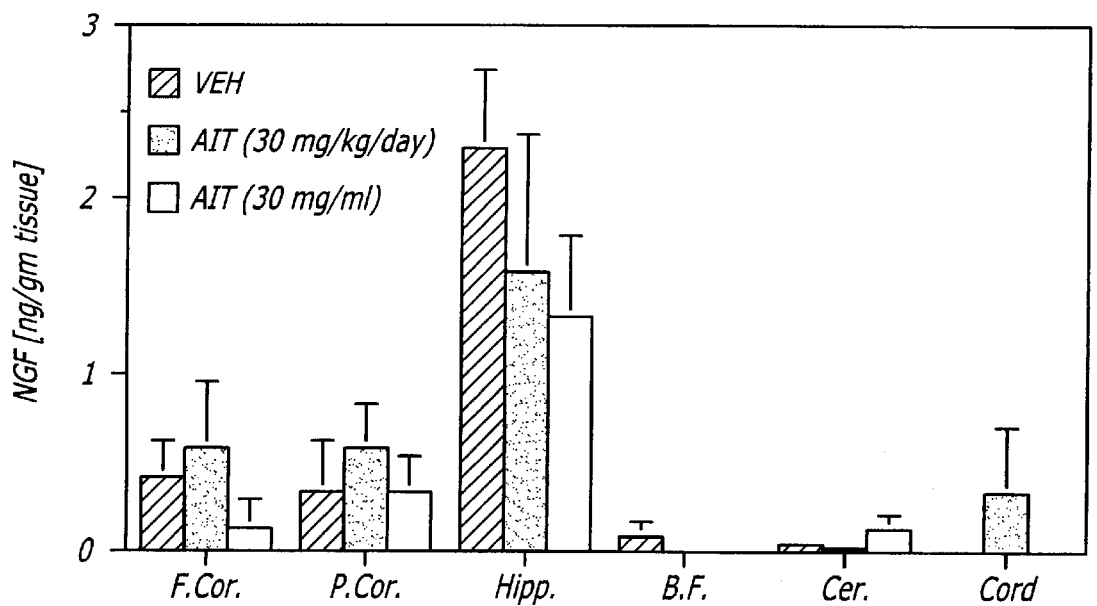
FIG. 48 is a graph showing the effect of AIT-082 treatment on NGF protein levels in the intact adult rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)

AIT-082 treatment also increased BDNF levels twofold in the spinal cord over vehicle controls, although this effect did not achieve significance ($p>0.05$). AIT-082 treatment of 30 mg/kg/day increased NT-3 levels in cerebellum over vehicle controls (FIG. 46). This effect was again absent in animals receiving 3000 mg/kg/day. AIT treatment (at 3000 mg/kg/day dose) increased GDNF levels in the basal forebrain and spinal cord above vehicle treated control levels (FIG. 47). No changes were seen in NGF levels as a result of the treatment (FIG. 48).

In conclusion, AIT-082 significantly elevated levels of three trophic factors in specific regions of the CNS when administered orally. BDNF levels increased in frontal cortex, a region implicated in Alzheimer's disease, and NT-3 levels increased in the cerebellum, a region implicated in several other neurological disorders of balance and coordination.

Modulation of Neurotrophic Factor Levels by AIT-082 in the Lesioned Adult Brain

Figure 49:
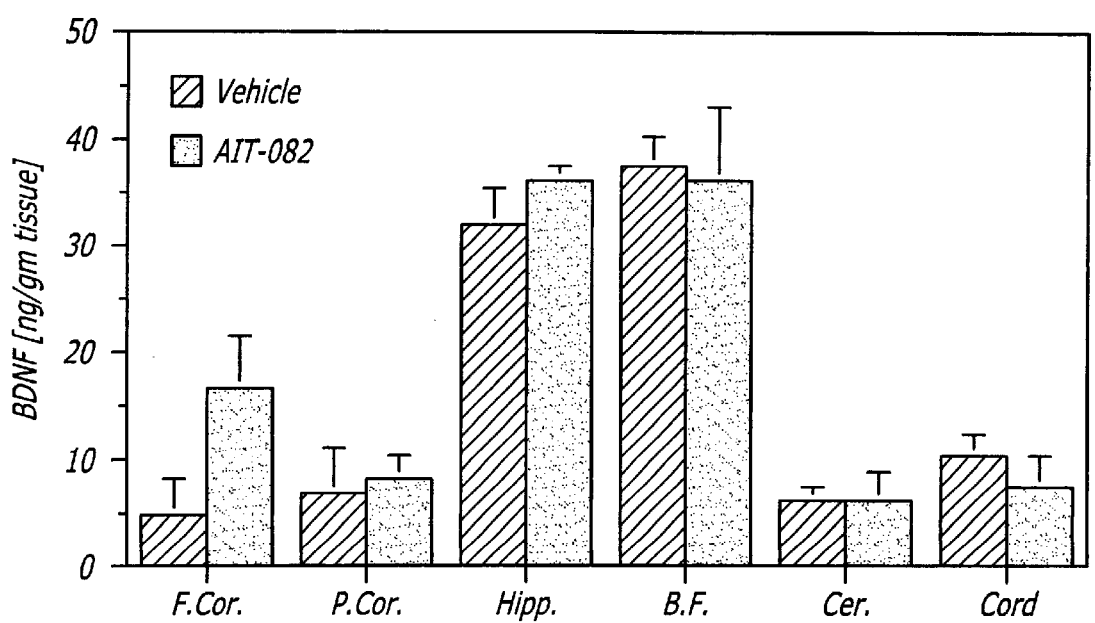
FIG. 49 is a graph showing the effect of AIT-082 treatment on BDNF protein levels in the fimbria-fomix transection-lesioned adult rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)

Most neurological disorders in which AIT-082 therapy would be administered represent conditions of neuronal injury. Expression of some growth factors is selectively increased after brain injury, suggesting that AIT-082 may be more effective at modulating growth factor activity under injured conditions. To explore this question, the experiment above was repeated in animals with lesions of BFC neurons.
Methods Adult female rats were given AIT-082 (30 mg/kg/day) in their drinking water or drinking water alone (n=6 for each group) for seven days prior to receiving a bilateral fimbria fornix transection (FFT).
Results The results are shown in FIGS. 49 (BDNF), 50 (NT-3), 51 (GDNF) and 52 (NGF). For the results shown in the Figures, animals were given only water (VEH, n=3) or water with AIT-082 at 30 mg/kg/day (n=3). Levels of the growth factor were determined in frontal cortex (F.Cor.), parietal cortex (P.Cor.), hippocampal formation (Hipp.), basal forebrain (B.F.), cerebellum (Cer.), or spinal cord (Cord) using a specific two-site ELISA for each growth factor. An asterisk (*) indicates a result significantly different from vehicle treated animals ($p<0.05$).

Figure 50:
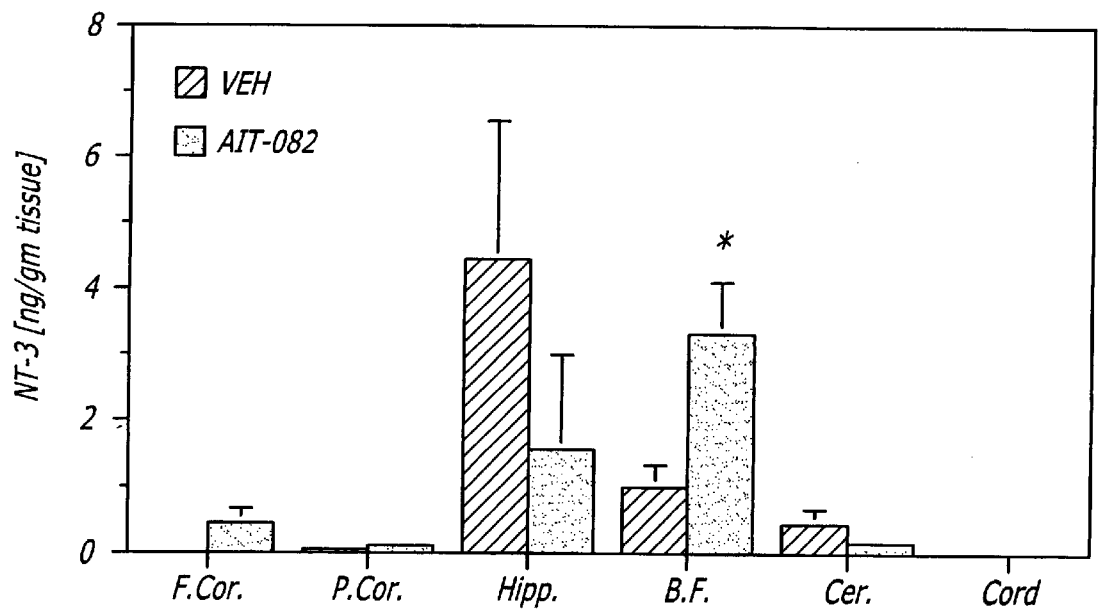
FIG. 50 is a graph showing the effect of AIT-082 treatment on NT-3 protein levels in the fimbria-fomix transection-lesioned adult rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)
Figure 51:
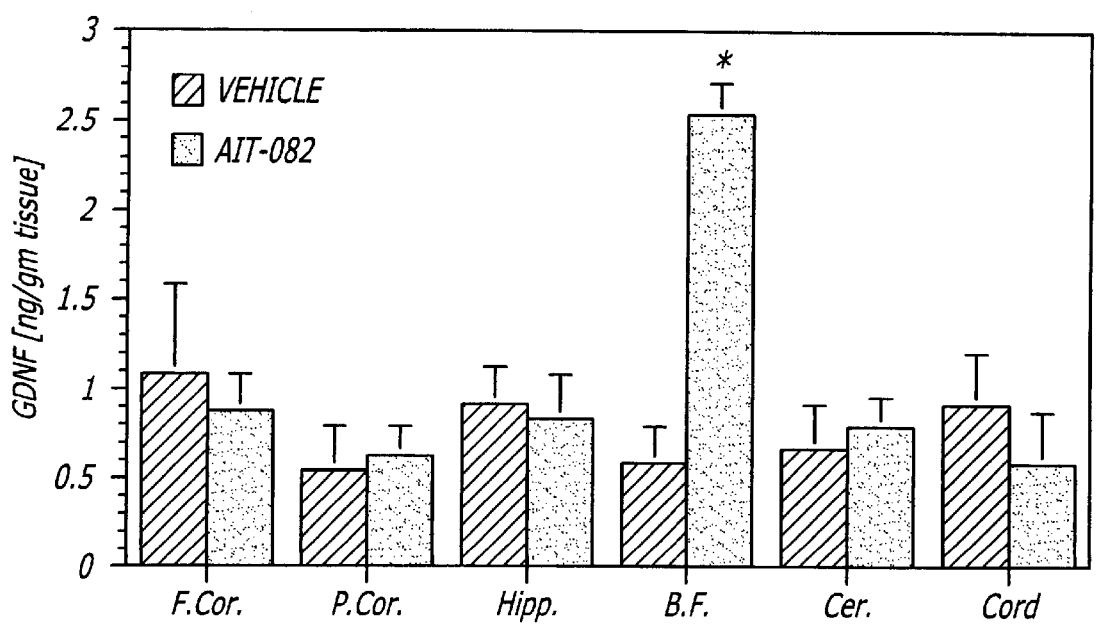
FIG. 51 is a graph showing the effect of AIT-082 treatment on GDNF protein levels in the fimbria-fornix transection-lesioned adult rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)
Figure 52:
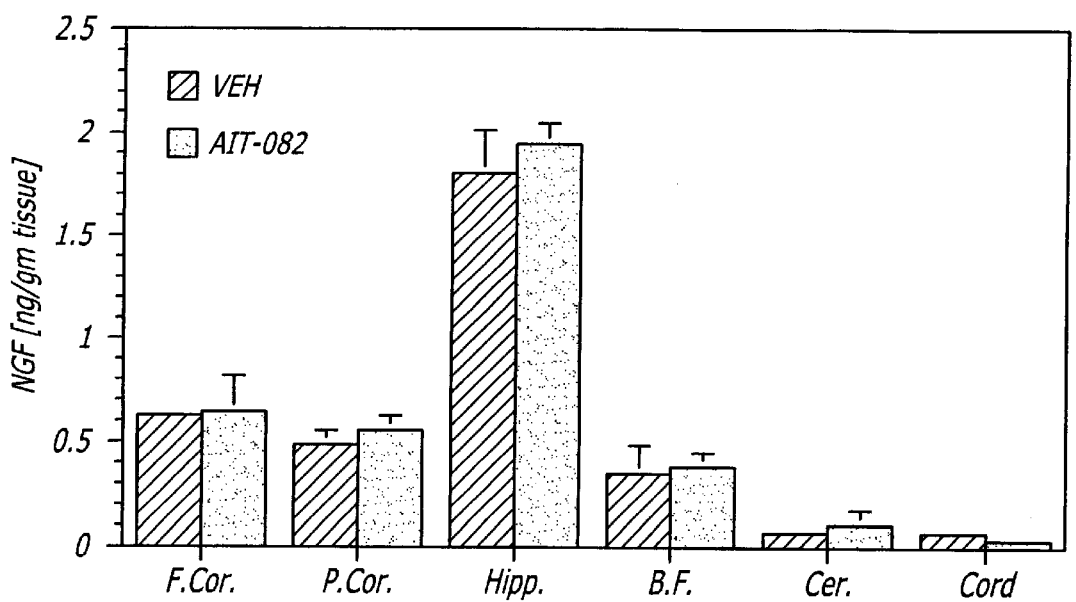
FIG. 52 is a graph showing the effect of AIT-082 treatment on NGF protein levels in the fimbria-fornix transection-lesioned adult rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)

AIT-082 treatment again increased levels of BDNF in frontal cortex almost threefold over vehicle controls (FIG. 49). However, statistical significance was not achieved at a high variability in BDNF levels. In addition, AIT-082 treated FFT-lesioned animals exhibited threefold increased in NT-3 levels within the basal forebrain compared to vehicle controls (FIG. 50). In the fimbria-fornix lesioned animals, AIT-082 treatment increased GDNF levels within the basal forebrain above vehicle controls (FIG. 51). No significant increases in NGF levels were found as result of the treatment (FIG. 52).

In conclusion, AIT-082 significantly elevates levels of two neurotrophic factors in specific regions of the injured CNS when administered orally. BDNF levels increase in frontal cortex, consistent with the results given above. This region is implicated in Alzheimer's disease. In addition, NT-3 and GDNF levels increase in the cholinergic basal forebrain, a region of substantial cell loss in Alzheimer's disease.

Influence of AIT on Cellular and Neurotrophin Changes in the Aged Brain

Previously, it has been shown that AIT-082 improves memory in aged rats and increases neurotrophin mRNA levels. Aging may represent a period of particular neuronal vulnerability to degeneration, including the changes of Alzheimer's disease. Thus, aged animals merit special independent study. This experiment examined AIT-082 induced alterations in neurotrophin levels in aged animals.
Methods Aged female Fischer 344 rats (obtained from National Institute on Aging; 24 months on arrival) were given AIT-082 (30 mg/kg/day) in their drinking water or drinking water alone, for a period of 30 days (n=5 rats per group). After 30 days, animals were sacrificed and fresh tissues were dissected as described above. An additional set of young animals (n=5) was processed along with the aged rats for comparison.

Figure 53:
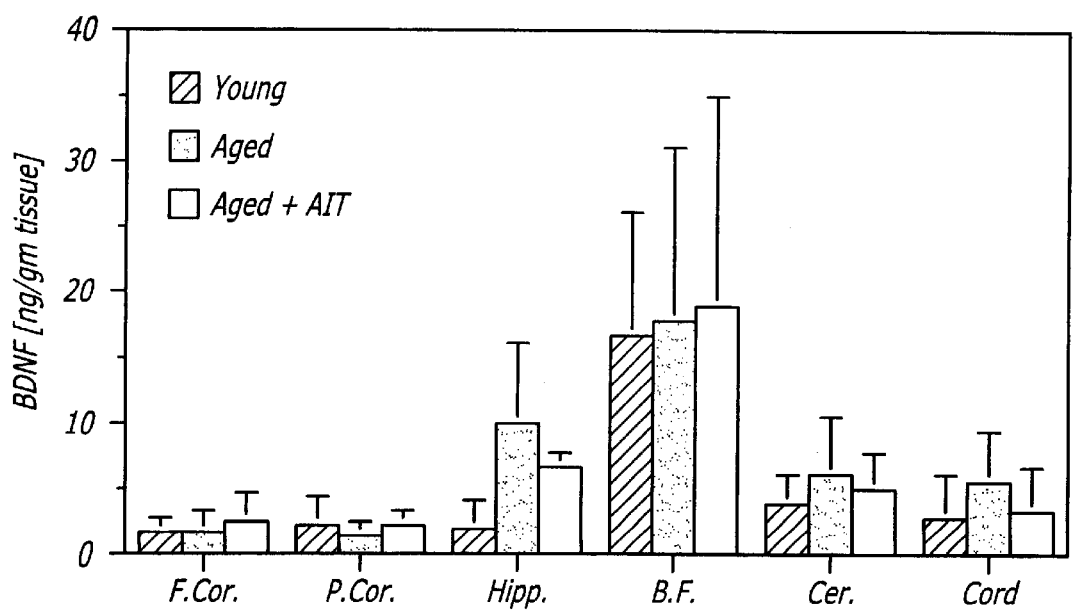
FIG. 53 is a graph showing the effect of AIT-082 treatment on BDNF protein levels in the intact aged rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)

Results are shown in FIGS. 53 (BDNF), 54 (NT3), 55 (GDNF), and 56 (NGF). As described above, for the results shown in these figures, aged rats (24 months of age) were given water (vehicle control; n=5) or water with AIT-082 (at 30 mg/kg/day; n=5 for 30 days). A separate group of young untreated animals was also included (n=5). Levels of each growth factor were determined in frontal cortex (F.Cor.), parietal cortex (P. Cor.), hippocampal formation (Hipp.), basal forebrain (B.F.), cerebellum (Cer.) or spinal cord (Cord) using a specific two-site ELISA. An asterisk (*) indicates that the results are significantly different from those with young animals ($p>0.05$); a # sign indicates that the results are significantly different from those with untreated aged animals ($p>0.05$).

Figure 54:
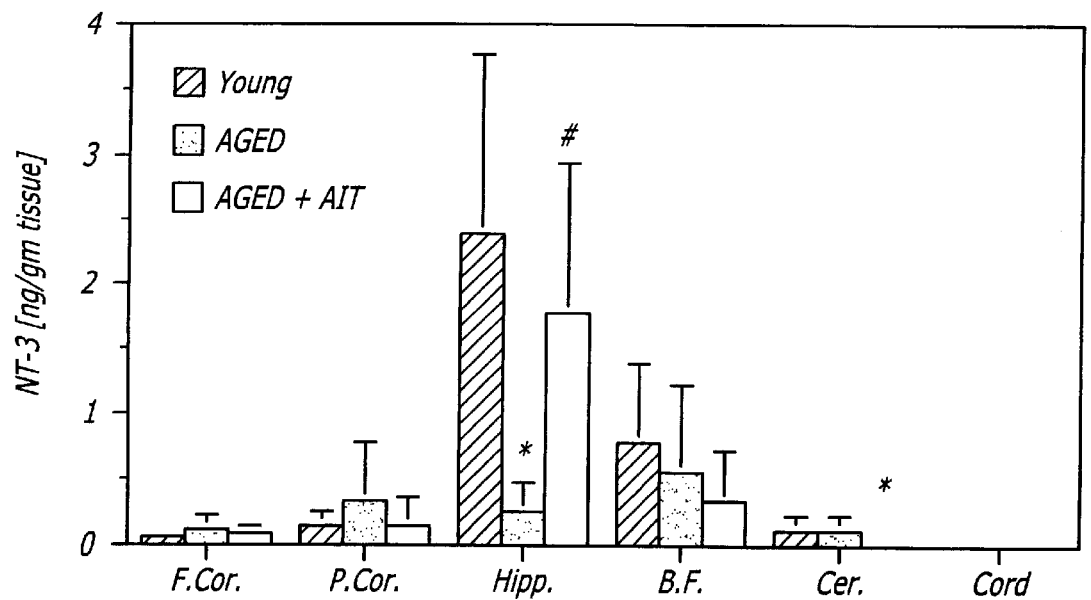
FIG. 54 is a graph showing the effect of AIT-082 treatment on NT-3 protein levels in the intact adult rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)
Figure 55:
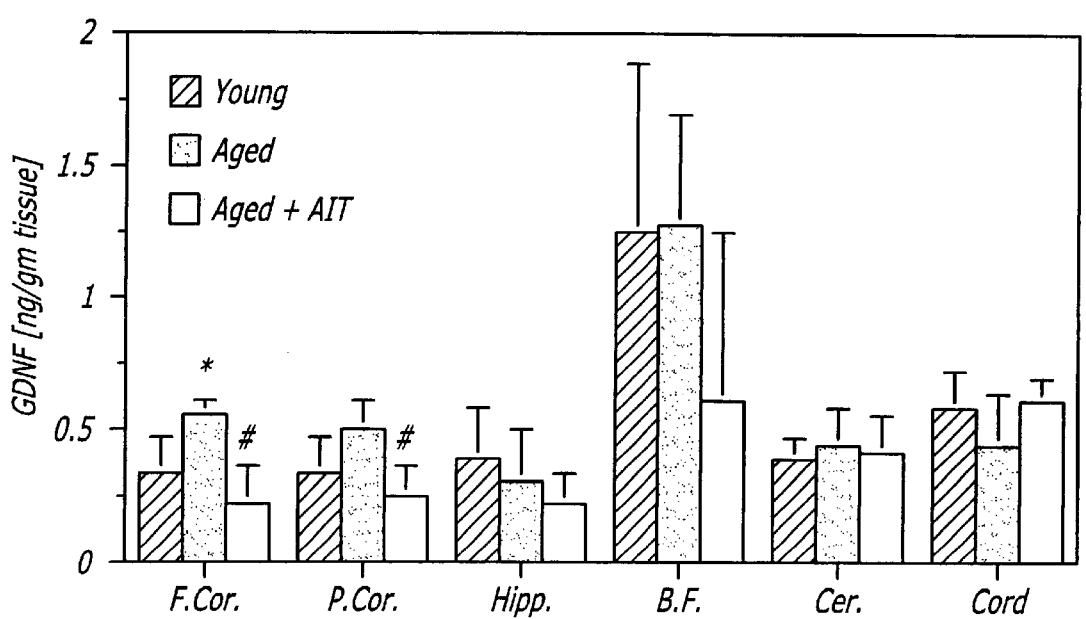
FIG. 55 is a graph showing the effect of AIT-082 treatment on GDNF protein levels in the intact adult rat brain as measured by an ELISA assay as determined in the frontal cortex (F. Cor.), parietal cortex (P.Cor.), hippocampal formation (Hipp.), basal forebrain (B.F.), cerebellum (Cer.), or spinal cord (Cord)
Figure 56:
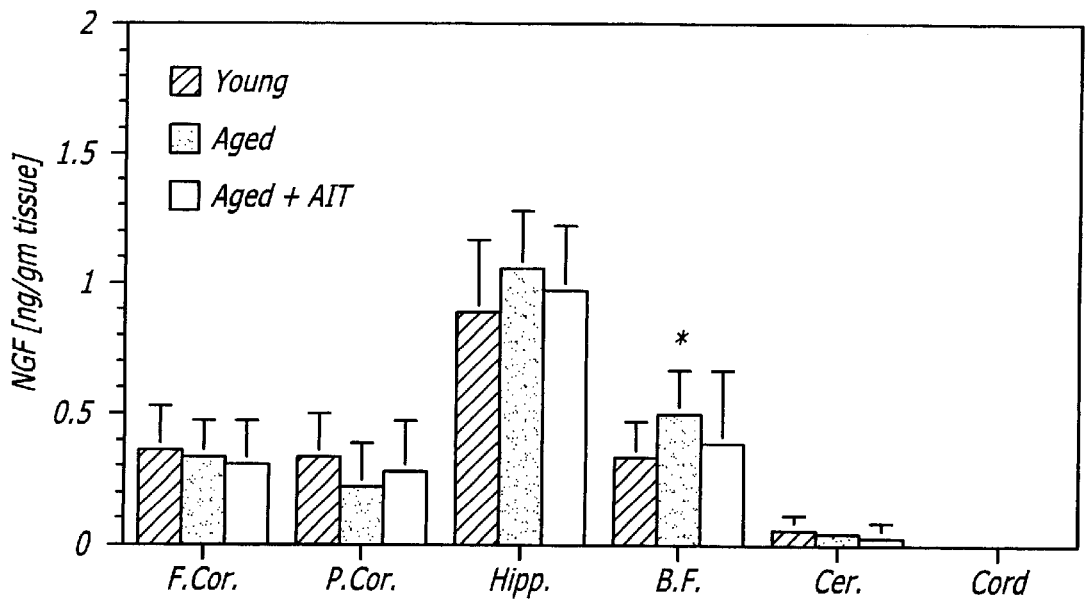
FIG. 56 is a graph showing the effect of AIT-082 treatment on NGF protein levels in the intact adult rat brain as measured by an ELISA assay as determined in the frontal cortex (F. Cor.), parietal cortex (P .Cor.), hippocampal formation (Hipp.), basal forebrain (B.F.), cerebellum (Cer.), or spinal cord (Cord)

Within the hippocampus, there was a significant age-related decline in NT-3 levels of aged control animals compared to young animals. Significantly, AIT-082 treatment restored NT-3 protein levels to those of young animals (FIG. 54). Slight increases in GDNF levels were noted in the parietal and frontal cortex as a result of aging; however, AIT-082 treatment restored GDNF protein levels to those of young animals (FIG. 55). AIT-082 treatment in the aged animal had no effect on BDNF (FIG. 53) or NGF (FIG. 56)

in any of the brain regions examined. In conclusion, AIT-082 reversed age-related declines in hippocampus NT-3 levels. The hippocampus is predominantly involved in Alzheimer's disease.

Generally, in conclusion, this data indicates that AIT-082 can increase neurotrophin levels in specific brain regions. Although AIT-082 failed to show a neuroprotective effect in the fimbria-fornix model, neuronal degeneration in the fimbria-fornix model is most sensitive to NGF. Of the growth factors assayed, AIT-082 influenced BDNF, NT-3, and GDNF levels but not those of NGF, thereby potentially accounting for the lack of neuroprotection in the fimbria-fornix model.

A compound that can be administered orally to modulate neurotrophic factors in the CNS is an important finding and generally supports several previous in vitro and in vivo studies performed with AIT-082. Findings of the study of this Example suggest a mechanistic basis for the neuroprotective actions of AIT-082, by demonstrating specific increases in levels of BDNF, NT-3, and GDNF as the result of treatment. In particular, AIT-082 increases BDNF protein levels in the frontal cortex, a brain region thought to play an important role in several cognitive tasks. Further, BDNF has been shown in previous studies to modulate synaptic plasticity, which could enhance cognition.

The finding that AIT-082 augments NT-3 in the hippocampus supports its potential utility in Alzheimer's disease. Further, the finding that NT-3 levels are also increased in the cerebellum broadens the potential therapeutic targets of AIT-082.

Levels of the potent motor neuron and dopaminergic neuron growth factor GDNF were also significantly enhanced in this study in the brain stem and spinal cord. These findings raise a possibility that AIT-082 may be of therapeutic benefit in Parkinson's disease (the second most common neurodegenerative disorder), amyotrophic lateral sclerosis (Lou Gehrig's disease), and spinal cord injury.

EXAMPLE 39

Production of Neurotrophic Factors Stimulated by AIT-082 in Rat Cultured Astrocytes Guanine-based purines, released in large amounts from astrocytes (Ciccarelli et al., *Glia* 25: 93–98 (1999)) have been recently recognized as extracellular signaling molecules, able to exert important trophic effects on both neurons and glia (Rathbone et al., *Drug Dev. Res.* 45: 356–372 (1998)). The hypoxanthine derivative AIT-082, also known as N-4-carboxyphenyl-3-(6-oxohydropurin-9-yl)propanamide or 4-(3-(1,6-dihydro-6-oxo-9-purin-9-yl)-1-oxopropyl)amino) benzoic acid, shares some trophic effects with guanine-based purines in vitro. Moreover, AIT-082, administered in vivo, restores age- and experimentally-induced working memory deficits in rodents (Glasky et al., *Pharm. Biochem. Behav.* 47: 325–329 (1994)). In these activities, the production of neurotrophic factors (NFs) could be involved (Middlemiss et al., *Neurosci. Lett.* 199: 1–4 (1995)).

Today, NFs are considered as potential drugs for the experimental therapy of neurodegenerative disorders of the brain, owing to their capability of enhancing neuronal recovery and survival. However, the clinical potential of NFs is undermined by their inability to cross the blood-brain barrier and by their induction of severe side effects after systemic administration. Thus, one possible therapeutic approach is to induce a drug-mediated increase in the local production of endogenous NFs in the brain, assuming astrocytes as target cells that produce large amounts of either neurotrophins (nerve growth factor (NGF), brain-derived neurotrophic factor (BDNF), neurotrophin-3 (NT-3), or neurotrophin 4/5 (NT-4/5)) or pleiotrophins (transforming growth factor β (TGFβ), fibroblast growth factors (FGFs), or S100β protein).

In the studies reported in this Example, it was investigated whether: (1) AIT-082, like guanosine, stimulated the production of some NFs such as NGF or TGFβ from rat cultured astrocytes; and (2) whether the NFs released from cultured astrocytes following AIT-082 stimulation were protective against excitotoxic damages caused by NMDA in cultured neurons.

Figure 57:
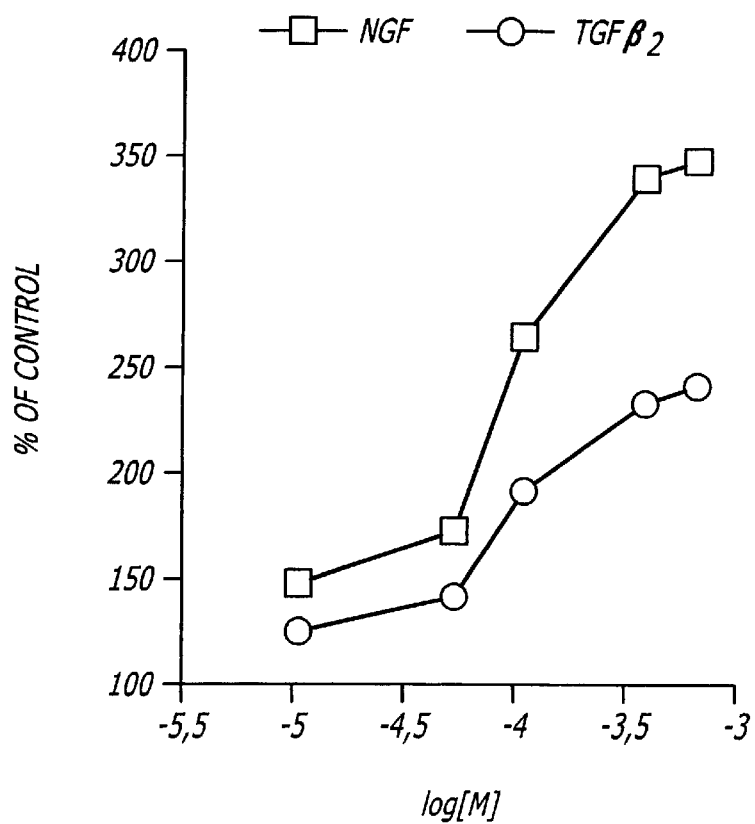
FIG. 57 is a graph showing the dose response of NGF and $TGF\beta_2$ from rat cultured astrocytes as induced by guanosine.

The dose response of NGF and $TGF\beta_2$ from rat cultured astrocytes as induced by guanosine is shown in FIG. 57 The exposure of astrocytes to guanosine for 24 hours caused a dose-dependent increase of the release of NGF and $TGF\beta_2$. NGF and $TGF\beta_2$ levels were assayed in the culture medium of the astrocytes by specific ELISA assays using kits from Roche (Germany) and Promega (USA) respectively. NGF basal levels were 56.3±3.2 pg/ml. $TGF\beta_2$ levels were 9.1±0.06 pg/ml.

Figure 58A:
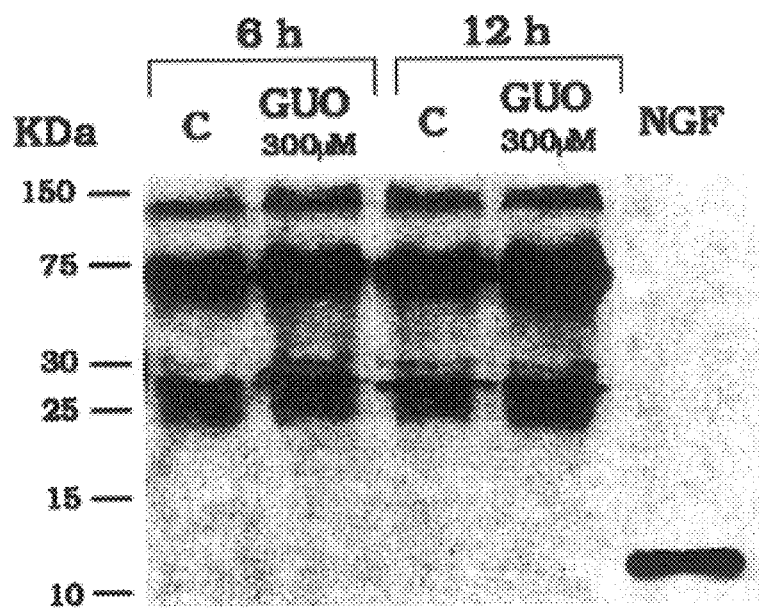
FIG. 58 is a gel electropherogram showing Western blot analysis of cytosolic proteins from cultured astrocytes to detect production of NGF and $TGF\beta_2$ from rat cultured astrocytes as induced by guanosine: (A) NGF; (B) $TGF\beta_2$.
Figure 58B:
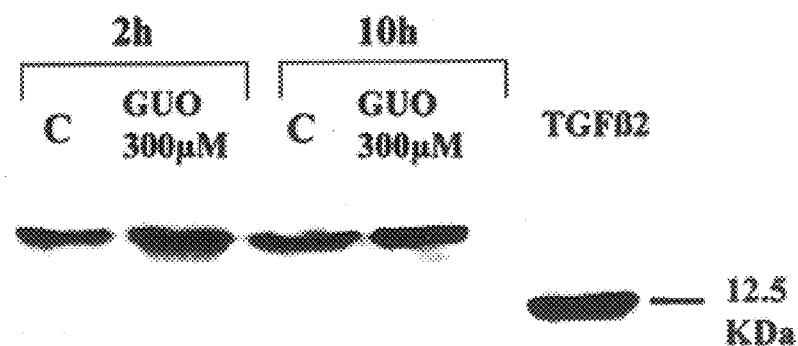

Western blot analysis of cytosolic proteins from cultured astrocytes was performed to detect the factors NGF and $TGF\beta_2$. The results are shown in FIG. 58A for NGF at 6 and 12 hours and in FIG. 58B for $TGF\beta_2$ at 6 and 12 hours. These results indicate that guanosine increased the intracellular content of NGF and $TGF\beta_2$ in time-dependent fashion.

The results shown in FIGS. 59A and 59B show the involvement of the mitogen-activated protein kinase cascade and ex novo protein synthesis in the guanosine-induced effect. In FIG. 59A, the effect of two inhibitors of the mitogen-activated protein kinase cascade, wortmannin and PD098,059, is shown. In the results shown in this figure, 100 nM wortmannin or 10 μM PD098,059 were added to the cultures 30 minutes before guanosine and maintained for 24 hours together with 300 μM guanosine. In FIG. 59B, the effect of the protein synthesis inhibitor cycloheximide (CHX) is shown. In the results shown in this figure, the CHX was added to the cultures 30 minutes before guanosine and maintained for 24 hours together with 300 μM guanosine. The effects of MAP kinase inhibitors or protein synthesis inhibitor are expressed as % of the effect caused by guanosine on NGF and $TGF\beta_2$ release assumed as equal to 100%.

Figure 60:
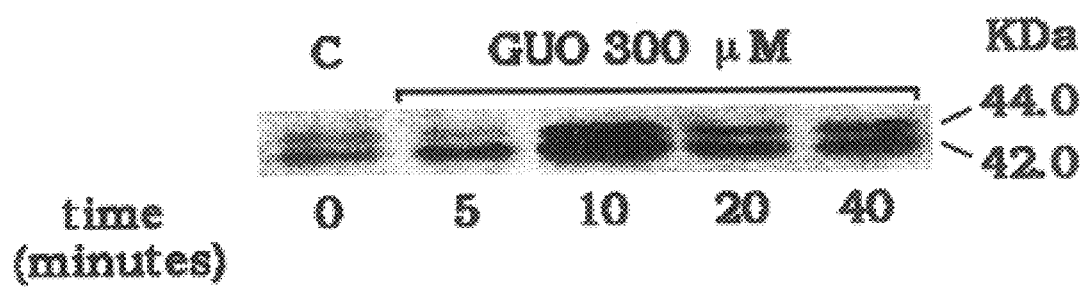
FIG. 60 is a gel electropherogram of a Western blot showing the activation of MAP kinases ERK1 (44 kDa) and ERK2 (42 kDa) by guanosine.

In FIG. 60, the activation of MAP kinases ERK1 (44 kDa) and ERK2 (42 kDa) by guanosine is shown. Cultured astrocytes were harvested at 4° C. in lysis buffer specific for MAP kinase: 25 mM Tris buffer, pH 7.4, containing 150 mM NaCl, 100 μM sodium orthovanadate, 1.5 mM $MgCl_2$, 1.0 mM EDTA, 1% NP40, 10% glycerol, 1 mM PMSF, 5 μg/ml leupeptin, and 10 μg/ml aprotinin and sonicated and centrifuged at 14,000 rpm for 5 min. Aliquots of the supernatants were processed for the assessment of protein concentration (M. M. Bradford, "A Rapid and Sensitive Method for the Quantitation of Microgram Quantities of Protein Using the Principle of Protein-Dye Binding," *Anal. Biochem.* 72: 248–254 (1976)). Electrophoresis was performed in 12% SDS-PAGE, using 20 μg of total protein per lane and separated proteins were then transferred onto a PVDF membrane (Bio-Rad Laboratories, Italy). Membranes were first incubated with polyclonal primary antibody (rabbit phospho-ERK1/2 antibody, New England Biolabs, Germany; final dilution 1:1000) for 1 hour and then with donkey anti-rabbit HPR-conjugated secondary antibody (Amersham, Italy; final dilution 1:5000) for another 1 hour, both at room temperature. Immunocomplexes were visualized using the enhancing chemiluminescence detection system (ECL) (Amersham, Italy).

Figure 61:
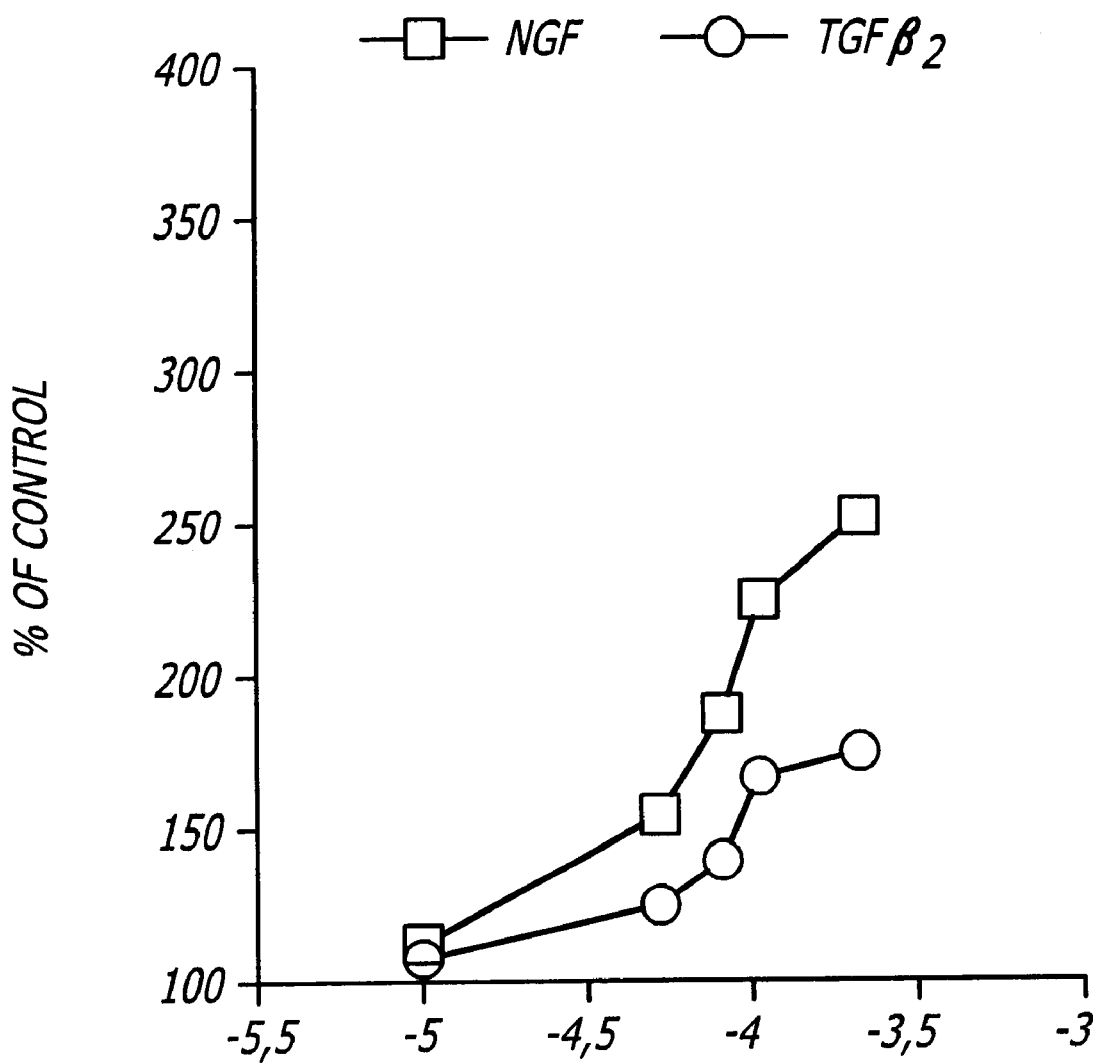
FIG. 61 is a graph showing the dose-response curves of NGF and $TGF\beta_2$ release from rat cultured astrocytes as the result of exposure to AIT-082.

In FIG. 61, the dose-response curves of NGF and TGFβ$_2$ release from rat cultured astrocytes as the result of exposure to AIT-082 are shown. NGF and TGFβ$_2$ levels were measured in the same manner as for the results shown in FIG. 57. The results indicated that AIT-082 caused a time-dependent increase of NGF production by about 2.5-fold and TGFβ$_2$ production by 1.7-fold, as compared to a control.

Figure 62A:
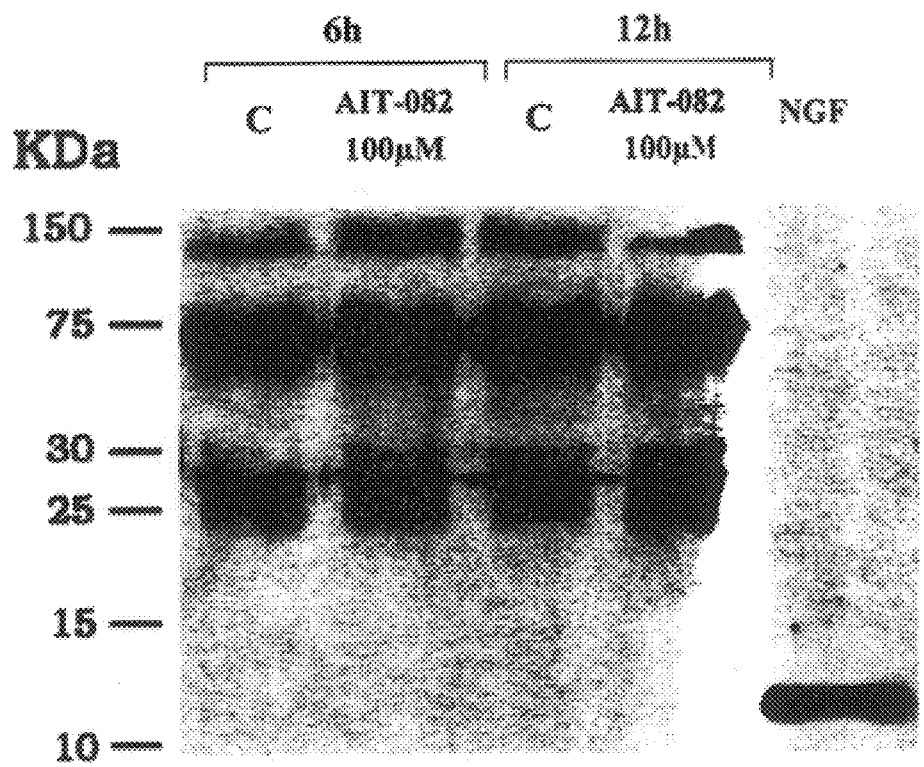
FIG. 62 is a gel electropherogram of a Western blot showing the stimulation of synthesis of NGF and $TGF\beta_2$ by AIT-082.
Figure 62B:
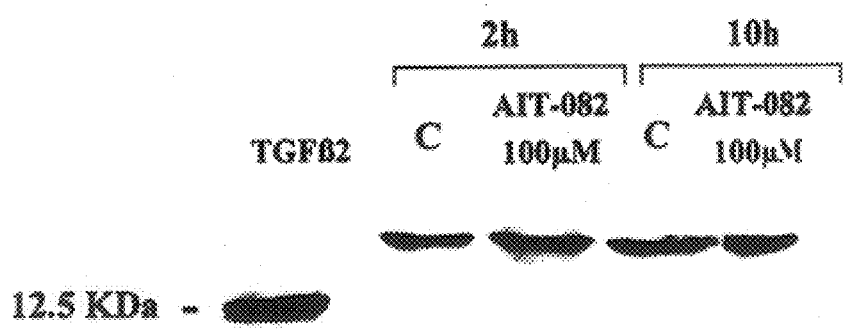

Western blot analysis of cytosolic proteins deriving from cultured astrocytes treated for 6 or 12 hours with 100 μM AIT-082 was performed. AIT-082 is able to promote the production of neurotrophic factors from rat cultured astrocytes as measured by Western blot analysis. The results are shown in FIG. 62A for NGF and in FIG. 62B for TGFβ$_2$. Electrophoresis was performed in 12% (for NBF) or 15% (for TGFβ$_2$) SDS-PAGE (20 μg of total protein per lane). The separated proteins were transferred onto a PVDF membrane (Bio-Rad Laboratories, Italy). Membranes were incubated (1 hr) with polyclonal primary antibody (rabbit anti-NGF, Santa Cruz Biotechnology, CA; final dilution, 1:100; rabbit anti-TGFβ$_2$, Santa Cruz Biotechnology; final dilution 250 ng/ml) and then with donkey anti-rabbit HRP-conjugated secondary antibody (Amersham, Italy; final dilution 1:5000 (1 hr), both at room temperature. Immunocomplexes were visualized by the enhancing chemiluminescence detection system (ECL). AIT-082 (100 μM) increased in time-dependent manner the intracellular levels of both trophins.

Moreover, at the same dose, AIT-082 did not stimulate ex novo synthesis of S100β protein. This finding confirmed previous data obtained by ELISA assay on astrocyte culture medium, demonstrating that AIT-082 increased only early release of this pleiotrophin from astrocytes into the culture medium.

Figure 63:
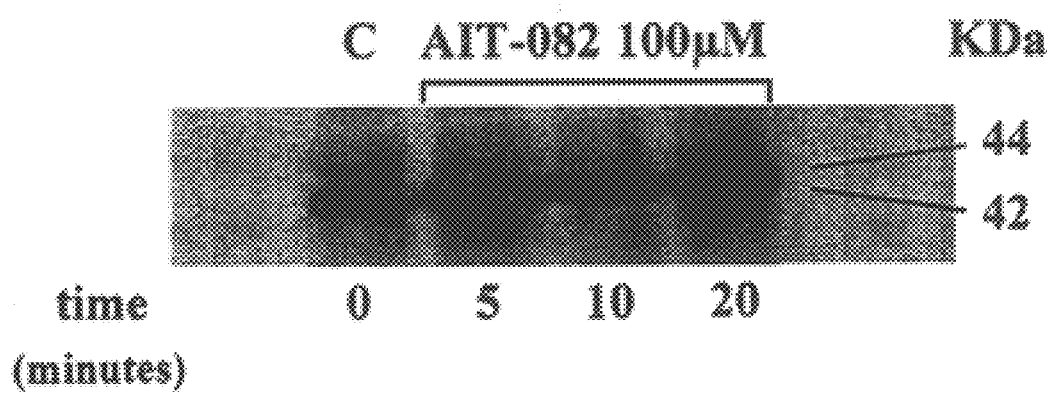
FIG. 63 is a gel electropherogram of a Western blot showing the activation of MAP kinases ERK1 (44 kDa) and ERK2 (42 kDa) by AIT-082.

At the same time, it was found that AIT-082, at its most active dosage (100 μM) induced, 5 min after the exposure of cultured astrocytes, the maximal activation of the molecular enzyme cascade. This activation was no longer evident after 10 minutes or 20 minutes of stimulation. In particular, by a selective Western blot analysis, it was found that AIT-082 stimulated the phosphorylation of MAP kinases ERK1 (44 kDa) and ERK2 (42 kDa), corresponding to the activated isoforms of the enzymes, in astrocyte cytosolic proteins. This effect is likely independent of the activity of growth factors, such as NGF, that also act through this molecular pathway. These results are shown in FIG. 63. Cultured astrocytes were harvested at 4° C. in lysis buffer specific for MAP kinase: 25 mM Tris buffer, pH 7.4, containing 150 mM NaCl, 100 μM sodium orthovanadate, 1.5 mM MgCl$_2$, 1.0 mM EDTA, 1% NP40, 10% glycerol, 1 mM PMSF, 5 μg/ml leupeptin, and 10 μg/ml aprotirin and sonicated and centrifuged at 14,000 prm for 5 min. Aliquots of the supernatants were processed for the assessment of protein concentration (Bradford, 1976). Electrophoresis was performed in 12% SDS-PAGE, using 20 pg of total protein per lane and separated proteins were then transferred onto a PVDF membrane (Bio-Rad Laboratories, Italy). Membranes were first incubated with polyclonal primary antibody (rabbit phospho-ERK1/2 antibody, New England Biolabs, Germany; final dilution 1:1000) for 1 hour and then with donkey anti-rabbit HPR-conjugated secondary antibody (Amersham, Italy; final dilution 1:5000) for another 1 hour, both at room temperature. Immunocomplexes were visualized using the enhancing chemiluminescence detection system (ECL) (Amersham, Italy).

Figure 64:
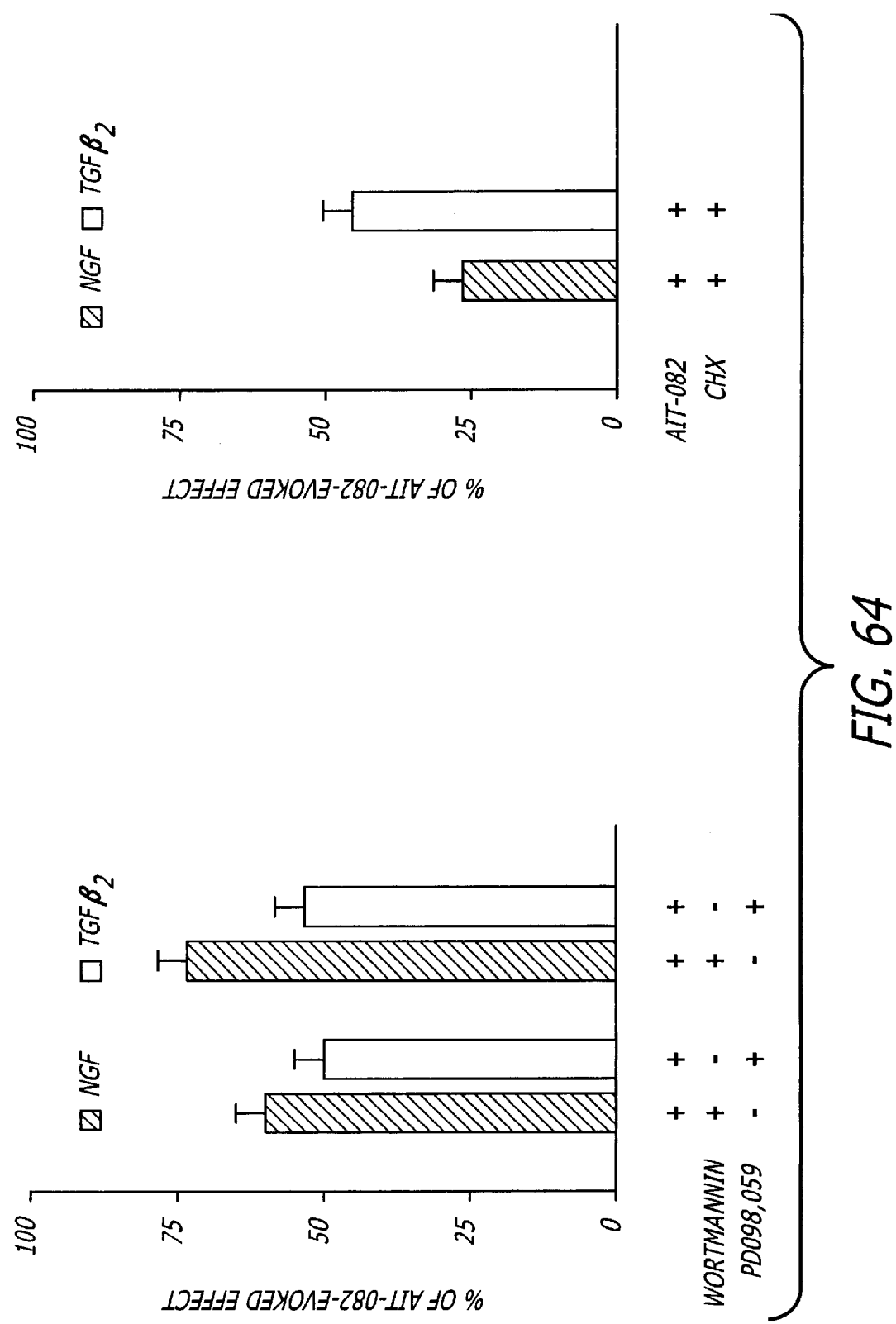
FIG. 64 is a graph showing the effect of the MAP kinase cascade inhibitors wortmannin and PD098,059 or the protein synthesis inhibitor cycloheximide on the effect of AIT-082: wortmannin and PD098,059 (left panel); cycloheximide (right panel)

The AIT-082-induced accumulation of both trophins, mainly that of NGF, was partly inhibited by the pretreatment of the culture with wortmannin, an inhibitor of phosphatidyl inositol 3-kinase, an enzyme involved in MAP kinase cascade activation by G-protein coupled receptors, or PD098,059, an inhibitor of MAP kinase kinase activity as well as by a known inhibitor of protein synthesis, cycloheximide (CHX). The results with these inhibitors are shown in FIG. 64. In these experiments, 100 nm wortmannin or 10 μM PD098,059 or 500 ng/ml CHX were added to the cultures 30 min before AIT-082 and maintained for 24 hours together with 100 μM AIT-082. The effects of the MAP kinase inhibitors (left panel) or cycloheximide (right panel) are expressed as % of the effect caused by AIT-082 on NGF or TGFβ$_2$ release assumed as equal to 100%.

It was next evaluated whether the addition of conditioned medium (CM) deriving from astrocyte cultures treated with 100 μM AIT-082 generated protection against damage induced by a toxic pulse with 100 μM NMDA in cultured neurons. Previously, it was demonstrated that the addition of CM, obtained as indicated above, was protective against NMDA-induced toxicity in hippocampal neurons. This protective effect was ascribed mainly to NGF production caused by astrocyte treatment with AIT-082. Indeed, if the astrocyte-derived CM was added to hippocampal neurons together with specific NGF-neutralizing antibodies or TGFβ$_2$-neutralizing antibodies, a significant reduction of the protective effect was observed. In further experiments, the co-addition of CM and specific antibodies to S100β protein (100 ng/ml) to NMDA-damaged hippocampal neurons did not modify CM-induced neuroprotection.

In these experiments, cultured neurons were prepared from rat cerebral cortex. In these cultures the NMDA pulse (100 μM for 10 min) provoked about 80% neuronal death (measured by Trypan blue cell staining or LDH activity). Separately, cultured astrocytes were treated for 6 hours with AIT-082. Then, the medium containing the drug was replaced with fresh medium without the drug and the astrocyte cultures were maintained in this medium for the next 24 hours. This medium represented the CM and was added to neurons soon after the toxic pulse with NMDA. The addition of CM partly counteracted the toxic effects caused by NMDA, reducing the neuronal damage by about 50%. If the medium was boiled for 20 min at 100° C. prior to addition to NMDA-damaged neurons, it completely lost the protective activity. This finding suggested that the AIT-082-induced protection was likely mediated through a heat-sensitive factor, likely a protein. To verify whether the neuroprotection caused by AIT-082 was ascribable to the production of TGFβ$_2$ or NGF, antibodies to TGFβ$_2$ or to NGF (100 ng/ml) were added together with CM. This treatment also reduced the neuroprotective effect of the CM by about 40%.

Figure 65:
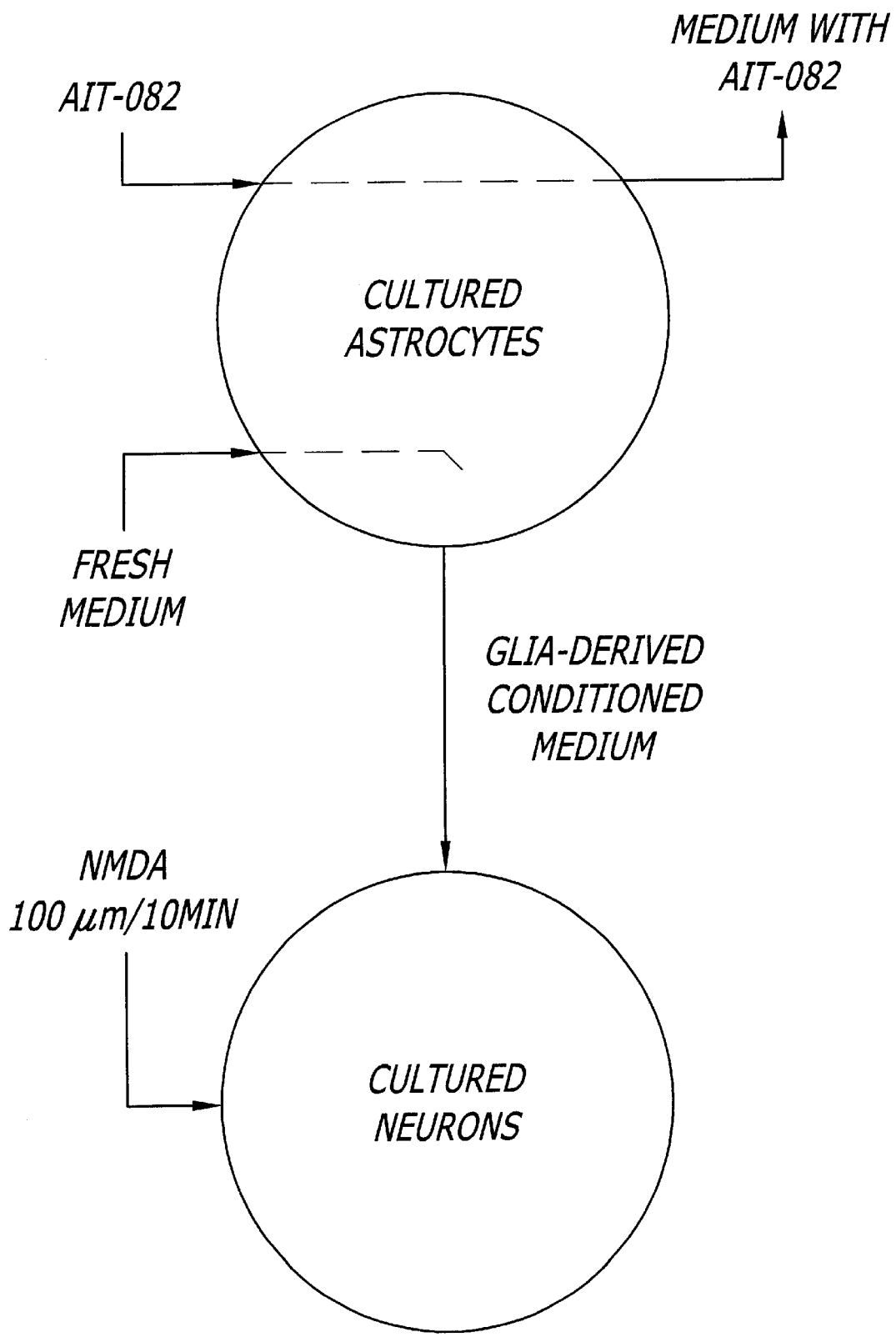
FIG. 65 is a graph showing the experimental scheme for the use of conditioned medium (CM)
Figure 66A:
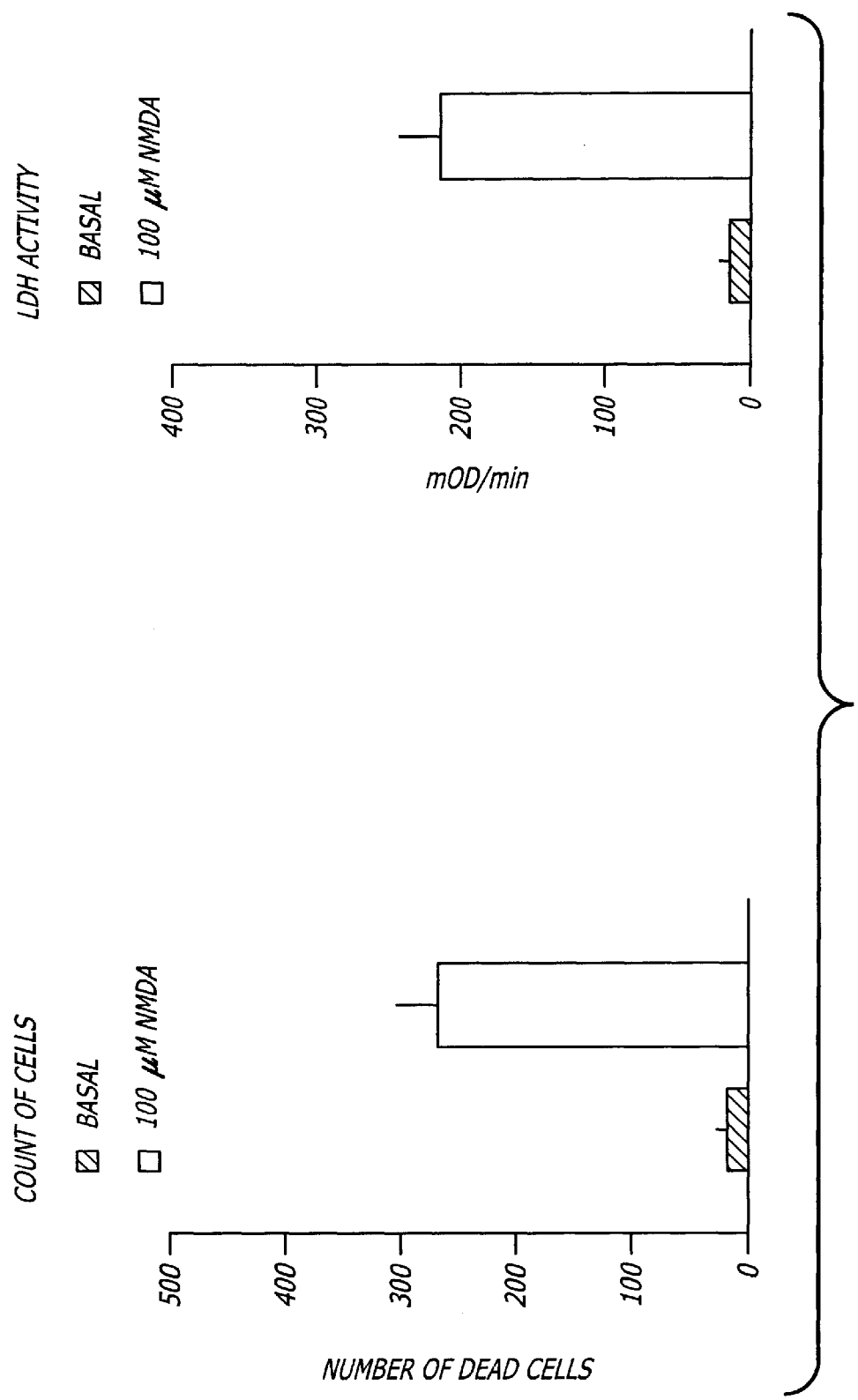
FIG. 66 is a graph showing the effects of NMDA on cortical cells (A) or hippocampal cells (B) as demonstrated by count of dead cells as measured by Trypan Blue staining (left panel) and also by release of LDH activity (right panel)
Figure 66B:
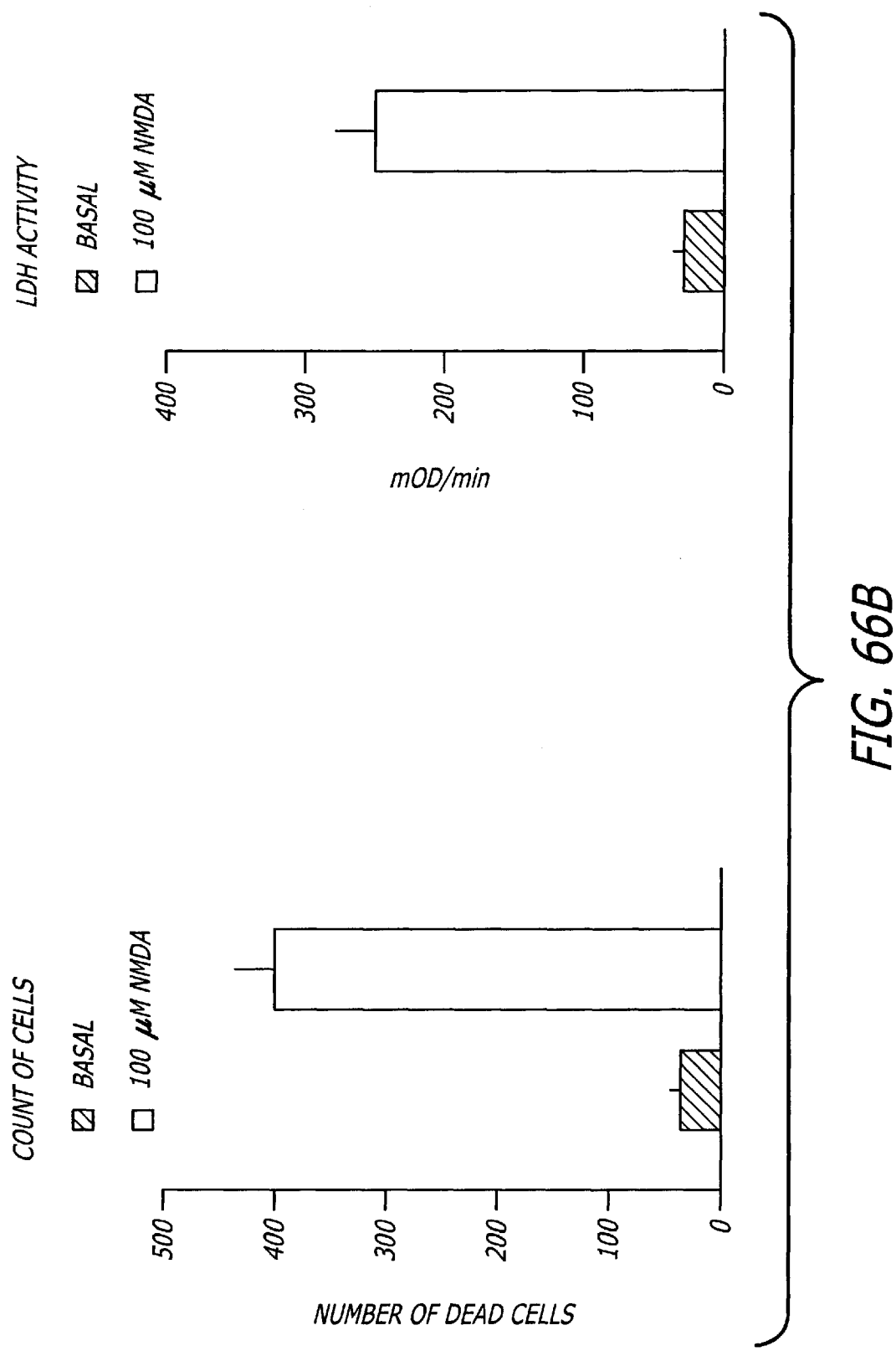
Figure 67A:
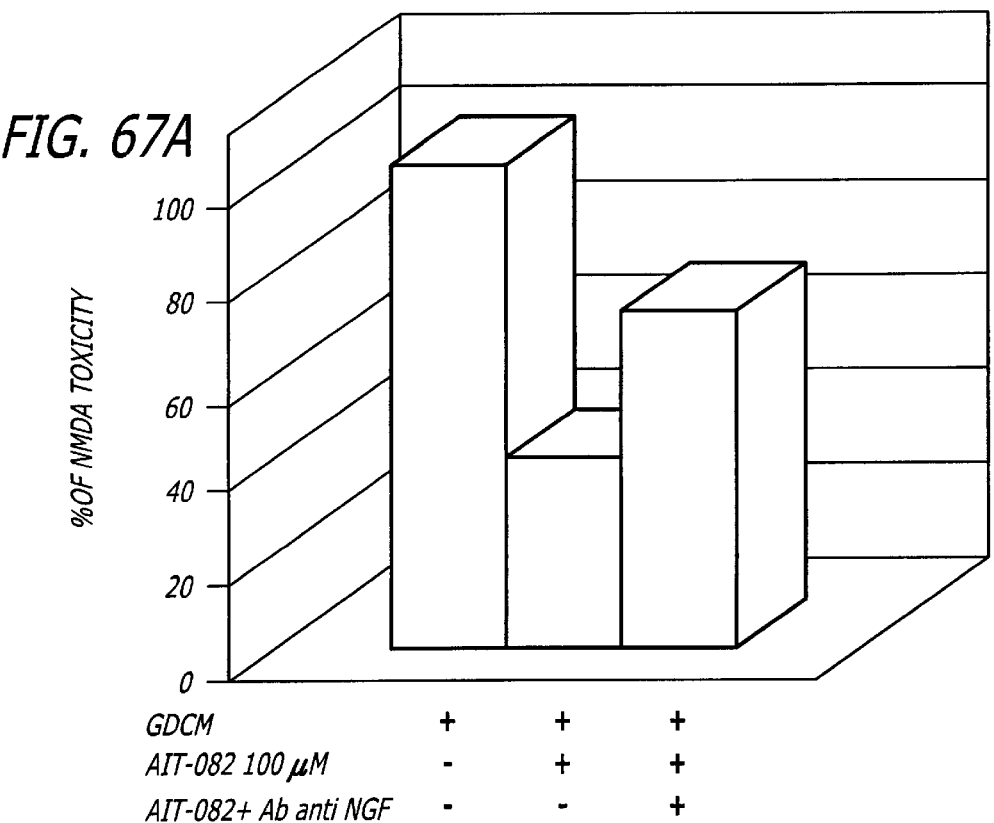
FIG. 67A is a graph showing the protection provided by CM alone or together with 100 $\mu$M AIT-082 for hippocampal cells, together with results when anti-NGF antibody is added together with CM and AIT-082.
Figure 67B:
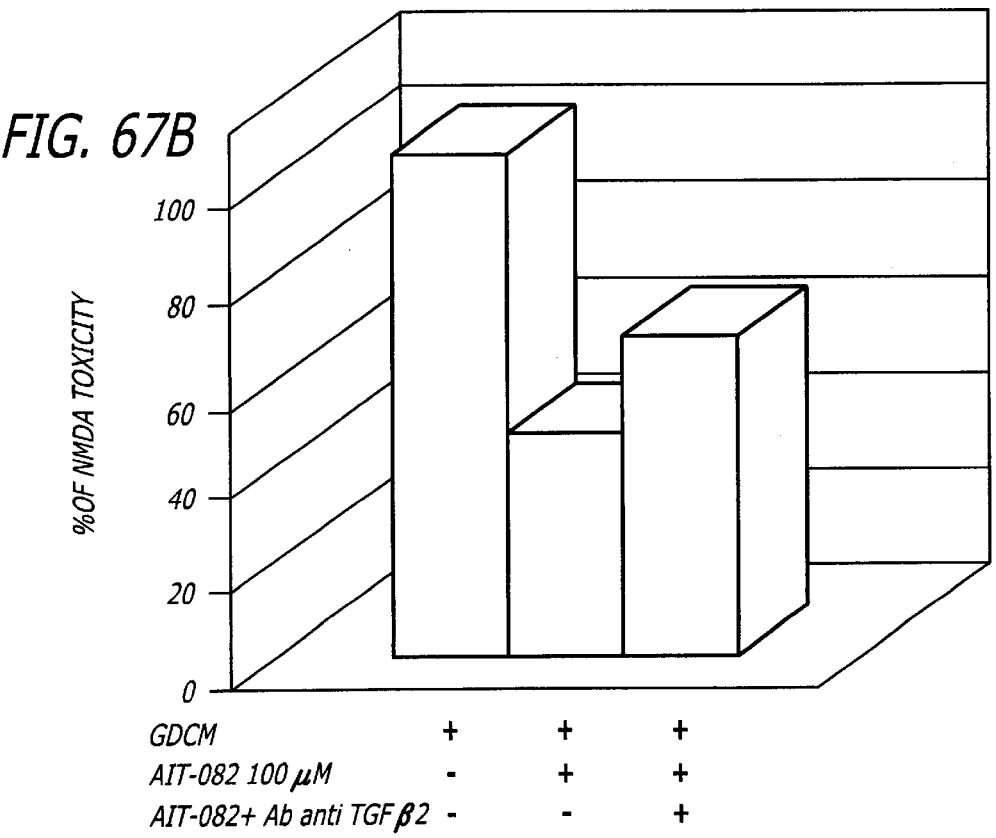
FIG. 67B is a graph showing the protection provided by CM alone or together with 100 $\mu$M AIT-082 for hippocampal cells, together with results when anti-$TGF\beta_2$ antibody is added together with CM and AIT-082.

The experimental scheme for the use of conditioned medium (CM) is shown in FIG. 65. The effects of NMDA are shown in FIG. 66A on cortical cells and in FIG. 66B for hippocampal cells. In FIGS. 66A and 66B, the effect of 100 μM NMDA on the cell cultures is shown; NMDA increased the number of dead cells as measured by Trypan Blue staining and increased the release of LDH activity. In FIG. 67A, the protection provided by CM alone or together with 100 μM AIT-082 for hippocampal cells is shown, together with results when anti-NGF antibody is added together with CM and AIT-082. Similarly, in FIG. 67B, the protection provided by CM alone or together with 100 μM AIT-082 for hippocampal cells is shown, together with results when anti-TGFβ$_2$ antibody is added together with CM and AIT- 082. These results indicate that AIT-082 provides protection against the excitotoxic effects of NMDA, and this protection is partially counteracted by antibodies against TGFβ$_2$ or NGF, suggesting that the protection is mediated by these factors. Specifically, CM alone reduced cell damage by about 20%. The combination of AIT-082 and CM reduced cell damage by approximately 70–80%, and this reduction in cell damage was counteracted to a significant degree when antibodies to NGF (FIG. 67A) or TGFβ$_2$ (FIG. 67B) were added.

Since it has been previously found that the stimulation of A$_1$ adenosine receptor increased the production of trophic factors from astrocytes and that AIT-082 is able to increase the extracellular adenosine levels in the culture medium of astrocytes, it was investigated whether the neuroprotective effect of CM was modified by adding, at the same time, CM and a selective blocker of A$_1$ adenosine receptor, 8-cyclopentyl-1,3-dipropylxanthine (DPCPX)(100 nm) to the injured cortical neurons. DPCPX did not modify the neuroprotective effect of astrocyte-derived CM. Conversely, when DPCPX (100 nm) was added to astrocyte cultures together with AIT-082, the neuroprotective effect of the resulting CM deriving from the culture of the astrocytes with AIT-082 was reduced by only 20%, as compared to the neuroprotective effect of CM derived from astrocytes exposed to AIT-082 alone (assumed as equal to 100%).

To summarize the conclusions of this Example, AIT-082 stimulates astrocytes to synthesize and release NFs. Indeed, this compound dose- and time-dependently increased the production of NGF and TGFβ$_2$ from astrocytes. NGF accumulation in the culture medium was greater than that of TGFβ$_2$ as compared with control. Moreover, the enhancement in the release of both NFs needs some hours of cell exposure to the drug and the activation of ex novo protein synthesis. The increased production of NFs caused by AIT-082 involves the activation of MAP kinase cascade, whose rapid onset likely suggests a direct effect of this drug on this signal transduction pathway. However, specific receptors for this hypoxanthine derivative are yet unknown. The AIT-082 induced production of NGF and TGFβ$_2$ by astrocytes is directly involved in the neuroprotective effect exerted by this agent in vivo.

EXAMPLE 40

Summary of Effects of AIT-082 on Production of mRNA Encoding Growth Factors and on Production of Growth Factor Proteins The constellation of effects of AIT-082 on production of mRNA encoding growth factors and on production of growth factor proteins is shown in Table R. The results summarized in Table S show both transcriptional and translational effects on growth factors that are in the categories of neurotrophins, pleiotrophins, members of the S100 family of EF hand calcium binding proteins, and members of the TGFβ superfamily. As indicated, effects have been shown at both the mRNA (transcriptional) and protein (translational) levels.

TABLE R

Constellation of Effects of AIT-082 on Production of mRNA Coding for Growth Factors and Production of Growth Factor Proteins

|  | Cultured Cells | Normal Brain | Aged Brain | Lesioned Brain | Normal Spinal Cord | Lesioned Spinal Cord |
|---|---|---|---|---|---|---|
| Neurotrophins |  |  |  |  |  |  |
| NGF | ±/+ | − | ± | ±/− | − | nt |
| NT-3 | ± | + | + | ±/+ | − | ± |
| BDNF | nt | + | + | ±/+ | + | ± |
| Pleiotrophins |  |  |  |  |  |  |
| bFGF | ±/+ | nt | ± | ± | nt | nt |
| CNTF | nt | nt | nt | nt | ± | ± |
| S100 Family (EF Hand Calcium-Binding Proteins) |  |  |  |  |  |  |
| S100β | + | nt | nt | nt | nt | nt |
| TGFβ Superfamily |  |  |  |  |  |  |
| TGFβ$_1$ | + | nt | nt | nt | nt | nt |
| GDNF | nt | + | + | + | + | nt |

± = mRNA
+ = protein
nt = not tested

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A method for selectively and controllably inducing the in vivo genetic expression of at least one naturally occurring genetically encoded molecule in a mammal comprising the step of administering an effective amount of at least one carbon monoxide dependent guanylyl cyclase modulating purine derivative to the mammal.

2. The method of claim 1 wherein the at least one naturally genetically encoded molecule stimulates neuritogenesis.

3. The method of claim 2 wherein the at least one naturally occurring genetically encoded molecule that stimulates neuritogenesis is selected from the group consisting of neurotrophins, pleiotrophins, members of the S100 family of EF hand calcium binding proteins, and members of the TGFβ superfamily.

4. The method of claim 3 wherein the at least one naturally occurring genetically encoded molecule that stimulates neuritogenesis is a neurotrophin.

5. The method of claim 4 wherein the neurotrophin is selected from the group consisting of nerve growth factor (NGF), NT-3, and brain-derived neurotrophic factor (BDNF).

6. The method of claim 5 wherein the neurotrophin is NGF.

7. The method of claim 5 wherein the neurotrophin is NT-3.

8. The method of claim 5 wherein the neurotrophin is BDNF.

9. The method of claim 3 wherein the at least one naturally occurring genetically encoded molecule that stimulates neuritogenesis is a pleiotrophin.

10. The method of claim 9 wherein the pleiotrophin is selected from the group consisting of basic fibroblast growth factor (bFGF) and ciliary neurotrophic factor (CNTF).

11. The method of claim 10 wherein the pleiotrophin is bFGF.

12. The method of claim 10 wherein the pleiotrophin is CNTF.

13. The method of claim 3 wherein the at least one naturally occurring genetically encoded molecule that stimulates neuritogenesis is a member of the S100 family of EF hand calcium binding proteins.

14. The method of claim 13 wherein the member of the S100 family of EF hand calcium binding proteins is selected from the group consisting of S100β, p11, p9Ka, and calcyclin.

15. The method of claim 14 wherein the member of the S100 family of EF hand calcium binding proteins is S100β.

16. The method of claim 14 wherein the member of the S100 family of EF hand calcium binding proteins is p11.

17. The method of claim 14 wherein the member of the S100 family of EF hand calcium binding proteins is p9Ka.

18. The method of claim 14 wherein the member of the S100 family of EF hand calcium binding proteins is calcyclin.

19. The method of claim 3 wherein the at least one naturally occurring genetically encoded molecule that stimulates neuritogenesis is a member of the TGFβ superfamily.

20. The method of claim 19 wherein the member of the TGFβ superfamily is selected from the group consisting of TGFβ$_1$ and glial cell line-derived neurotrophic factor (GDNF).

21. The method of claim 20 wherein the member of the TGFβ superfamily is TGFβ$_1$.

22. The method of claim 20 wherein the member of the TGFβ superfamily is GDNF.

23. The method of claim 1 wherein the inducing of the in vivo genetic expression of at least one naturally occurring genetically encoded molecule occurs in astrocytes of the mammal.

24. The method of claim 1 wherein the inducing of the in vivo genetic expression of at least one naturally occurring genetically encoded molecule activates the mitogen-activated protein kinase cascade.

25. The method of claim 1 wherein the carbon monoxide dependent cyclase modulating purine derivative is selected from the group consisting of guanosine, inosine pranobex, and a compound of formula (I)

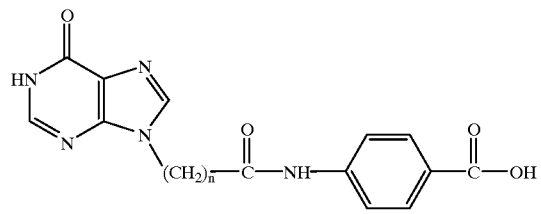

where n is an integer from 1 to 6 or of a salt or prodrug ester of a compound of formula (I) where n is an integer from 1 to 6.

26. The method of claim 25 wherein the compound is a compound of formula (I) wherein n is an integer from 1 to 6.

27. The method of claim 26 wherein n is 2 and wherein the compound is N-4-carboxyphenyl-3-(6-oxohydropurin-9-yl)propanamide.

28. The method of claim 1 wherein the effective amount of the at least one carbon monoxide dependent guanylyl cyclase modulating purine derivative produces a treating concentration of at least 1 μM.

29. The method of claim 1 wherein the at least one carbon monoxide dependent guanylyl cyclase modulating purine derivative is orally administered to the mammal.

30. The method of claim 1 wherein the at least one carbon monoxide dependent guanylyl cyclase modulating purine derivative is administered to the mammal by injection.

31. The method of claim 1 wherein the mammal is a human.

32. A method for the administration of at least one naturally occurring genetically encoded molecule to a mammal comprising the step of selectably inducing the in vivo genetic expression of the molecule in the mammal through the administration of an effective amount of at least one carbon monoxide dependent guanylyl cyclase modulating purine derivative to the mammal to raise the concentration of the at least one naturally occurring genetically encoded molecule in at least one tissue of the mammal and thus cause the administration of the at least one naturally occurring genetically encoded molecule to the mammal.

33. The method of claim 32 wherein the at least one naturally occurring genetically encoded molecule stimulates neuritogenesis.

34. The method of claim 33 wherein the at least one naturally occurring genetically encoded molecule that stimulates neuritogenesis is selected from the group consisting of neurotrophins, pleiotrophins, members of the S100 family of EF hand calcium binding proteins, and members of the TGFβ superfamily.

35. The method of claim 34 wherein the at least one naturally occurring genetically encoded molecule that stimulates neuritogenesis is a neurotrophin.

36. The method of claim 35 wherein the neurotrophin is selected from the group consisting of NGF, NT-3, and BDNF.

37. The method of claim 36 wherein the neurotrophin is NGF.

38. The method of claim 36 wherein the neurotrophin is NT-3.

39. The method of claim 36 wherein the neurotrophin is BDNF.

40. The method of claim 34 wherein the at least one naturally occurring genetically encoded molecule that stimulates neuritogenesis is a pleiotrophin.

41. The method of claim 40 wherein the pleiotrophin is selected from the group consisting of bFGF and CNTF.

42. The method of claim 41 wherein the pleiotrophin is bFGF.

43. The method of claim 41 wherein the pleiotrophin is CNTF.

44. The method of claim 34 wherein the at least one naturally occurring genetically encoded molecule that stimulates neuritogenesis is a member of the S100 family of EF hand calcium binding proteins.

45. The method of claim 44 wherein the member of the S100 family of EF hand calcium binding proteins is selected from the group consisting of S100β, p11, p9Ka, and calcyclin.

46. The method of claim 45 wherein the member of the S100 superfamily of EF hand calcium binding proteins is S100β.

47. The method of claim 45 wherein the member of the S-100 family of EF hand calcium binding proteins is p11.

48. The method of claim 45 wherein the member of the S-100 family of EF hand calcium binding proteins is p9Ka.

49. The method of claim 45 wherein the member of the S-100 family of EF hand calcium binding proteins is calcyclin.

50. The method of claim 34 wherein the at least one naturally occurring genetically encoded molecule that stimulates neuritogenesis is a member of the TGFβ superfamily.

51. The method of claim 50 wherein the member of the TGFβ superfamily is selected from the group consisting of TGFβ$_1$ and GDNF.

52. The method of claim 51 wherein the member of the TGFβ superfamily is TGFβ$_1$.

53. The method of claim 51 wherein the member of the TGFβ$_1$ superfamily is GDNF.

54. The method of claim 32 wherein the inducing of the in vivo genetic expression of at least one naturally occurring genetically encoded molecule occurs in astrocytes of the mammal.

55. The method of claim 32 wherein the inducing of the in vivo genetic expression of at least one naturally occurring genetically encoded molecule activates the mitogen-activated protein kinase cascade.

56. The method of claim 32 wherein the carbon monoxide dependent guanylyl cyclase modulating purine derivative is selected from the group consisting of guanosine, inosine pranobex, and a compound of formula (I) where n is an integer from 1 to 6, or of a salt or prodrug ester of a compound of formula (I) where n is an integer from 1 to 6.

57. The method of claim 56 wherein the compound is a compound of formula (I) wherein n is an integer from 1 to 6.

58. The method of claim 57 wherein n is 2 and wherein the compound is N-4-carboxyphenyl-3-(6-oxohydropurin-9-yl)propanamide.

59. The method of claim 32 wherein the effective amount of the at least one carbon monoxide dependent guanylyl cyclase modulating purine derivative produces a treating concentration of at least 1 μM.

60. The method of claim 32 wherein the at least one carbon monoxide dependent guanylyl cyclase modulating purine derivative is orally administered to the mammal.

61. The method of claim 32 wherein the at least one carbon monoxide dependent guanylyl cyclase modulating purine derivative is administered to the mammal by injection.

62. The method of claim 32 wherein the mammal is a human.

63. A method for modifying the membrane potential of a mammalian neuron comprising the step of administering an effective amount of at least one carbon monoxide dependent guanylyl cyclase modulating purine derivative to the mammalian neuron.

64. The method of claim 63 wherein the effective amount of the at least one carbon monoxide dependent guanylyl cyclase is administered to a mammal so that the method produces an increased learning capability in the mammal.

65. The method of claim 63 wherein the carbon monoxide dependent guanylyl cyclase modulating purine derivative is selected from the group consisting of guanosine, inosine pranobex, and a compound of formula (I) where n is an integer from 1 to 6, or of a salt or prodrug ester of a compound of formula (I) where n is an integer from 1 to 6.

66. The method of claim 65 wherein the compound is a compound of formula (I) wherein n is an integer from 1 to 6.

67. The method of claim 66 wherein n is 2 and wherein the compound is N-4-carboxyphenyl-3-(6-oxohydropurin-9-yl)propanamide.

68. A method for selectively and controllably inducing the in vivo genetic expression of at least one naturally occurring genetically encoded molecule in a mammal comprising the step of administering an effective amount of at least one carbon monoxide dependent guanylyl cyclase modulating guanine derivative to the mammal, the guanine derivative comprising a guanine moiety linked through its nitrogen-9 atom through a linker to a physiologically active group.

69. The method of claim 68 wherein the linker of the guanine derivative incorporates a hydrocarbyl moiety that includes a carbonyl group at one end.

70. The method of claim 69 wherein the end of the hydrocarbyl moiety that is terminated with the carbonyl group is linked to the physiologically active group through an amide linkage.

71. The method of claim 68 wherein the at least one naturally genetically encoded molecule stimulates neuritogenesis.

72. The method of claim 71 wherein the at least one naturally occurring genetically encoded molecule that stimulates neuritogenesis is selected from the group consisting of neurotrophins, pleiotrophins, members of the S100 family of EF hand calcium binding proteins, and members of the TGFβ superfamily.

73. The method of claim 68 wherein the guanine derivative comprises a compound of formula (II)

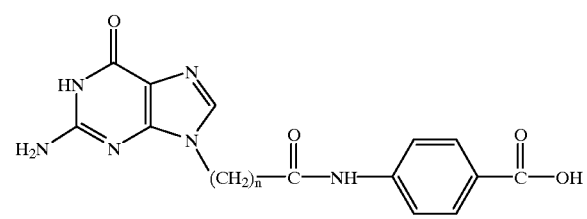

(II)

wherein n is an integer from 1 to 6.

74. The method of claim 73 wherein n is 2 and the compound is N-4-carboxyphenyl-3-(2-amino-6-oxohydropurin-9-yl)propanamide.

75. The method of claim 68 wherein the inducing of the in vivo genetic expression of at least one naturally occurring genetically encoded molecule occurs in astrocytes of the mammal.

76. The method of claim 68 wherein the inducing of the in vivo genetic expression of at least one naturally occurring genetically encoded molecule activates the mitogen-activated protein kinase cascade.

77. A method for the administration of at least one naturally occurring genetically encoded molecule to a mammal comprising the step of selectably inducing the in vivo genetic expression of the molecule in the mammal through the administration of an effective amount of at least one carbon monoxide dependent guanylyl cyclase modulating guanine derivative to the mammal to raise the concentration of the at least one naturally occurring genetically encoded molecule in at least one tissue of the mammal and thus cause the administration of the at least one naturally occurring genetically encoded molecule to the mammal, the guanine derivative comprising a guanine moiety linked through its nitrogen-9 atom through a linker to a physiologically active group.

78. The method of claim 77 wherein the linker of the guanine derivative incorporates a hydrocarbyl moiety that includes a carbonyl group at one end.

79. The method of claim 78 wherein the end of the hydrocarbyl moiety that is terminated with the carbonyl group is linked to the physiologically active group through an amide linkage.

80. The method of claim 77 wherein the at least one naturally genetically encoded molecule stimulates neuritogenesis.

81. The method of claim 80 wherein the at least one naturally occurring genetically encoded molecule that stimulates neuritogenesis is selected from the group consisting of neurotrophins, pleiotrophins, members of the S100 family of EF hand calcium binding proteins, and members of the TGFβ superfamily.

82. The method of claim 77 wherein the guanine derivative comprises a compound of formula (II) wherein n is an integer from 1 to 6.

83. The method of claim 82 wherein n is 2 and the compound is N-4-carboxyphenyl-3-(2-amino-6-oxohydropurin-9-yl)propanamide.

84. The method of claim 77 wherein the inducing of the in vivo genetic expression of at least one naturally occurring genetically encoded molecule occurs in astrocytes of the mammal.

85. The method of claim 77 wherein the inducing of the in vivo genetic expression of at least one naturally occurring genetically encoded molecule activates the mitogen-activated protein kinase cascade.

* * * * *